US008808314B2

(12) United States Patent
Levin et al.

(10) Patent No.: US 8,808,314 B2
(45) Date of Patent: Aug. 19, 2014

(54) DEVICE AND METHOD FOR DEPLOYING AND ATTACHING AN IMPLANT TO A BIOLOGICAL TISSUE

(75) Inventors: Ofek Levin, Moshav Amirim (IL); Arie Levy, Ramat-Gan (IL); Lena Levin, Moshav Amirim (IL)

(73) Assignee: Covidien LP, Mansfield, MA (US)

( * ) Notice: Subject to any disclaimer, the term of this patent is extended or adjusted under 35 U.S.C. 154(b) by 436 days.

(21) Appl. No.: 12/890,816

(22) Filed: Sep. 27, 2010

(65) Prior Publication Data

US 2011/0054500 A1    Mar. 3, 2011

Related U.S. Application Data

(63) Continuation of application No. 12/834,456, filed on Jul. 12, 2010, which is a continuation-in-part of application No. PCT/IL2009/000188, filed on Feb. 18, 2009.

(60) Provisional application No. 61/029,386, filed on Feb. 18, 2008.

(51) Int. Cl.
*A61B 17/00* (2006.01)
*A61F 2/02* (2006.01)

(52) U.S. Cl.
USPC .......................... 606/151; 606/213; 606/215

(58) Field of Classification Search
None
See application file for complete search history.

(56) References Cited

U.S. PATENT DOCUMENTS

| | | |
|---|---|---|
| 4,347,847 A | 9/1982 | Usher |
| 4,400,833 A | 8/1983 | Kurland |
| 4,452,245 A | 6/1984 | Usher |
| 4,485,816 A | 12/1984 | Krumme |
| 4,585,458 A | 4/1986 | Kurland |
| 4,633,873 A | 1/1987 | Dumican et al. |
| 4,838,884 A | 6/1989 | Dumican et al. |
| 4,854,316 A | 8/1989 | Davis |
| 5,019,096 A | 5/1991 | Fox, Jr. et al. |
| 5,116,357 A | 5/1992 | Eberbach |
| 5,122,155 A | 6/1992 | Eberbach |
| 5,125,553 A | 6/1992 | Oddsen et al. |
| 5,141,515 A | 8/1992 | Eberbach |

(Continued)

FOREIGN PATENT DOCUMENTS

| | | |
|---|---|---|
| CA | 2413904 A1 | 10/2003 |
| EP | 0328421 A2 | 8/1989 |

(Continued)

OTHER PUBLICATIONS

Extended European Search Report corresponding to EP 09 71 3121.3, completed Jul. 22, 2013 and mailed Jul. 29, 2013; (7 pp).

(Continued)

*Primary Examiner* — Melanie Tyson
*Assistant Examiner* — Todd J Scherbel

(57) ABSTRACT

This present invention generally relates to devices and methods for repairing an aperture in a biological tissue. In certain embodiments, the invention provides a system for closing an aperture in a biological tissue including a handle, an elongate shaft connected to the handle, and a deployment scaffold connected to the shaft, in which the scaffold is configured to releasably retain a surgical implant and the scaffold is configured to deploy and attach the surgical implant to the biological tissue.

21 Claims, 48 Drawing Sheets

(56) References Cited

U.S. PATENT DOCUMENTS

| | | |
|---|---|---|
| 5,147,374 A | 9/1992 | Fernandez |
| 5,176,692 A | 1/1993 | Wilk et al. |
| 5,203,864 A | 4/1993 | Phillips |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |
| 5,263,969 A | 11/1993 | Phillips |
| 5,289,963 A | 3/1994 | McGarry et al. |
| 5,290,217 A | 3/1994 | Campos |
| 5,292,328 A | 3/1994 | Hain et al. |
| 5,304,187 A | 4/1994 | Green et al. |
| 5,333,624 A | 8/1994 | Tovey |
| 5,354,292 A | 10/1994 | Braeuer et al. |
| 5,356,064 A | 10/1994 | Green et al. |
| 5,356,432 A | 10/1994 | Rutkow et al. |
| 5,364,002 A | 11/1994 | Green et al. |
| 5,364,004 A | 11/1994 | Davidson |
| 5,366,460 A | 11/1994 | Eberbach |
| 5,368,602 A | 11/1994 | de la Torre |
| 5,370,650 A | 12/1994 | Tovey et al. |
| 5,376,097 A | 12/1994 | Phillips |
| 5,383,477 A | 1/1995 | DeMatteis |
| 5,392,978 A | 2/1995 | Velez et al. |
| 5,395,383 A * | 3/1995 | Adams et al. ............... 606/151 |
| 5,397,331 A | 3/1995 | Himpens et al. |
| 5,397,332 A * | 3/1995 | Kammerer et al. .......... 606/151 |
| 5,405,360 A | 4/1995 | Tovey |
| 5,425,357 A | 6/1995 | Moll et al. |
| 5,425,740 A | 6/1995 | Hutchinson |
| 5,433,996 A | 7/1995 | Kranzler et al. |
| 5,464,403 A | 11/1995 | Kieturakis et al. |
| 5,497,933 A | 3/1996 | DeFonzo et al. |
| 5,531,759 A | 7/1996 | Kensey et al. |
| 5,560,224 A | 10/1996 | Tessler |
| 5,560,532 A | 10/1996 | DeFonzo et al. |
| 5,564,615 A | 10/1996 | Bishop et al. |
| 5,569,273 A | 10/1996 | Titone et al. |
| 5,577,654 A | 11/1996 | Bishop |
| 5,588,580 A | 12/1996 | Paul et al. |
| 5,588,581 A | 12/1996 | Conlon et al. |
| 5,601,224 A | 2/1997 | Bishop et al. |
| 5,614,284 A | 3/1997 | Kranzler et al. |
| 5,618,290 A | 4/1997 | Toy et al. |
| 5,626,587 A | 5/1997 | Bishop et al. |
| 5,634,584 A | 6/1997 | Okorocha et al. |
| 5,634,931 A | 6/1997 | Kugel |
| 5,662,662 A | 9/1997 | Bishop et al. |
| 5,695,525 A | 12/1997 | Mulhauser et al. |
| 5,716,409 A | 2/1998 | Debbas |
| 5,725,577 A | 3/1998 | Saxon |
| 5,728,119 A | 3/1998 | Smith et al. |
| 5,749,895 A | 5/1998 | Sawyer et al. |
| 5,766,246 A | 6/1998 | Mulhauser et al. |
| 5,769,864 A | 6/1998 | Kugel |
| 5,779,728 A | 7/1998 | Lunsford et al. |
| 5,810,851 A | 9/1998 | Yoon |
| 5,814,058 A | 9/1998 | Carlson et al. |
| 5,817,109 A | 10/1998 | McGarry et al. |
| 5,824,082 A | 10/1998 | Brown |
| 5,836,961 A | 11/1998 | Kieturakis et al. |
| 5,854,383 A | 12/1998 | Erneta et al. |
| 5,863,531 A | 1/1999 | Naughton et al. |
| 5,865,728 A | 2/1999 | Moll et al. |
| 5,911,726 A | 6/1999 | Belknap |
| 5,916,225 A | 6/1999 | Kugel |
| 5,925,058 A | 7/1999 | Smith et al. |
| 5,951,997 A | 9/1999 | Bezwada et al. |
| 5,954,767 A | 9/1999 | Pajotin et al. |
| 5,972,007 A | 10/1999 | Sheffield et al. |
| 5,972,008 A | 10/1999 | Kalinski et al. |
| 5,990,378 A | 11/1999 | Ellis |
| 6,004,333 A | 12/1999 | Sheffield et al. |
| 6,042,592 A | 3/2000 | Schmitt |
| 6,066,776 A | 5/2000 | Goodwin et al. |
| 6,066,777 A | 5/2000 | Benchetrit |
| 6,090,116 A | 7/2000 | D'Aversa et al. |
| 6,113,609 A | 9/2000 | Adams |
| 6,113,611 A | 9/2000 | Allen et al. |
| 6,113,624 A | 9/2000 | Bezwada et al. |
| 6,166,286 A | 12/2000 | Trabucco |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,197,036 B1 | 3/2001 | Tripp et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,113 B1 | 7/2001 | Adams et al. |
| 6,258,124 B1 | 7/2001 | Darois et al. |
| 6,267,772 B1 | 7/2001 | Mulhauser et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,293,906 B1 * | 9/2001 | Vanden Hoek et al. ......... 600/37 |
| 6,312,442 B1 | 11/2001 | Kieturakis et al. |
| 6,319,264 B1 | 11/2001 | Tormala et al. |
| 6,368,541 B1 | 4/2002 | Pajotin et al. |
| 6,375,662 B1 | 4/2002 | Schmitt |
| 6,383,201 B1 | 5/2002 | Dong |
| 6,391,060 B1 | 5/2002 | Ory et al. |
| 6,408,656 B1 | 6/2002 | Ory et al. |
| 6,416,486 B1 | 7/2002 | Wampler |
| 6,425,900 B1 | 7/2002 | Knodel et al. |
| 6,425,924 B1 | 7/2002 | Rousseau |
| 6,436,030 B2 | 8/2002 | Rehil |
| 6,447,524 B1 | 9/2002 | Knodel et al. |
| 6,478,803 B1 | 11/2002 | Kapec et al. |
| 6,485,503 B2 | 11/2002 | Jacobs et al. |
| 6,497,650 B1 | 12/2002 | Nicolo |
| 6,517,584 B1 | 2/2003 | Lecalve |
| 6,527,785 B2 | 3/2003 | Sancoff et al. |
| 6,551,241 B1 | 4/2003 | Schultz |
| 6,551,333 B2 | 4/2003 | Kuhns et al. |
| 6,558,400 B2 | 5/2003 | Deem et al. |
| 6,565,590 B2 | 5/2003 | Kieturakis et al. |
| 6,575,988 B2 | 6/2003 | Rousseau |
| 6,607,541 B1 | 8/2003 | Gardiner et al. |
| 6,610,006 B1 | 8/2003 | Amid et al. |
| 6,613,059 B2 | 9/2003 | Schaller et al. |
| 6,616,685 B2 | 9/2003 | Rousseau |
| 6,638,208 B1 | 10/2003 | Natarajan et al. |
| 6,638,284 B1 | 10/2003 | Rousseau et al. |
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker et al. |
| 6,695,856 B2 | 2/2004 | Kieturakis et al. |
| 6,709,442 B2 | 3/2004 | Miller et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,867 B2 | 6/2004 | Rousseau |
| 6,773,438 B1 | 8/2004 | Knodel et al. |
| 6,783,554 B2 | 8/2004 | Amara et al. |
| 6,790,213 B2 | 9/2004 | Cherok et al. |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl et al. |
| 6,837,893 B2 | 1/2005 | Miller |
| 6,893,452 B2 | 5/2005 | Jacobs |
| 6,913,607 B2 | 7/2005 | Ainsworth et al. |
| 6,913,622 B2 | 7/2005 | Gjunter |
| 6,936,052 B2 | 8/2005 | Gellman et al. |
| 6,945,980 B2 | 9/2005 | Nguyen et al. |
| 6,953,428 B2 | 10/2005 | Gellman et al. |
| 6,960,217 B2 | 11/2005 | Bolduc |

(56) References Cited

U.S. PATENT DOCUMENTS

| | | |
|---|---|---|
| 6,960,233 B1 | 11/2005 | Berg et al. |
| 6,966,916 B2 | 11/2005 | Kumar |
| 6,974,586 B2 | 12/2005 | Greenhalgh et al. |
| 6,991,597 B2 | 1/2006 | Gellman et al. |
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,491,232 B2 | 2/2009 | Bolduc et al. |
| 7,500,945 B2 | 3/2009 | Cox et al. |
| 7,500,993 B2 | 3/2009 | De La Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 8,097,008 B2 * | 1/2012 | Henderson .................... 606/151 |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0027347 A1 | 10/2001 | Rousseau |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rousseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0039453 A1 | 2/2004 | Anderson et al. |
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gingras |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |

(56) References Cited

U.S. PATENT DOCUMENTS

| | | |
|---|---|---|
| 2005/0027369 A1 | 2/2005 | Eldridge et al. |
| 2005/0033318 A1 | 2/2005 | Miller et al. |
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0256532 A1* | 11/2005 | Nayak et al. .................. 606/151 |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147488 A1 | 7/2006 | Wohlert |
| 2006/0147492 A1 | 7/2006 | Hunter et al. |
| 2006/0149316 A1 | 7/2006 | DeVries et al. |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0021756 A1 | 1/2007 | Kortenbach |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0167963 A1 | 7/2007 | Deem et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1* | 8/2007 | Jackson .................. 606/151 |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |

(56) References Cited

U.S. PATENT DOCUMENTS

| | | |
|---|---|---|
| 2008/0167668 A1 | 7/2008 | Criscuolo et al. |
| 2008/0188874 A1 | 8/2008 | Henderson |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0306497 A1 | 12/2008 | Brown et al. |
| 2008/0312751 A1 | 12/2008 | Pugsley et al. |
| 2009/0004239 A1 | 1/2009 | Ladet et al. |
| 2009/0005867 A1 | 1/2009 | Lefranc et al. |
| 2009/0012350 A1 | 1/2009 | Tihon |
| 2009/0012546 A1 | 1/2009 | N'diaye et al. |
| 2009/0018559 A1 | 1/2009 | Buevich et al. |
| 2009/0030434 A1 | 1/2009 | Paz et al. |
| 2009/0030522 A1 | 1/2009 | Cauthen, III et al. |
| 2009/0030527 A1 | 1/2009 | Richter |
| 2009/0036937 A1 | 2/2009 | Cauthen, III et al. |
| 2009/0036989 A1 | 2/2009 | Cauthen, III et al. |
| 2009/0036990 A1 | 2/2009 | Cauthen, III et al. |
| 2009/0036996 A1 | 2/2009 | Roeber |
| 2009/0062823 A1 | 3/2009 | Richter |
| 2009/0069826 A1 | 3/2009 | Walther et al. |
| 2009/0105526 A1 | 4/2009 | Piroli Torelli et al. |
| 2009/0125041 A1 | 5/2009 | Dudai |
| 2009/0137864 A1 | 5/2009 | Cox et al. |
| 2009/0149875 A1 | 6/2009 | Abele et al. |
| 2009/0155332 A1 | 6/2009 | Sherry et al. |
| 2009/0157184 A1 | 6/2009 | Cauthen, III et al. |
| 2009/0157195 A1 | 6/2009 | Siedle |
| 2009/0162273 A1 | 6/2009 | Lawrynowicz et al. |
| 2009/0182190 A1 | 7/2009 | Dann |
| 2009/0182352 A1 | 7/2009 | Paz et al. |
| 2009/0187258 A1 | 7/2009 | Ip et al. |
| 2009/0192346 A1 | 7/2009 | Rosenblatt |
| 2009/0192528 A1 | 7/2009 | Higgins et al. |
| 2009/0198260 A1 | 8/2009 | Ford et al. |
| 2009/0204130 A1 | 8/2009 | Kantsevoy et al. |
| 2009/0204227 A1 | 8/2009 | Derwin et al. |
| 2009/0216075 A1 | 8/2009 | Bell et al. |
| 2009/0216104 A1 | 8/2009 | DeSimone et al. |
| 2009/0216338 A1 | 8/2009 | Gingras et al. |
| 2009/0234379 A1 | 9/2009 | Rehnke |
| 2009/0234461 A1 | 9/2009 | Rehnke |
| 2009/0240342 A1 | 9/2009 | Lindh et al. |
| 2009/0240343 A1 | 9/2009 | Adams |
| 2009/0248048 A1 | 10/2009 | Milbocker |
| 2009/0254103 A1 | 10/2009 | Deutsch |
| 2009/0259094 A1 | 10/2009 | Bouchier et al. |
| 2009/0281563 A1 | 11/2009 | Newell et al. |
| 2010/0069930 A1 | 3/2010 | Roslin et al. |
| 2010/0312357 A1* | 12/2010 | Levin et al. ............... 623/23.72 |
| 2011/0004221 A1 | 1/2011 | Euteneuer et al. |
| 2011/0040310 A1 | 2/2011 | Levin et al. |
| 2011/0040311 A1 | 2/2011 | Levin et al. |

FOREIGN PATENT DOCUMENTS

| | | |
|---|---|---|
| EP | 0525791 A1 | 2/1993 |
| EP | 0537769 A1 | 4/1993 |
| EP | 0544485 A1 | 6/1993 |
| EP | 0556018 A1 | 8/1993 |
| EP | 0557963 A1 | 9/1993 |
| EP | 0557964 A1 | 9/1993 |
| EP | 0573273 A2 | 12/1993 |
| EP | 0579377 A2 | 1/1994 |
| EP | 0581036 A1 | 2/1994 |
| EP | 0614650 A2 | 9/1994 |
| EP | 0702934 A1 | 3/1996 |
| EP | 0744162 A2 | 11/1996 |
| EP | 0581036 | 1/1997 |
| EP | 0519022 B1 | 12/1997 |
| EP | 0827724 A2 | 3/1998 |
| EP | 0553344 B1 | 9/1998 |
| EP | 0746258 B1 | 9/1998 |
| EP | 0898944 A2 | 3/1999 |
| EP | 0908482 A1 | 4/1999 |
| EP | 0986993 A1 | 3/2000 |
| EP | 0837660 B1 | 5/2000 |
| EP | 1060714 A2 | 12/2000 |
| EP | 1145693 A2 | 10/2001 |
| EP | 1181899 A2 | 2/2002 |
| EP | 1199037 A2 | 4/2002 |
| EP | 1199038 A2 | 4/2002 |
| EP | 1219265 A2 | 7/2002 |
| EP | 0746267 B1 | 11/2002 |
| EP | 1018980 B1 | 1/2003 |
| EP | 1306061 A2 | 5/2003 |
| EP | 1317904 A1 | 6/2003 |
| EP | 1366717 A1 | 12/2003 |
| EP | 0783270 B1 | 6/2004 |
| EP | 1200010 B1 | 3/2005 |
| EP | 1164967 B1 | 5/2005 |
| EP | 1541183 A1 | 6/2005 |
| EP | WO2005082273 A1 | 9/2005 |
| EP | 0828453 B1 | 11/2005 |
| EP | 1001717 B1 | 11/2005 |
| EP | 1303230 B1 | 11/2005 |
| EP | 1607048 A1 | 12/2005 |
| EP | 1404250 B1 | 2/2006 |
| EP | 1671604 A2 | 6/2006 |
| EP | 1674048 A1 | 6/2006 |
| EP | 1274473 B1 | 7/2006 |
| EP | 0934024 B1 | 8/2006 |
| EP | 1503683 B1 | 8/2006 |
| EP | 1700579 A1 | 9/2006 |
| EP | 1704832 A2 | 9/2006 |
| EP | 200614650 A2 | 10/2006 |
| EP | 1079741 B1 | 11/2006 |
| EP | 0964645 B1 | 7/2007 |
| EP | 1163019 B1 | 10/2007 |
| EP | 1849440 A1 | 10/2007 |
| EP | 1867348 A2 | 12/2007 |
| EP | 1870056 A1 | 12/2007 |
| EP | 1531739 B1 | 2/2008 |
| EP | 1406557 B1 | 11/2008 |
| EP | 1990014 A2 | 11/2008 |
| EP | 2002800 A1 | 12/2008 |
| EP | 1505927 B1 | 1/2009 |
| EP | 1372525 B1 | 3/2009 |
| EP | 1653880 B1 | 4/2009 |
| EP | 2050474 A2 | 4/2009 |
| EP | 1940312 B1 | 7/2009 |
| FR | 2789888 | 8/2000 |
| FR | 2789888 A1 | 8/2000 |
| WO | WO8204390 A1 | 12/1982 |
| WO | WO92/06639 | 4/1992 |
| WO | WO9206639 A2 | 4/1992 |
| WO | WO9211824 A1 | 7/1992 |
| WO | WO9219162 A2 | 11/1992 |
| WO | WO9221293 A1 | 12/1992 |
| WO | WO9303685 A1 | 3/1993 |
| WO | WO9309722 A1 | 5/1993 |
| WO | WO9317635 A1 | 9/1993 |
| WO | WO9417747 A1 | 8/1994 |
| WO | WO9419029 A1 | 9/1994 |
| WO | WO94/27535 | 12/1994 |
| WO | WO9427535 A1 | 12/1994 |
| WO | WO9530374 A1 | 11/1995 |
| WO | WO9531140 A1 | 11/1995 |
| WO | WO9603091 A1 | 2/1996 |
| WO | WO9603165 A1 | 2/1996 |
| WO | WO9606634 A1 | 3/1996 |
| WO | WO9609795 A1 | 4/1996 |
| WO | WO9640307 A1 | 12/1996 |
| WO | WO9702789 A1 | 1/1997 |
| WO | WO9722371 A1 | 6/1997 |
| WO | WO9732526 A1 | 9/1997 |

(56) References Cited

FOREIGN PATENT DOCUMENTS

| | | |
|---|---|---|
| WO | WO9735533 A1 | 10/1997 |
| WO | WO9803713 A1 | 1/1998 |
| WO | WO9811814 | 3/1998 |
| WO | WO9814134 A2 | 4/1998 |
| WO | WO9816153 A1 | 4/1998 |
| WO | WO9903422 A1 | 1/1999 |
| WO | WO9905992 A1 | 2/1999 |
| WO | WO9916381 A1 | 4/1999 |
| WO | WO9951163 A1 | 10/1999 |
| WO | WO9960931 A1 | 12/1999 |
| WO | WO9962406 A2 | 12/1999 |
| WO | WO9963051 A2 | 12/1999 |
| WO | WO0007520 A1 | 2/2000 |
| WO | WO0016822 A2 | 3/2000 |
| WO | WO0056376 A1 | 9/2000 |
| WO | WO0057796 A1 | 10/2000 |
| WO | WO0057812 A1 | 10/2000 |
| WO | WO0061033 | 10/2000 |
| WO | WO0067663 A1 | 11/2000 |
| WO | WO0071548 A1 | 11/2000 |
| WO | WO0071549 A1 | 11/2000 |
| WO | WO0108594 A1 | 2/2001 |
| WO | WO0126588 A2 | 4/2001 |
| WO | WO0154589 A1 | 8/2001 |
| WO | WO0168653 A1 | 9/2001 |
| WO | WO0170322 A1 | 9/2001 |
| WO | WO0180788 A2 | 11/2001 |
| WO | WO0185060 | 11/2001 |
| WO | WO0189390 A1 | 11/2001 |
| WO | WO0189392 A2 | 11/2001 |
| WO | WO01085058 A2 | 11/2001 |
| WO | WO0207648 A1 | 1/2002 |
| WO | WO0217771 A2 | 3/2002 |
| WO | WO0217796 A1 | 3/2002 |
| WO | WO0217797 A1 | 3/2002 |
| WO | WO0219916 A1 | 3/2002 |
| WO | WO0219923 A1 | 3/2002 |
| WO | WO0222047 A1 | 3/2002 |
| WO | WO0224080 A2 | 3/2002 |
| WO | WO0230336 A2 | 4/2002 |
| WO | WO0232346 A1 | 4/2002 |
| WO | WO02026747 A1 | 4/2002 |
| WO | WO0234140 A2 | 5/2002 |
| WO | WO0235990 A2 | 5/2002 |
| WO | WO02058543 A2 | 8/2002 |
| WO | WO02078568 A1 | 10/2002 |
| WO | WO02080779 A1 | 10/2002 |
| WO | WO02080780 A1 | 10/2002 |
| WO | WO02/091953 | 11/2002 |
| WO | WO02087425 A2 | 11/2002 |
| WO | WO02091928 A1 | 11/2002 |
| WO | WO02091953 A1 | 11/2002 |
| WO | WO02096327 A2 | 12/2002 |
| WO | WO03002029 A1 | 1/2003 |
| WO | WO03002130 A1 | 1/2003 |
| WO | WO03032867 A1 | 4/2003 |
| WO | WO03059180 A2 | 7/2003 |
| WO | WO03059201 A1 | 7/2003 |
| WO | WO03059217 A1 | 7/2003 |
| WO | WO03077730 A2 | 9/2003 |
| WO | WO03082125 A1 | 10/2003 |
| WO | WO03084410 A1 | 10/2003 |
| WO | WO03088846 A1 | 10/2003 |
| WO | WO03090633 A2 | 11/2003 |
| WO | WO03094781 A1 | 11/2003 |
| WO | WO03094783 A1 | 11/2003 |
| WO | WO03094786 A1 | 11/2003 |
| WO | WO03094787 A1 | 11/2003 |
| WO | WO03096909 A1 | 11/2003 |
| WO | WO03096929 A1 | 11/2003 |
| WO | WO03097011 A1 | 11/2003 |
| WO | WO2003092509 A1 | 11/2003 |
| WO | WO03099160 A1 | 12/2003 |
| WO | WO03103473 A2 | 12/2003 |
| WO | WO2004004600 A1 | 1/2004 |
| WO | WO2004006808 A2 | 1/2004 |
| WO | WO2004012579 A2 | 2/2004 |
| WO | WO2004012627 A1 | 2/2004 |
| WO | WO2004019787 A2 | 3/2004 |
| WO | WO2004024030 A1 | 3/2004 |
| WO | WO2004034924 A2 | 4/2004 |
| WO | WO2004037123 A1 | 5/2004 |
| WO | WO2004/062529 | 7/2004 |
| WO | WO2004058286 A1 | 7/2004 |
| WO | WO2004060425 A2 | 7/2004 |
| WO | WO2004062529 A2 | 7/2004 |
| WO | WO2004062530 A1 | 7/2004 |
| WO | WO2004028547 A1 | 8/2004 |
| WO | WO2004069866 A1 | 8/2004 |
| WO | WO2004/080348 | 9/2004 |
| WO | WO2004080348 A1 | 9/2004 |
| WO | WO2004087227 A1 | 10/2004 |
| WO | WO2004093737 A1 | 11/2004 |
| WO | WO2004098461 A2 | 11/2004 |
| WO | WO2004098665 A1 | 11/2004 |
| WO | WO2004100841 A1 | 11/2004 |
| WO | WO2004101002 A2 | 11/2004 |
| WO | WO2004103166 A2 | 12/2004 |
| WO | WO2004103414 A2 | 12/2004 |
| WO | WO2005003351 A1 | 1/2005 |
| WO | WO2005004727 A1 | 1/2005 |
| WO | WO2005007209 A1 | 1/2005 |
| WO | WO2005014634 A1 | 2/2005 |
| WO | WO2005018494 A1 | 3/2005 |
| WO | WO2005019241 A2 | 3/2005 |
| WO | WO2005019315 A1 | 3/2005 |
| WO | WO2005035548 A1 | 4/2005 |
| WO | WO2005041784 A2 | 5/2005 |
| WO | WO2005044143 A1 | 5/2005 |
| WO | WO2005051172 A2 | 6/2005 |
| WO | WO2005055958 A2 | 6/2005 |
| WO | WO2005065324 A2 | 7/2005 |
| WO | WO2005065552 A2 | 7/2005 |
| WO | WO2005079335 A2 | 9/2005 |
| WO | WO2005082274 A1 | 9/2005 |
| WO | WO2005094721 A1 | 10/2005 |
| WO | WO2005099628 A2 | 10/2005 |
| WO | WO2005102209 A1 | 11/2005 |
| WO | WO2005105172 A2 | 11/2005 |
| WO | WO2005110243 A2 | 11/2005 |
| WO | WO2005110273 A1 | 11/2005 |
| WO | WO2006002439 A1 | 1/2006 |
| WO | WO2006008429 A1 | 1/2006 |
| WO | WO2006012353 A2 | 2/2006 |
| WO | WO2006013337 A2 | 2/2006 |
| WO | WO2006015031 A2 | 2/2006 |
| WO | WO2006026509 A2 | 3/2006 |
| WO | WO2006034117 A1 | 3/2006 |
| WO | WO2006036936 A2 | 4/2006 |
| WO | WO2006037047 A2 | 4/2006 |
| WO | WO2006040760 A2 | 4/2006 |
| WO | WO2006044785 A1 | 4/2006 |
| WO | WO2006047645 A2 | 5/2006 |
| WO | WO2006048885 A1 | 5/2006 |
| WO | WO2006082587 A2 | 8/2006 |
| WO | WO2006086339 A2 | 8/2006 |
| WO | WO2006092159 A1 | 9/2006 |
| WO | WO2006092236 A1 | 9/2006 |
| WO | WO2006102457 A2 | 9/2006 |
| WO | WO2006116000 A2 | 11/2006 |
| WO | WO2006119034 A2 | 11/2006 |
| WO | WO2007004228 A2 | 1/2007 |
| WO | WO2007011689 A2 | 1/2007 |
| WO | WO2007017872 A2 | 2/2007 |
| WO | WO2007021620 A2 | 2/2007 |
| WO | WO2007021759 A2 | 2/2007 |
| WO | WO2007021834 A1 | 2/2007 |
| WO | WO2007/025302 | 3/2007 |
| WO | WO/2007/030676 | 3/2007 |
| WO | WO2007025293 A2 | 3/2007 |
| WO | WO2007025296 A2 | 3/2007 |
| WO | WO2007025302 A2 | 3/2007 |
| WO | WO2007030676 A2 | 3/2007 |
| WO | WO2007034145 A2 | 3/2007 |

(56) References Cited

FOREIGN PATENT DOCUMENTS

| | | |
|---|---|---|
| WO | WO2007050382 A1 | 5/2007 |
| WO | WO2007051221 A1 | 5/2007 |
| WO | WO2007055755 A1 | 5/2007 |
| WO | WO2007070141 A1 | 6/2007 |
| WO | WO2007072469 A2 | 6/2007 |
| WO | WO2007081955 A1 | 7/2007 |
| WO | WO2007087132 A1 | 8/2007 |
| WO | WO2007087146 A2 | 8/2007 |
| WO | WO2007115110 A2 | 10/2007 |
| WO | WO2007129220 A2 | 11/2007 |
| WO | WO2007133311 A2 | 11/2007 |
| WO | WO2007136820 A2 | 11/2007 |
| WO | WO2007137211 A2 | 11/2007 |
| WO | WO2007143726 A2 | 12/2007 |
| WO | WO2007144782 A2 | 12/2007 |
| WO | WO2007146784 A2 | 12/2007 |
| WO | WO2008006097 A2 | 1/2008 |
| WO | WO2008016802 A1 | 2/2008 |
| WO | WO2008026905 A2 | 3/2008 |
| WO | WO2008030873 A2 | 3/2008 |
| WO | WO2008030939 A2 | 3/2008 |
| WO | WO2008/045635 | 4/2008 |
| WO | WO2008045635 A2 | 4/2008 |
| WO | WO2008055028 A1 | 5/2008 |
| WO | WO2008/065653 | 6/2008 |
| WO | WO2008065653 A1 | 6/2008 |
| WO | WO2008069919 A2 | 6/2008 |
| WO | WO2008083484 A1 | 7/2008 |
| WO | WO2008085825 A1 | 7/2008 |
| WO | WO2008/099382 | 8/2008 |
| WO | WO2008094217 A1 | 8/2008 |
| WO | WO2008094842 A1 | 8/2008 |
| WO | WO2008099382 A1 | 8/2008 |
| WO | WO2008112437 A2 | 9/2008 |
| WO | WO2008124056 A1 | 10/2008 |
| WO | WO2008140989 A2 | 11/2008 |
| WO | WO2008157497 A2 | 12/2008 |
| WO | WO2008157777 A1 | 12/2008 |
| WO | WO2009005625 A1 | 1/2009 |
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009086446 A1 | 7/2009 |
| WO | WO2009092294 A1 | 7/2009 |
| WO | WO2009094015 A1 | 7/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |
| WO | 2011/021082 A1 | 2/2011 |
| WO | WO 2012/112565 | 8/2012 |

OTHER PUBLICATIONS

Extended European Search Report corresponding to EP 13 16 4453.6, completed Jul. 29, 2013 and mailed Aug. 5, 2013; (7 pp).
US 6,503,260, 01/2003, Schaller et al. (withdrawn)

* cited by examiner

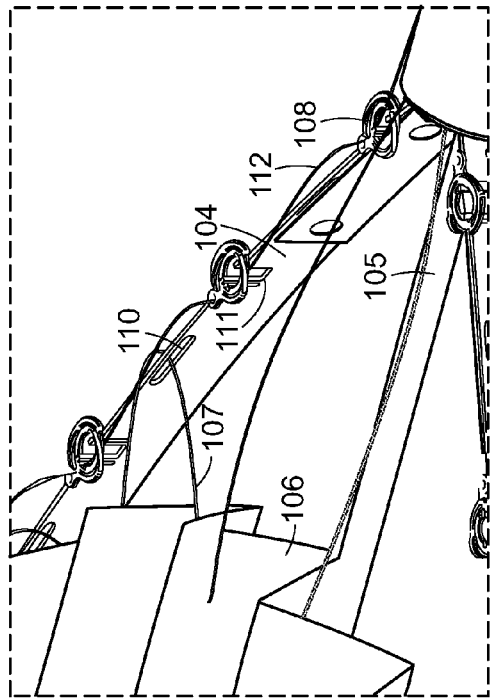
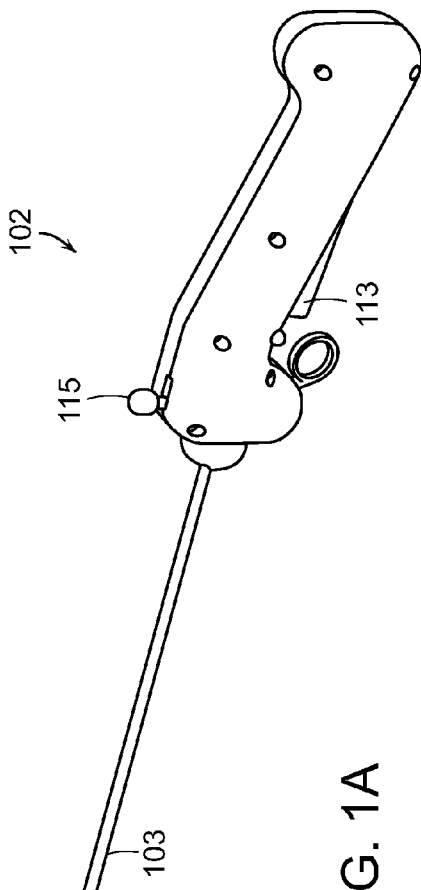
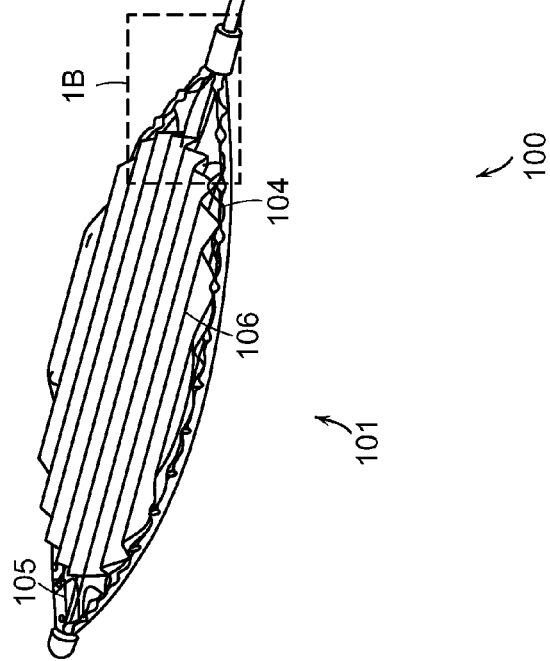
FIG. 1B
FIG. 1A

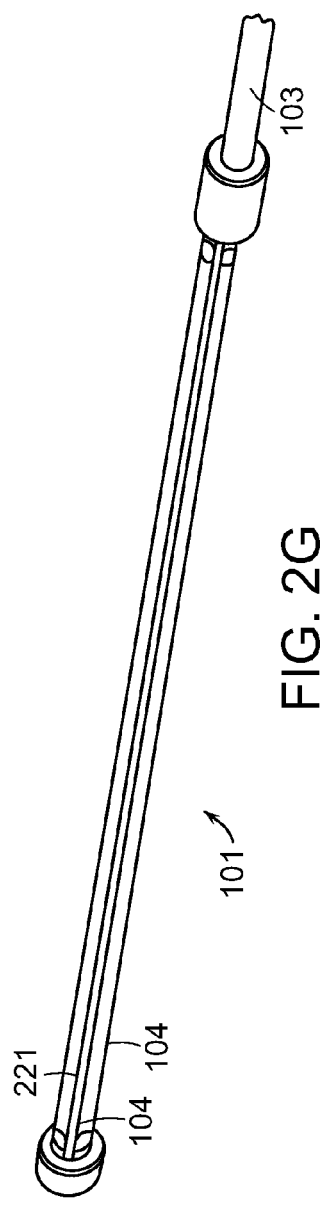
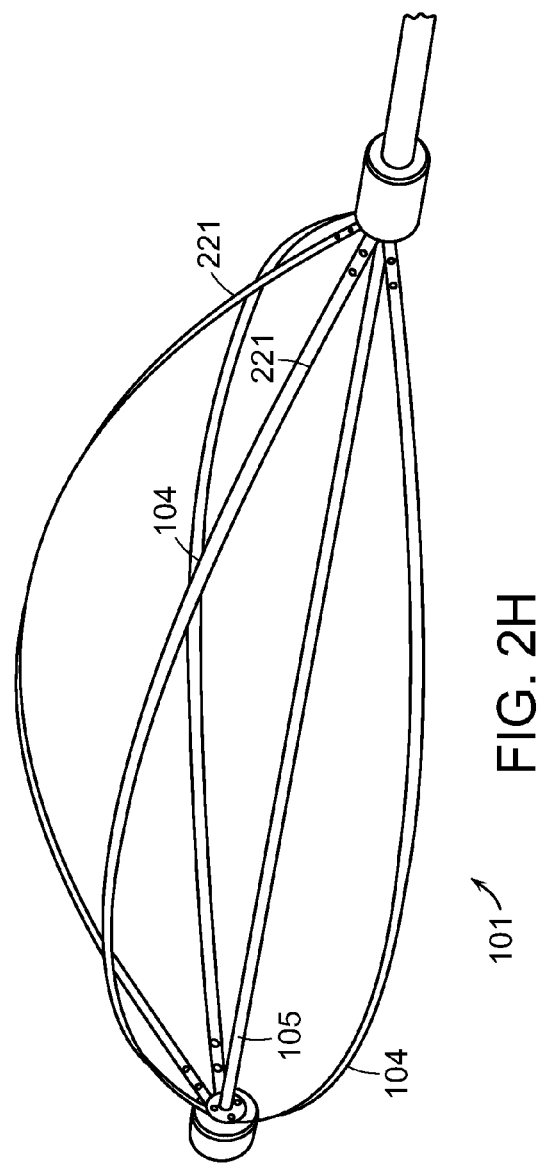

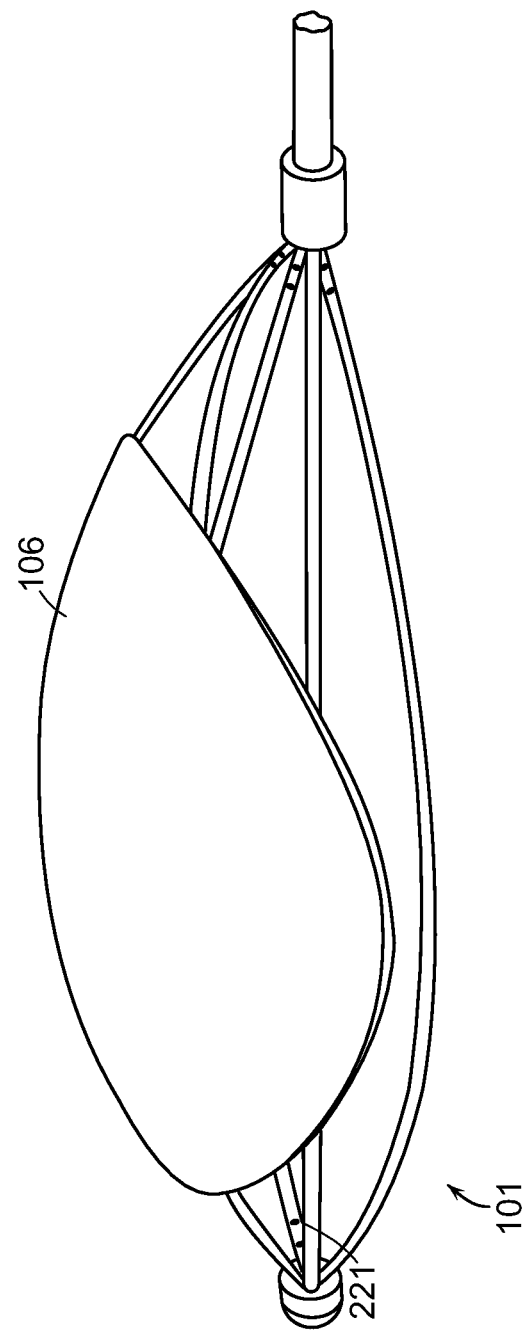

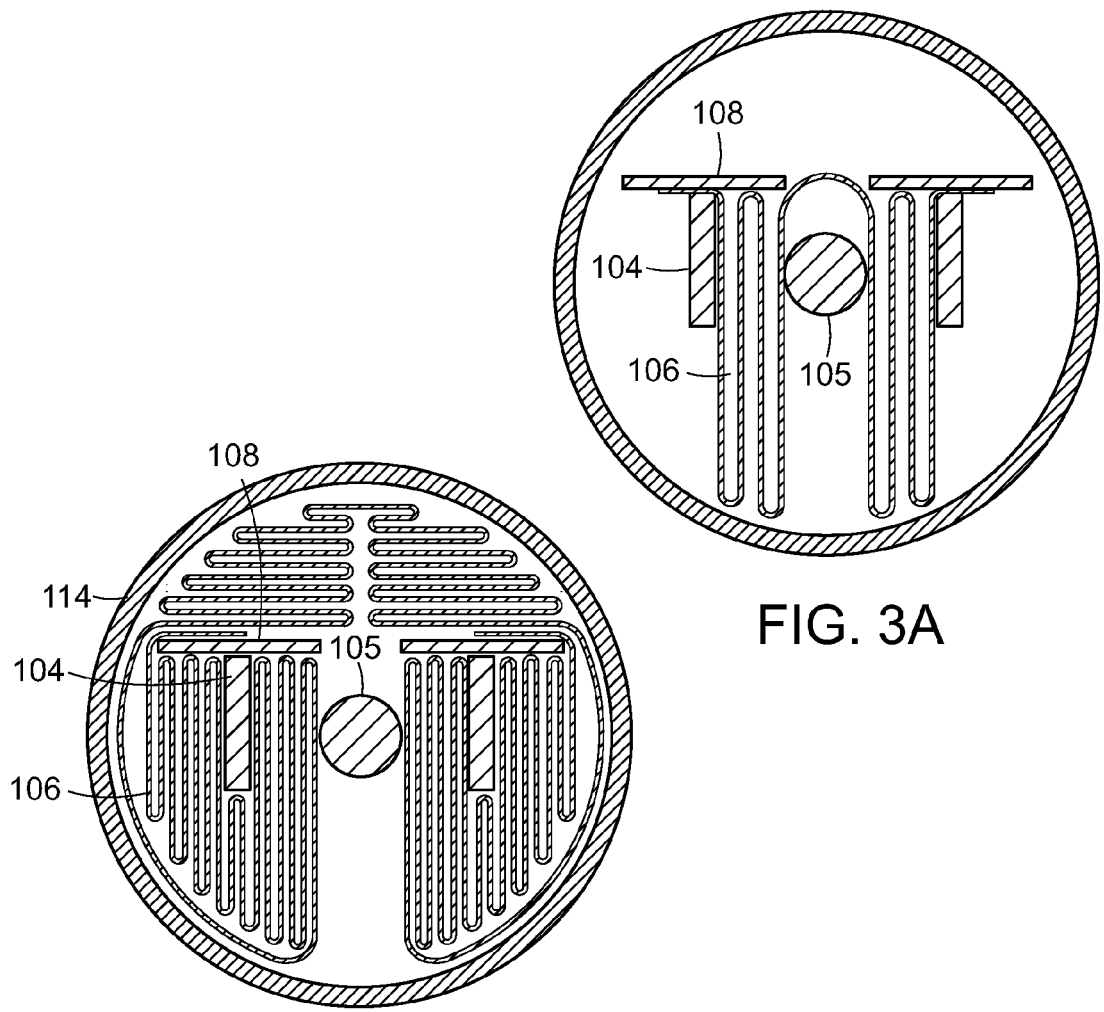
FIG. 3A
FIG. 3B
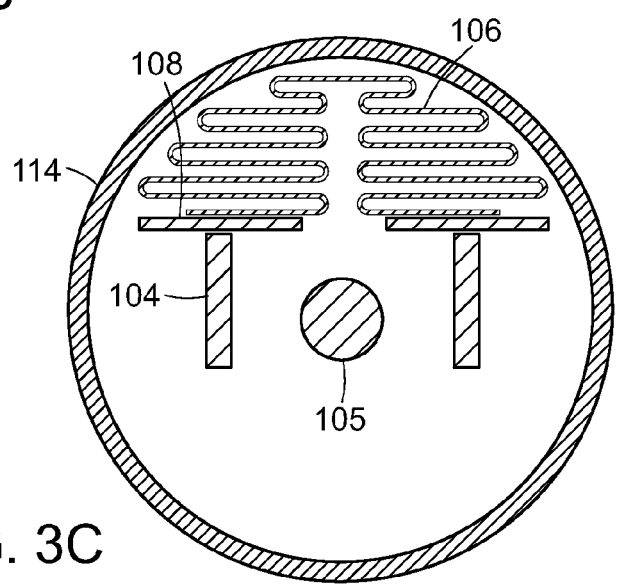
FIG. 3C

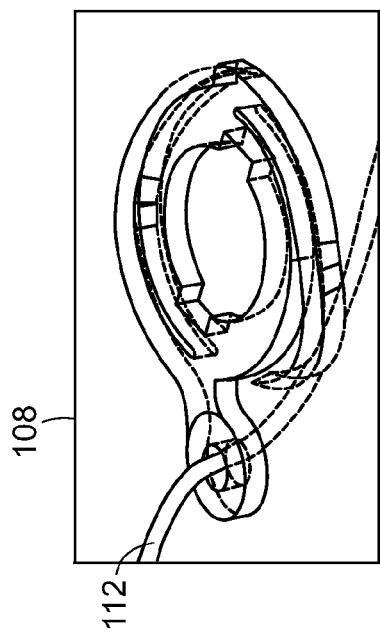
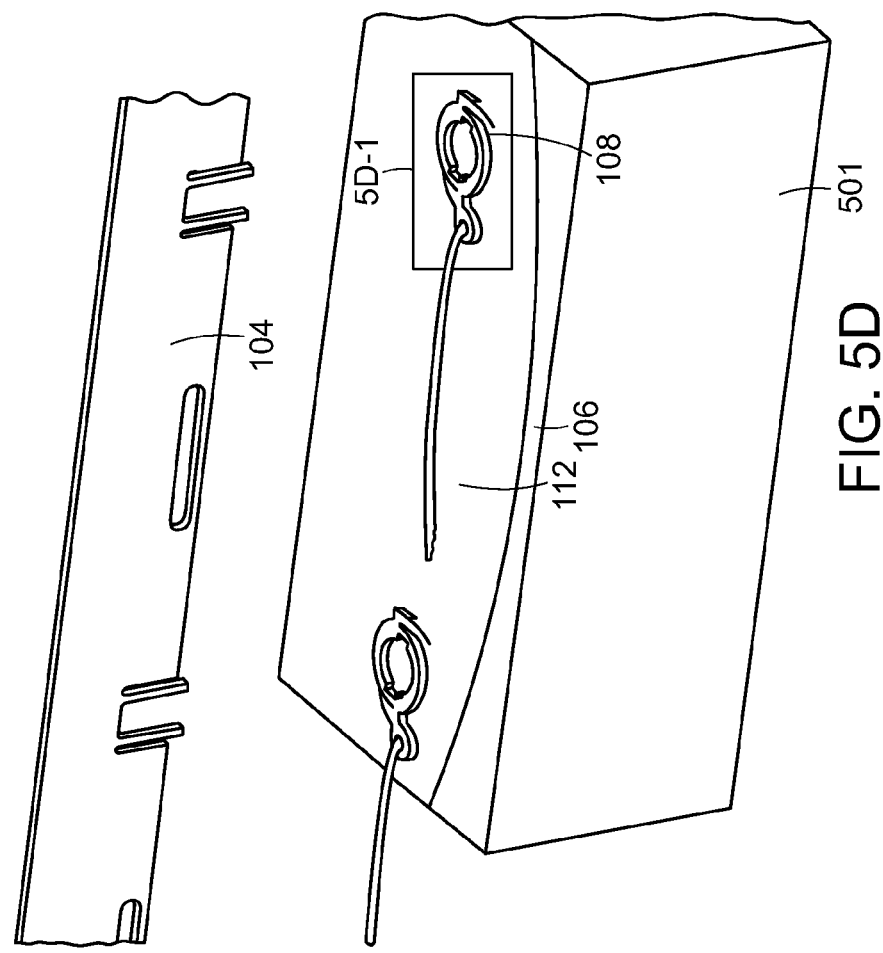

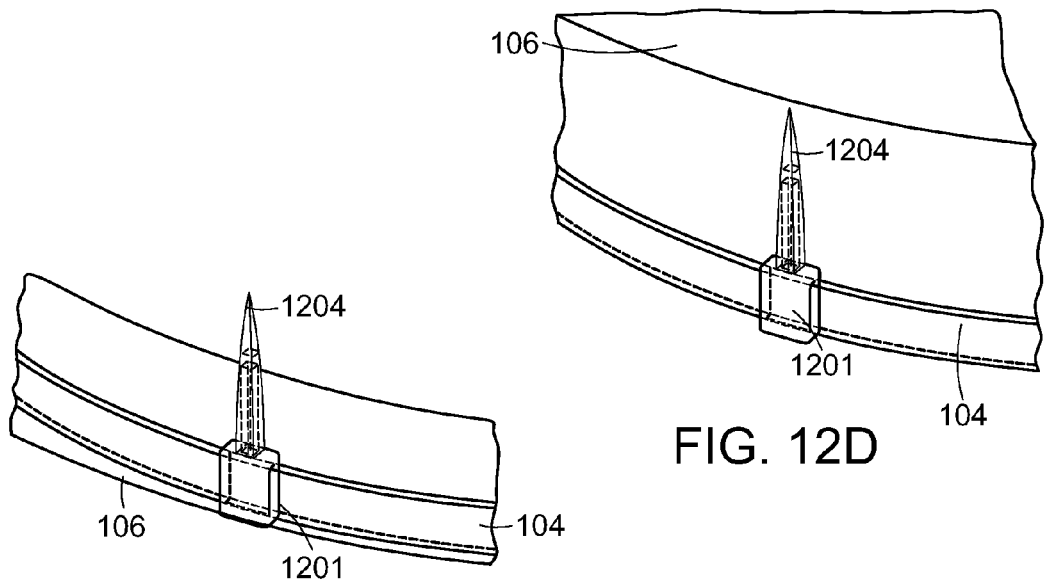
FIG. 12D
FIG. 12E
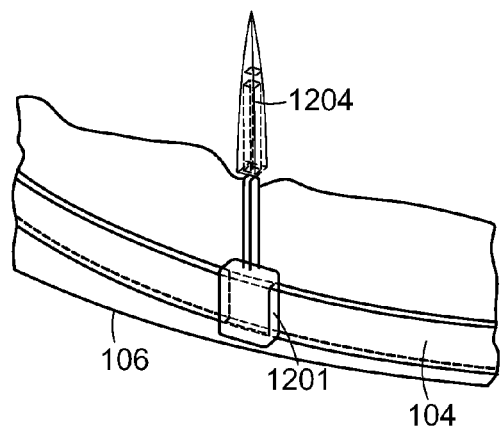
FIG. 12F
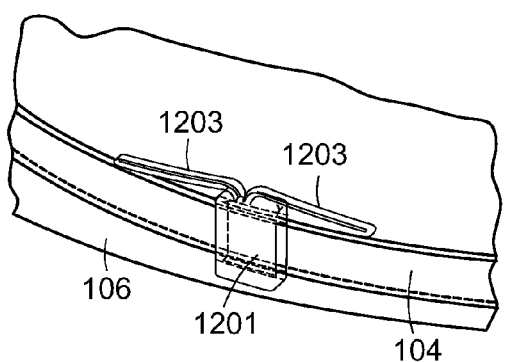
FIG. 12G

DEVICE AND METHOD FOR DEPLOYING AND ATTACHING AN IMPLANT TO A BIOLOGICAL TISSUE

RELATED APPLICATIONS

The present application is a continuation-in-part of U.S. patent application Ser. No. 12/834,456, filed Jul. 12, 2010, which is a continuation-in-part of PCT international patent application number PCT/IL2009/000188, filed Feb. 18, 2009, which claims the benefit of and priority to U.S. provisional patent application Ser. No. 61/029,386, filed Feb. 18, 2008, the content of each of which is incorporated by reference herein in its entirety.

FIELD OF THE INVENTION

This invention generally relates to a device and method for repairing an aperture in biological tissue. More specifically, the present invention relates to devices and methods for deploying and attaching an implant to a biological tissue.

BACKGROUND

An object of the present invention is to provide apparatus and a method for performing corrective surgery on internal wounds such as hernia where invasion of the patient's body tissues is minimized and resultant trauma is reduced.

A hernia is a protrusion of a tissue, structure, or part of an organ through the muscular tissue or the membrane by which it is normally contained. In other words a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first deploy the patch and then to attach the patch to the tissue.

There are many patents and patent applications relating to attaching a prosthesis implant to a tissue via tacks. Each patent and patent application describes a different attachment mechanism via different anchoring means (see for example U.S. Pat. No. 6,447,524). Traditional anchors used in surgery include clips, staples, or sutures, and may also be referred to as tissue anchors. These devices are usually made of a biocompatible material (or are coated with a biocompatible material), so that they can be safely implanted into the body. Most tissue anchors secure the tissue by impaling it with one or more posts or legs that are bent or crimped to lock the tissue into position. Thus, most traditional anchors are rigid or are inflexibly attached to the tissue. For example PCT no. WO07/021,834 describes an anchor having two curved legs that cross in a single turning direction to form a loop. Those two curved legs are adapted to penetrate tissue in a curved pathway. U.S. Pat. No. 4,485,816 (refers hereinafter as '816) describes surgical staple made of shape memory alloy. The staple is placed in contact of the tissue and then heated. The heating causes the staple to change its shape thus, penetrating the tissue.

U.S. Pat. No. 6,893,452 (refers hereinafter as '452) describes a tissue attachment device that facilitates wound healing by holding soft tissue together under improved distribution of tension and with minimal disruption of the wound interface and its nutrient supplies. The device has multiple sites for grasping the tissue using tines or prongs or other generally sharp, projecting points, protruding from a single, supportive backing. One of the embodiments described in '452 is the use of sharp projecting points protruding from the supportive backing in two different angles.

U.S. Pat. No. 6,517,584 (refers hereinafter as '584) describes a hernia patch which includes at least one anchoring device made of shape memory material. The anchoring devices are initially secured to the prosthesis by being interlaced through a web mesh constituting the prosthesis. The attachment is obtained by altering the attachment element's shape from rectilinear to a loop shape due to heat induced shape memory effect.

Yet other patent literature relates to devices for endoscopic application of surgical staples adapted to attach surgical mesh to a body tissue.

An example of such a teaching is to be found in U.S. Pat. Nos. 5,364,004, 5,662,662, 5,634,584, 5,560,224, 5,588,581 and in 5,626,587.

There are a few patent and patent applications teaching the deployment of patches. For example U.S. Pat. No. 5,836,961 (refers hereinafter as '961) which relates to an apparatus used for developing an anatomic space for laparoscopic hernia repair and a patch for use therewith. The apparatus of patent '961 comprises a tubular introducer member having a bore extending therethrough. A tunneling shaft is slidably mounted in the bore and has proximal and distal extremities including a bullet-shaped tip. A rounded tunneling member is mounted on the distal extremity of the tunneling shaft. The apparatus comprises an inflatable balloon. Means is provided on the balloon for removably securing the balloon to the tunneling shaft. Means is also provided for forming a balloon inflation lumen for inflating the balloon. The balloon is wrapped on the tunneling shaft. A sleeve substantially encloses the balloon and is carried by the tunneling shaft. The sleeve is provided with a weakened region extending longitudinally thereof, permitting the sleeve to be removed whereby the balloon can be unwrapped and inflated so that it lies generally in a plane. The balloon as it is being inflated creates forces generally perpendicular to the plane of the balloon to cause pulling apart of the tissue along a natural plane to provide the anatomic space.

Although patent '961 relates to deploying means, patent '961 teaches a device in which the patch is attached to a balloon which is introduced into the abdominal cavity. The deployment is performed by inflating the balloon. In other words, a totally different deploying means are disclosed.

Furthermore, due to the relatively large volumes of balloons several disadvantages are likely to occur: (a) The visibility within the abdominal cavity might be damaged; (b) The accessibility of the attachment means to the patch might be impaired; and, (c) The maneuverability of the patch within the abdominal cavity is limited.

Yet more, another major drawback to patent '961, the inflated balloon lacks any mechanical stiffness which is needed for navigation of the patch to its position.

Another example for deploying the patch can be found in U.S. Pat. No. 5,370,650 (refers hereinafter as '650) which relates to an apparatus for positioning surgical implants adjacent to body tissue to facilitate the fastening of the implant to the body tissue. Patent '650 provides an apparatus for positioning surgical implants adjacent to body tissue, comprising an outer tube having a proximal end, a distal end and a longitudinal axis; an inner rod at least partially disposed within the outer tube and slidable along said longitudinal axis. The inner rod has a proximal and a distal end portions. The inner rod distal end portion further comprises articulating means for pivoting at an angle with respect to the longitudinal axis. A looped support member having first and second end portions fixedly secured to said distal end portion of the inner rod; and a surgical implant releasably secured to the looped support member (a preferred embodiment illustrating the teaching of patent '650 is illustrated in FIG. 17).

The major difference between patent '650 and the present invention is the actual patch deployment mechanism.

While in patent '650, the looped support member 14 is transferred from a deployed configuration to a retracted configuration by pushing and pulling tube 12, in the proposed technology the flexible arms are reconfigured from their initial stage (IS) to their final stage (FS) by the reciprocal movement the central shaft. In other words, while in patent '650, the patch is deployed due to the elasticity of the loop member (no force is applied), in the present application, the patch is deployed by actively and directly applying force on the Flexible arms by the surgeon.

Furthermore, the deployment of the patch in patent '650 is passive and unidirectional; i.e., once the patch is deployed by pulling tube 12, the patch can not be un-deployed and reinserted into tube 12. In order to reinsert the patch into tube 12, the patch must be refolded and such an action can not be performed while the patch is within the patient. Therefore, the surgeon has only one chance to unfold the patch. This is in sharp contrary to the present invention in which the deployment of the patch is bidirectional and actively controlled such that the patch can be deployed and un-deployed simply by the reconfiguration of the flexible arms (which a full description will be provided in the detail description).

Yet another major distinction between patent '650 and the proposed invention is the fact that in patent '650 the looped support member 14 is preferably in a deployed (i.e., open) configuration thereby insertion of the looped support member 14 into tube 12 will require the physician to apply a significant amount of force in order to maintain the looped support member 14 in a closed configuration. On the contrary, in the present invention, the flexible arms can be actively configured to be constantly closed without any additional force applied by the physician. Therefore, the insertion of the device through a trocar is facilitated.

Yet more, the present invention comprises a central shaft for providing the device mechanical stiffness for the backbone of the system which is needed for better positioning of the patch within the body. Further, by providing mechanical stiffness to the backbone of the system, it will enable the detachment of the patch from the deployment system. Such a mechanism is not disclosed nor claimed in patent '650.

Lastly, patent '650 describes no attachment mechanism for attaching the patch to the tissue. Further, some major, non obvious modification will have to be made in order to enable attachment between the patch and the tissue whilst using the device of patent '650.

More patent literature can be found in PCT no. WO08065653 (refers hereinafter as '653) relates to a device especially adapted to deploy a patch within a body cavity. The device is an elongate open-bored applicator (EOBP) and comprises (a) at least one inflatable contour-balloon, (b) at least one inflatable dissection balloon. The inflatable contour-balloon and the inflatable dissection balloon are adjustable and located at the distal portion. The EOBP additionally comprises (c) at least one actuating means located at the proximal portion. The actuating means is in communication with the inflatable contour-balloon and the inflatable dissection balloon. The actuating means is adapted to provide the inflatable contour-balloon and the inflatable dissection balloon with independent activation and/or de-activation.

It should be pointed out that PCT '653 does not disclose nor claim means adapted to anchor the patch to the biological tissue.

Like patent '961, the deployment system describes in PCT '653 is an inflated one, thus it is fundamentally different from the proposed invention.

All those patent and patent application demonstrate attachment means for attaching the patch to the tissue or means for deploying the patch within the body. However none of the literature found relates to a device especially adapted to deploy and attached a patch to a biological tissue.

Thus, there is still a long felt need for a device that can be used for both deploying and attaching a patch to a biological tissue.

Furthermore, there is still a long felt need for a deployment system that will overcome the above mentioned drawbacks and will provide a deployment system that will enable the following (i) a reversible deployment of the patch (i.e., enable the folding and the unfolding of said patch); (ii) a controlled deployment of the patch (i.e., the surgeon applies force in order to deploy the patch and therefore the deployment is actively controlled); and, (iii) will provide mechanical stiffness for the backbone of the system.

SUMMARY OF THE INVENTION

It is one object of the present invention to provide an integrated deployment and attachment device (DAD) comprising means adapted to deploy a patch and means adapted to attach said patch to a biological tissue within the body; wherein said DAD is adapted to sequentially deploy said patch within said body and attach said patch to said biological tissue within said body; further wherein said deployment of said patch is (i) controlled such that a continuous deployment is obtained; and, (ii) bidirectional such that said deployment is fully reversible.

It is another object of the present invention to provide the DAD as defined above, wherein said DAD is characterized by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) are adapted to be reversibly coupled to said patch; said FA having a proximal end (FAP) jointly connected to said TD, and a distal end (FAD) jointly connected to said CSD; said FA (104) are characterized by having an initial stage (IS) at which said FA (104) are straight and parallel to the longitudinal axis of said central shaft (105); and, a final stage (FS) at which said FA (104) are laterally curved with respect to said longitudinal axis of said central shaft (105) such that said patch is deployed; said FA are adapted to reversibly transform from said IS to said FS by said reciprocate movement of said central shaft (105) towards and away from said proximal portion such that said deployment of said patch is bidirectional;

said FA (104) comprises (a) at least one attachment clip (108) adapted to attach said patch (106) to said biological tissue (501); and, (b) at least one connecting means adapted to at least partially reversibly connect said patch (106) to said FA (104);

said proximal portion comprising at least one handle (102) located outside said body; said handle is adapted to (i) reversibly transform said FA from said IS to said FS; (ii) activate said clip (108) such that said patch (106) is at least partially attached to said tissue; and, (iii) release said patch from said FA.

It is another object of the present invention to provide the DAD as defined above, wherein said connecting means are selected from at least one dedicated loop and\or stretching means (107) or patch-FA clip (1201) adapted to reversibly connect said patch to said FA.

It is another object of the present invention to provide the DAD as defined above, wherein said clip is adapted to attach said patch to said biological tissue whilst simultaneously detaching from said FA.

It is another object of the present invention to provide the DAD as defined above, wherein said clip is adapted to first attach said patch to said biological tissue and then to detach from said FA.

It is another object of the present invention to provide the DAD as defined above, wherein said clip is characterized by having: (i) main portion (403) adapted to at least partially reversibly connected to said FA; (ii) at least one hooks (402) connected to said main portion, adapted to at least partially penetrate through said patch (106) to said tissue (501) such that an attachment between said patch and said tissue is obtained; (iii) a portion (404) adapted to reversibly connect to activation means; said activation means are adapted to actuate said hooks (402) such that said attachment is obtained.

It is another object of the present invention to provide the DAD as defined above, wherein said clip additionally comprises securing means (701, 702) adapted to secure and fix said clip within said tissue and said patch.

It is another object of the present invention to provide the DAD as defined above, wherein said stretching means (107) and said activation means are selected from a group consisting of a wire.

It is another object of the present invention to provide the DAD as defined above, wherein said attachment between said patch and said tissue is obtained by a radial motion of said clip followed by a linear motion of said wire.

It is another object of the present invention to provide the DAD as defined above, wherein said attachment between said patch and said tissue is obtained by a linear motion of said clip followed by a linear motion of said wire.

It is another object of the present invention to provide the DAD as defined above, wherein said activation means is activation wire (112).

It is another object of the present invention to provide the DAD as defined above, wherein said activation wire (112) and/or said stretching wire 107 is made from a group consisting of biocompatible metal, shape memory materials, super elastic metals, non-degradable polymer and degradable polymers.

It is another object of the present invention to provide the DAD as defined above, wherein said clip is made from a group consisting of biocompatible metal, shape memory materials, super elastic metals, non-degradable polymer and degradable polymers.

It is another object of the present invention to provide the DAD as defined above, especially adapted to be used in procedures selected from a group consisting of hernia surgeries, minimal invasive heart surgeries, endoscopic colon surgeries.

It is another object of the present invention to provide the DAD as defined above, additionally comprising a cutting mechanism adapted to cut said stretching means (107) in at least one location such that said patch and said FA's are detached.

It is another object of the present invention to provide the DAD as defined above, wherein the detachment between said patch and said FA's is obtained by means selected from a group consisting of transforming said FA's from said FS to said IS; mechanically moving said DAD away from said patch.

It is another object of the present invention to provide the DAD as defined above, wherein said patch-FA clips (1201) comprises a body 1202 and at least one branch 1203 at least partially protruding out of said body; said patch-FA clip 1201 is characterized by (i) a main longitudinal axis along which a reciprocal motion of said body 1203 is enabled; (ii) at least two positions enabled by said reciprocal motion; a first position in which said branch 1203 is perpendicular to the patch and a second position in which said branch 1203 is parallel to said patch.

It is another object of the present invention to provide the DAD as defined above, wherein said patch-FA clips (1201) comprises (i) a body 1202; (ii) at least one branch 1203 coupled to said body and at least partially protruding out of said body; and, (iii) at least one envelope covering (1204) at least partially covering said branch (1203); said patch-FA clip 1201 is characterized by at least two positions; a first position in which said branch 1203 is housed within said envelope covering (1204) and perpendicular to the patch and a second position in which said envelope covering (1204) is removed and said branch 1203 is parallel to said patch.

It is another object of the present invention to provide the DAD as defined above, additionally comprising means (1501 and 1502) adapted to laterally rotate said patch with respect to said tissue, such that the right orientation of said patch is obtained.

It is another object of the present invention to provide the DAD as defined above, additionally comprising at least one sleeve adapted to at least partially reversibly cover said patch such that insertion of said distal end into said patient through a trocar is facilitated.

It is another object of the present invention to provide the DAD as defined above, wherein said sleeve additionally comprising at least one stopper positioned at the distal end of said stopper, said stopper is adapted to prevent said sleeve from insertion into said patient.

It is another object of the present invention to provide a method for deploying and attaching a patch to a biological tissue. The method comprises steps selected inter alia from:

a. obtaining a integrated deployment and attachment device (DAD); said DAD is characterized by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) having a proximal end (FAP) jointly connected to said TD, and a distal end (FAD) jointly connected to said CSD; said FA (104) are characterized by having an initial stage (IS) at which said FA (104) are straight and parallel to the longitudinal axis of said central shaft (105); and, a final stage (FS) at which said FA (104) are laterally curved with respect to said longitudinal axis of said central shaft (105) such that said patch is deployed; said FA are adapted to reversibly transform from said IS to said FS by said reciprocate movement of said central shaft (105) towards and away from said proximal portion;

said FA (104) comprises (a) at least one attachment clip (108) adapted to attach said patch (106) to said biological tissue (501); and, (b) at least one connecting means adapted to at least partially reversibly connect said patch (106) to said FA (104);

said proximal portion comprising at least one handle (102) located outside said body; said handle is adapted to (i) reversibly transform said FA from said IS to said FS; (ii) activate said clip (108) such that said patch (106) is at least partially attached to said tissue; and, (iii) release said patch from said FA.

b. introducing said distal portion into said body cavity;
c. reversibly transforming said FA from said IS to said FS; thereby deploying said patch;
d. adjacently bringing said patch into contact with said biological tissue;
e. activating said at least one clip, thereby attaching said patch to said tissue;
f. detaching said at least one clip from said FA;
g. detaching said patch from said FA;
h. transforming said FA from said FS to said IS; and,
i. extracting said DAD from said body cavity.

It is another object of the present invention to provide the method as defined above, wherein said step of reversibly transforming said FA from said IS to said FS provides a controlled continuous deployment of said patch.

It is another object of the present invention to provide the method as defined above, wherein said step of reversibly transforming said FA from said IS to said FS provides a bidirectional fully reversible deployment.

It is another object of the present invention to provide the method as defined above, wherein said steps of detaching said patch from said FA and transforming said FA from said FS to said IS are performed simultaneously.

It is another object of the present invention to provide the method as defined above, wherein said step of detaching said patch from said FA is performed by said step of transforming said FA from said FS to said IS.

It is another object of the present invention to provide the method as defined above, wherein said step of detaching said patch from said FA is performed by mechanically moving said DAD from said patch.

It is another object of the present invention to provide the method as defined above, wherein said steps of activating said clip and detaching said clip from said FA are performed simultaneously.

It is another object of the present invention to provide the method as defined above, wherein said step of activating said clip additionally comprising step of either linearly moving and/or radically rotating said clip.

It is another object of the present invention to provide the method as defined above, wherein said step of detaching said patch from said FA comprising steps of cutting said connecting means at least one end; and, withdrawing said connecting means from the second end.

It is another object of the present invention to provide the method as defined above, additionally comprising the step of selecting said connecting means from a group consisting of biocompatible metal, shape memory materials, super elastic metals, non-degradable polymer and degradable polymers.

It is another object of the present invention to provide the method as defined above, additionally comprising the step of selecting said clip from a group consisting of biocompatible metal, shape memory materials, super elastic metals, non-degradable polymer and degradable polymers.

It is another object of the present invention to provide the method as defined above, additionally comprising a second step of attaching said patch to said biological tissue using conventional attaching means.

It is another object of the present invention to provide the method as defined above, additionally comprising step of reversibly attaching said patch to said FA.

It is another object of the present invention to provide the method as defined above, additionally comprising step of laterally rotating said patch with respect to said tissue, such that the right orientation of said patch is obtained.

It is another object of the present invention to provide the method as defined above, additionally comprising step of at least partially covering said patch such that insertion of said distal end into said patient through a trocar is facilitated.

It is another object of the present invention to provide the method as defined above, additionally comprising step of preventing said sleeve additionally form inserting into said patient by means of at least one stopper.

It is another object of the present invention to provide a clip especially adapted to attach a patch to a biological tissue; said clip comprises (i) at least one hook adapted to at least partially penetrate through said patch to said biological tissue such that an attachment between said patch and said tissue is obtained; (ii) a portion adapted to at least partially reversibly connect to activation means; said activation means are adapted to actuate said hooks such that said attachment is obtained;

wherein said clip is actuated and said attachment is obtained by a linear motion of said activation means.

It is another object of the present invention to provide the clip as defined above, wherein said linear motion of said activation means is adapted to be converted into a motion selected from a group consisting of rotational motion, radial motion or linear motion of said clip; said motion of said clip is adapted to provide said attachment between said patch and said tissue via penetration of said at least one hook into said tissue.

It is another object of the present invention to provide the clip as defined above, additionally comprises securing means adapted to secure and fix said clip within said tissue and said patch.

It is another object of the present invention to provide the clip as defined above, wherein said clip is made from a group consisting of biocompatible metal, shape memory materials, super elastic metals, non-degradable polymer and degradable polymers.

It is another object of the present invention to provide the DAD as defined above, wherein said DAD is characterized by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) having a proximal end (FAP) jointly connected to said TD, and a distal end (FAD) jointly connected to said CSD; said FA (104) are characterized by having an initial stage (IS) at which said FA (104) are straight and parallel to the longitudinal axis of said central shaft (105); and, a final stage (FS) at which said FA (104) are laterally curved with respect to said longitudinal axis of said central shaft (105) such that said patch is deployed; said FA are adapted to reversibly transform from said IS to said FS by said reciprocate movement of said central shaft (105) towards and away from said proximal portion, such that (i) a controlled and continuous deployment is obtained; and, (ii) bidirectional, fully reversible deployment is obtained;

said FA comprises (a) at least one connecting means adapted to at least partially reversibly connect said patch (106) to said FA (104);

said patch is coupled to at least one clip; said clip is adapted to attach said patch (106) to said biological tissue (501);

said proximal portion comprising at least one handle (102) located outside said body; said handle is adapted to (i) reversibly transform said FA from said IS to said FS; (ii) activate said clip (108) such that said patch (106) is at least partially attached to said tissue; and, (iii) release said patch from said FA.

It is another object of the present invention to provide the DAD as defined above, wherein said connecting means are selected from at least one dedicated loop and stretching means (107) or patch-FA clip 1201 adapted to reversibly connect said patch to said FA.

It is another object of the present invention to provide the DAD as defined above, wherein said patch-FA clips 1201 comprises a body 1202 and at least one branch 1203 at least partially protruding out of said body; said patch-FA clip 1201 is characterized by (i) a main longitudinal axis along which a reciprocal motion of said body 1203 is enabled; (ii) at least two positions enabled by said reciprocal motion; a first position in which said branch 1203 is perpendicular to the patch and a second position in which said branch 1203 is parallel to said patch.

It is another object of the present invention to provide the DAD as defined above, wherein said patch-FA clips (1201) comprises (i) a body 1202; (ii) at least one branch 1203 coupled to said body and at least partially protruding out of said body; and, (iii) at least one envelope covering (1204) at least partially covering said branch (1203); said patch-FA clip 1201 is characterized by at least two positions; a first position in which said branch 1203 is housed within said envelope covering (1204) and perpendicular to the patch and a second position in which said envelope covering (1204) is removed and said branch 1203 is parallel to said patch.

It is another object of the present invention to provide a patch especially adapted to be connected to a biological tissue; wherein said patch is connected to at least one clip adapted to attaché said patch to said biological tissue.

It is another object of the present invention to provide a deployment device (DD) adapted to deploy a patch within a body cavity; wherein said DD is characterize by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) are adapted to be reversibly coupled to said patch; said FA having a proximal end (FAP) jointly connected to said TD, and a distal end (FAD) jointly connected to said CSD; said FA (104) are characterized by having an initial stage (IS) at which said FA (104) are straight and parallel to the longitudinal axis of said central shaft (105); and, a final stage (FS) at which said FA (104) are laterally curved with respect to said longitudinal axis of said central shaft (105) such that said patch is deployed; said FA are adapted to reversibly transform from said IS to said FS by said reciprocate movement of said central shaft (105) towards and away from said proximal portion;

said FA comprises at least one connecting means adapted to at least partially reversibly connect said patch (106) to said FA (104);

said proximal portion comprising at least one handle (102) located outside said body; said handle is adapted to (i) reversibly transform said FA from said IS to said FS; and, (ii) release said patch from said FA;

wherein said deployment of said patch is (i) controlled such that a continuous deployment is obtained; and, (ii) bidirectional such that said deployment is fully reversible.

It is another object of the present invention to provide the DD as defined above, wherein said connecting means are selected from at least one dedicated loop and stretching means (107) or patch-FA clip 1201 adapted to reversibly connect said patch to said FA.

It is another object of the present invention to provide the DD as defined above, wherein said patch-FA clips 1201 comprises a body 1202 and at least one branch 1203 at least partially protruding out of said body; said patch-FA clip 1201 is characterized by (i) a main longitudinal axis along which a reciprocal motion of said body 1203 is enabled; (ii) at least two positions enabled by said reciprocal motion; a first position in which said branch 1203 is perpendicular to the patch and a second position in which said branch 1203 is parallel to said patch.

It is another object of the present invention to provide the DD as defined above, wherein said patch-FA clips (1201) comprises (i) a body 1202; (ii) at least one branch 1203 coupled to said body and at least partially protruding out of said body; and, (iii) at least one envelope covering (1204) at least partially covering said branch (1203); said patch-FA clip 1201 is characterized by at least two positions; a first position in which said branch 1203 is housed within said envelope covering (1204) and perpendicular to the patch and a second position in which said envelope covering (1204) is removed and said branch 1203 is parallel to said patch.

It is another object of the present invention to provide the DD as defined above, wherein said stretching means are selected from a group consisting of a wire.

It is another object of the present invention to provide the DD as defined above, wherein said stretching wire 107 is made from a group consisting of biocompatible metal, shape memory materials, super elastic metals, non-degradable polymer and degradable polymers.

It is another object of the present invention to provide the DD as defined above, additionally comprising a cutting mechanism adapted to cut said stretching means (107) such that said patch and said FA's are detached.

It is another object of the present invention to provide the DD as defined above, wherein the detachment between said patch and said FA's is obtained by means selected from a group consisting of transforming said FA's from said FS to said IS; mechanically moving said DAD away from said patch.

It is another object of the present invention to provide the DD as defined above, especially adapted to hernia surgeries.

It is another object of the present invention to provide the DD as defined above, additionally comprising means (1501 and 1502) adapted to laterally rotate said patch with respect to said tissue, such that the right orientation of said patch is obtained.

It is another object of the present invention to provide the DD as defined above, additionally comprising at least one sleeve at least partially covering said patch such that insertion of said distal end into said patient through a trocar is facilitated.

It is another object of the present invention to provide the DD as defined above, wherein said sleeve additionally comprising a stopper positioned at the distal end of said stopper, said stopper is adapted to prevent said sleeve from insertion into said patient.

It is another object of the present invention to provide a method for deploying within a body cavity. The method comprises steps selected inter alia from:

a. obtaining a deployment device characterize by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) having a proximal end (FAP) jointly connected to said TD, and a distal end (FAD) jointly connected to said CSD; said FA (104) are characterized by having an initial stage (IS) at which said FA (104) are straight and parallel to the longitudinal axis of said central shaft (105); and, a final stage (FS) at which said FA (104) are laterally curved with respect to said longitudinal axis of said central shaft (105) such that said patch is deployed; said FA are adapted to reversibly transform from said IS to said FS by said reciprocate movement of said central shaft (105) towards and away from said proximal portion;

said FA comprises at least one connecting means adapted to at least partially reversibly connect said patch (106) to said FA (104);

said proximal portion comprising at least one handle (102) located outside said body; said handle is adapted to (i) reversibly transform said FA from said IS to said FS; and, (ii) release said patch from said FA;

b. inserting said distal portion into said body cavity;
c. reversibly transforming said FA from said IS to said FS; thereby deploying said patch;
d. detaching said patch from said FA;
e. transforming said FA from said FS to said IS; and,
f. extracting said DAD from said body cavity.

It is another object of the present invention to provide the method as defined above, wherein said step of reversibly transforming said FA from said IS to said FS provides a controlled continuous deployment of said patch.

It is another object of the present invention to provide the method as defined above, wherein said step of reversibly transforming said FA from said IS to said FS provides a bidirectional fully reversible deployment.

It is another object of the present invention to provide the method as defined above, wherein said step of detaching said patch from said FA comprising steps of cutting said connecting means in at least one end; and, withdrawing said connecting means from the second end.

It is another object of the present invention to provide the method as defined above, additionally comprising the step of selecting said connecting means from a group consisting of biocompatible metal, shape memory materials, super elastic metals, non-degradable polymer and degradable polymers.

It is another object of the present invention to provide the method as defined above, additionally comprising a second step of attaching said patch to said biological tissue using conventional attaching means.

It is another object of the present invention to provide the method as defined above, additionally comprising step of reversibly attaching said patch to said FA.

It is another object of the present invention to provide the method as defined above, wherein said steps of detaching said patch from said FA and transforming said FA from said FS to said IS are performed simultaneously.

It is another object of the present invention to provide the method as defined above, wherein said step of detaching said patch from said FA is performed by said step of transforming said FA from said FS to said IS.

It is another object of the present invention to provide the method as defined above, wherein said step of detaching said patch from said FA is performed by mechanically moving said DAD from said patch.

It is another object of the present invention to provide the method as defined above, additionally comprising step of laterally rotating said patch with respect to said tissue, such that the right orientation of said patch is obtained.

It is another object of the present invention to provide the method as defined above, additionally comprising step of at least partially covering said patch such that insertion of said distal end into said patient through a trocar is facilitated.

It is another object of the present invention to provide the method as defined above, additionally comprising step of preventing said sleeve from inserting into said patient by means of at least one stopper.

It is another object of the present invention to provide a deployment device (DD) adapted to deploy a patch within a body cavity; wherein said DD is characterize by having a distal portion, adapted to be inserted into a body and a proximal portion, located adjacent to a user; said distal portion and said proximal portion are interconnected along a main longitudinal axis via a tube (103); said tube having a proximal end (TP) connected to said proximal portion, and a distal end (TD); said tube accommodates at least a portion of a central shaft (105); said central shaft (105) has a proximal end (CSP) accommodated within said tube (103) and a distal end (CSD) protruding from said TD end; said central shaft (105) is adapted to reciprocally move parallel to said main longitudinal axis within said tube (103);

said distal portion comprises: (i) at least two flexible arm (FA) (104) having a proximal end (FAP) jointly connected to said TD, and a distal end (FAD) jointly connected to said CSD; each of said FA (104) comprises at least two portions jointly coupled together; said FA (104) are characterized by having an initial stage (IS) at which said FA (104) are straight and parallel to the longitudinal axis of said central shaft (105); and, a final stage (FS) at which said FA (104) are perpendicular with respect to said longitudinal axis of said central shaft (105); said FA are adapted to reversibly transform from said IS to said FS by said reciprocate movement of said central shaft (105) and via said joint towards and away from said proximal portion;

said FA comprises at least one extension (1801) comprises at least one connecting means adapted to at least partially reversibly connect said patch (106) to said extension (1801);

said proximal portion comprising at least one handle (102) located outside said body; said handle is adapted to (i) reversibly transform said FA from said IS to said FS; and, (ii) release said patch from said FA;

wherein said deployment of said patch is (i) controlled such that a continuous deployment is obtained; and, (ii) bidirectional such that said deployment is fully reversible.

It is another object of the present invention to provide the DD as defined above, wherein said connecting means are selected from at least one dedicated loop and stretching means (107) or patch-FA clip 1201 adapted to reversibly connect said patch to said FA.

It is another object of the present invention to provide the DD as defined above, wherein said patch-FA clips 1201 comprises a body 1202 and at least one branch 1203 at least partially protruding out of said body; said patch-FA clip 1201 is characterized by (i) a main longitudinal axis along which a reciprocal motion of said body 1203 is enabled; (ii) at least two positions enabled by said reciprocal motion; a first position in which said branch 1203 is perpendicular to the patch and a second position in which said branch 1203 is parallel to said patch.

It is another object of the present invention to provide the DD as defined above, wherein said patch-FA clips (1201) comprises (i) a body 1202; (ii) at least one branch 1203 coupled to said body and at least partially protruding out of said body; and, (iii) at least one envelope covering (1204) at least partially covering said branch (1203); said patch-FA clip 1201 is characterized by at least two positions; a first position in which said branch 1203 is housed within said envelope covering (1204) and perpendicular to the patch and a second position in which said envelope covering (1204) is removed and said branch 1203 is parallel to said patch.

It is another object of the present invention to provide the DD as defined above, wherein said stretching means are selected from a group consisting of a wire.

It is another object of the present invention to provide the DD as defined above, wherein said stretching wire 107 is made from a group consisting of biocompatible metal, shape memory materials, super elastic metals, non-degradable polymer and degradable polymers.

It is another object of the present invention to provide the DD as defined above, wherein the detachment between said patch and said FA's is obtained by means selected from a group consisting of transforming said FA's from said FS to said IS; mechanically moving said DAD away from said patch.

It is another object of the present invention to provide the DD as defined above, especially adapted to hernia surgeries.

It is another object of the present invention to provide the DD as defined above, additionally comprising means (1501 and 1502) adapted to laterally rotate said patch with respect to said tissue, such that the right orientation of said patch is obtained.

It is still another object of the present invention to provide the DD as defined above, additionally comprising at least one sleeve at least partially covering said patch such that insertion of said distal end into said patient through a trocar is facilitated.

It is lastly an object of the present invention to provide the DD as defined above, wherein said sleeve additionally comprising a stopper positioned at the distal end of said stopper, said stopper is adapted to prevent said sleeve from insertion into said patient.

BRIEF DESCRIPTION OF THE DRAWINGS

The invention is herein described, by way of example only, with reference to the accompanying drawings, wherein:

FIGS. 1a and 1b is a schematic diagram showing a device which is a preferred embodiment of the present invention.

FIGS. 2G-2I illustrate the distal portion 101 of device 100 in a 3D configuration.

FIGS. 3A-3C illustrate a number of options for the folding of patch 106 prior to inserting the distal end 101 to the body.

FIGS. 5A-5D illustrate the attachment between a patch 106 and a tissue 501.

FIGS. 11 and 12A-12G illustrate different coupling (connecting) means between the patch 106 and the FAs 104 (i.e., the patch-FA clips 1201).

DETAIL DESCRIPTION OF THE SPECIFIC EMBODIMENTS

Figure 2A:
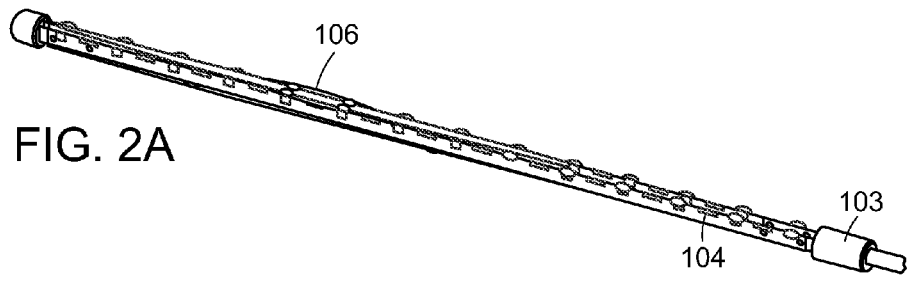
FIGS. 2A-2D which illustrate the patch deployment process.
Figure 2B:
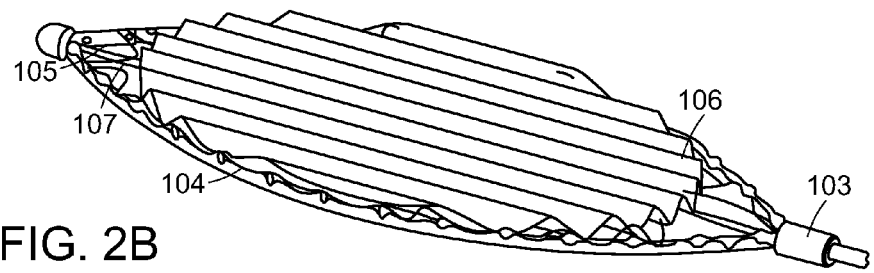

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides a device and method for deploying and attaching a patch to a biological tissue.

The present provides a deployment and attachment device (DAD) wherein the DAD is adapted to both deploy a patch within the body and to attach the patch to a biological tissue within the body.

It should be emphasized that the DAD is adapted to sequentially deploy said patch within said body and attach said patch to said biological tissue within said body, such that the deployment of said patch is (i) controlled so as a continuous deployment is obtained; and, (ii) bidirectional so as said deployment is fully reversible.

The present invention also provides a method for deploying and attaching a patch to a biological tissue. The method comprises steps selected inter alia from:
a. obtaining a DAD;
b. inserting the distal portion into the body cavity;
c. reversibly transforming the FA from the IS to the FS; thereby deploying the patch;
d. adjacently bringing the patch into contact with the biological tissue;
e. activating the clip, thereby attaching the patch to the tissue;
f. detaching the clip from the FA;
g. detaching the patch from the FA;
h. transforming the FA from the FS to the IS;
i. extracting the DAD from the body cavity.

The present invention additionally provides a clip especially adapted to attach a patch to a biological tissue; the clip comprises (i) at least one hook adapted to at least partially penetrate through the patch to the biological tissue such that an attachment between the patch and the tissue is obtained; (ii) a portion adapted to reversibly connect activation means; the activation means are adapted to actuate the hooks such that the attachment is obtained. The clip is actuated and the attachment is obtained by a linear motion of the activation means.

Still the present invention provides a deployment device (DD) adapted to deploy a patch within a body cavity; wherein the DD is characterize by having a distal portion, adapted to be inserted into a body and a proximal portion, located adjacent to a user. The distal portion and the proximal portion are interconnected along a main longitudinal axis via a tube; the tube having a proximal end (TP) connected to the proximal portion, and a distal end (TD); the tube accommodates at least a portion of a central shaft; the central shaft has a proximal end (CSP) accommodated within the tube and a distal end (CSD) protruding from the TD end; the central shaft is adapted to reciprocally move parallel to the main longitudinal axis within the tube. The distal portion comprises: (i) at least two flexible arm (FA) having a proximal end (FAP) connected via a joint to the TD, and a distal end (FAD) connected via a joint to the CSD; the FA are characterized by having an initial stage (IS) at which the FA are straight and parallel to the longitudinal axis of the central shaft; and, a final stage (FS) at which the FA are laterally curved with respect to the longitudinal axis of the central shaft such that the patch is deployed; the FA are adapted to reversibly transform from the IS to the FS by the reciprocate movement of the central shaft towards and away from the proximal portion. The FA comprises (a) at least one dedicated loop and stretching means adapted to reversibly connect the patch to the FA. The proximal portion comprising at least one handle located outside the body; the handles adapted to (i) reversibly transform the FA from the IS to the FS; and, (ii) release the patch from the FA.

Yet it is an object of the present invention to provide a method for deploying within a body cavity. The method comprises steps selected inter alia from:
a. obtaining a DD as defined above;
b. inserting the distal portion into the body cavity;
c. reversibly transforming the FA from the IS to the FS; thereby deploying the patch;
d. detaching the patch from the FA;
e. transforming the FA from the FS to the IS; and,
f. extracting the DAD from the body cavity.

It should be emphasized that some of the major advantages of the present invention, with respect to the prior art, is to provide a deployment system or a deployment and attachment system that enables (a) an actively deployment—the deployment is actively controlled by the surgeon (as opposed to passive deployment); (b) the deployment is continuous (analogous and not binary such that several deployment levels can be obtained); and, (c) the deployment is bidirectional such that it can be fully reversible.

The term 'close form' or 'initial stage' refers hereinafter to the state of the flexible side arms FA in their initial stage as can be seen from FIG. 2A.

The term 'open form' or 'final stage' refers hereinafter to the state of the flexible side arms in their final stage as can be seen from FIG. 2C or 2D.

The term 'bidirectional' or 'fully reversible deployment' refers hereinafter to the deployment of the patch, which according to the present invention, is fully reversible. In other words, the patch deployment is bidirectional, i.e., the patch can be fully folded (i.e., deployed within the body) and then, if the surgeon desires, the patch can be fully unfolded simply by the reconfiguration of the flexible arms from the initial stage to the final stage and vice versa.

Figure 17:
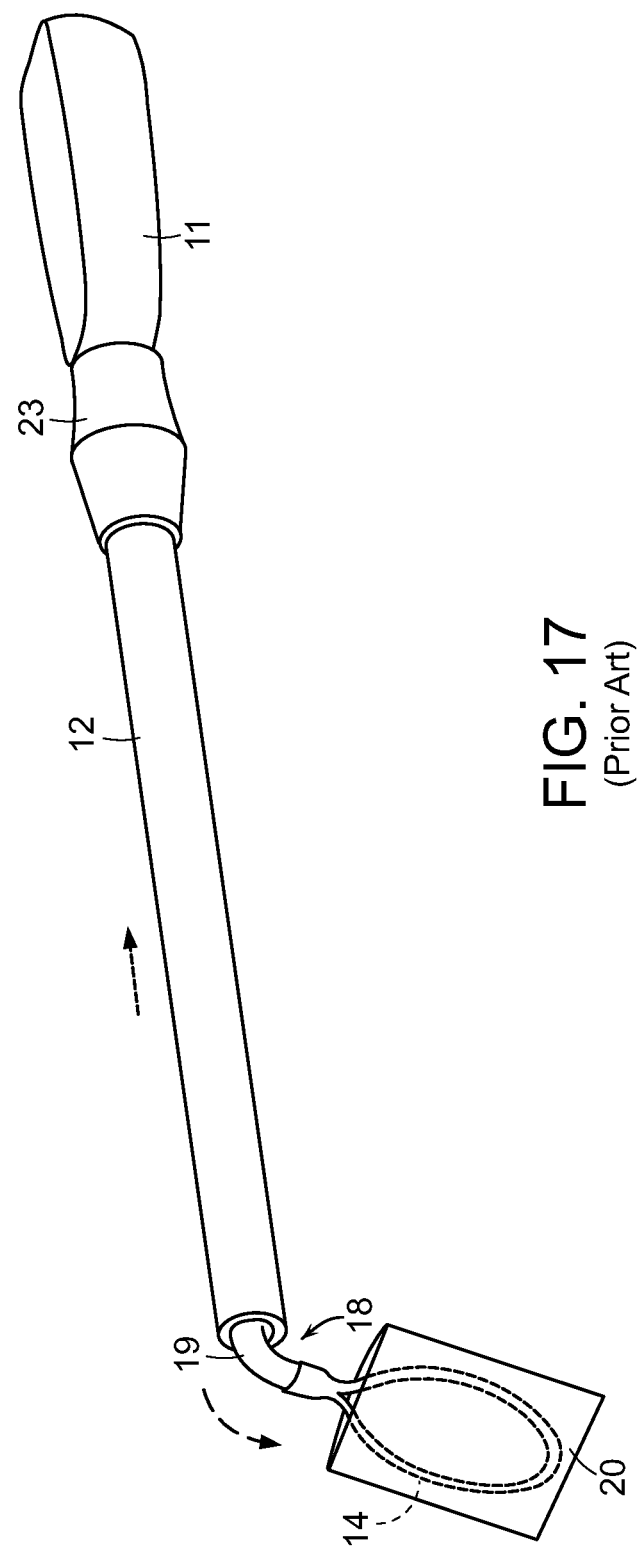
FIG. 17 illustrates a deployment system according to prior art.

The term 'controlled deployment' refers hereinafter to a patch deployment which is continuous; i.e., the deployment is not binary but analogous—there are several deployment levels. This is in contrast so conventional deployment system is now days (see for example U.S. Pat. No. 5,370,650, FIG. 17), in which the deployment of the patch relies upon the elasticity of a loop member surrounding the patch such that the patch can be either fully folded or fully unfolded. No intermediate are enabled. In the present invention there can be several deployment stages.

The term 'aneurysm' refers hereinafter to an aneurysm (or aneurism) is a localized, blood-filled dilation (balloon-like bulge) of a blood vessel caused by disease or weakening of the vessel wall.

The term 'Photolithography' or 'photochemical lithography' refers hereinafter to a process used in microfabrication to selectively remove parts of a thin film (or the bulk of a substrate). It uses light to transfer a geometric pattern from a photomask to a light-sensitive chemical (photoresist, or simply "resist") on the substrate. A series of chemical treatments then engraves the exposure pattern into the material underneath the photoresist.

The term 'laser cutting' refers hereinafter to a technology that uses a laser to cut materials.

The term "Biocompatible materials" refers hereinafter to materials that have the ability to perform with an appropriate host response in a specific application. Biocompatible materials have the quality of not having toxic or injurious effects on biological systems.

The term "self-dissolving materials" or "biodegradable materials" refers hereinafter to materials that are degraded by the body's enzymatic pathways through a reaction against "foreign" material. Some urologists may prefer self-dissolving materials in catheter simply because then they don't have to go necessarily through the procedure of removing them afterwards. Examples of self-dissolving polymers are Polydioxanone (PDO), Polycaprolactone (PCL), Polylactic acid (PLA), Polyglycolic acid (PGA), Adipic acid, PEG and glutamic acid The term "shape memory materials" refers hereinafter to materials which can "remember" there original geometry. After a sample of shape memory materials has been deformed from its original geometry, it regains its original geometry by itself during heating (one-way effect) or, at higher ambient temperatures, simply during unloading (pseudo-elasticity or superelasticity). The thermally induced shape-memory effect has been described for different material classes: polymers, such as polyurethanes, poly(styrene-block-butadiene), Polydioxanone and polynorbornene, metallic alloys, such as copper-zinc-aluminium-nickel, copper-aluminium-nickel, and nickel-titanium (NiTi) alloys.

The term "Hernia" refers hereinafter for umbilical hernia, hiatal hernia, ventral hernia, postoperative hernia, epigastric hernia, spiegelian hernia, inguinal hernia and femoral hernia, generally any abdominal wall related hernia.

The term "orientation of the patch" refers hereinafter to the ability to laterally rotate the patch within the abdominal cavity. Since the shape of the patch is not symmetrical (i.e., rectangular or i.e., ellipse)—it has different directions. Therefore it is highly important to orient the patch (i.e., laterally rotate it) so as the right direction/orientation will face the tissue/hernia.

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

Before explaining the figures, it should be understood that the invention is not limited in its application to the details of construction and the arrangement of the components set forth in the following description or illustrated in the drawings. The invention can be carried out in various ways.

Reference is now made to FIGS. 1a and 1b which describes a preferred embodiment of the present invention.

FIG. 1a is a general view of the deployment and attachment device and FIG. 1b is a closer view of a portion of said deployment and attachment device. According to that embodiment a device 100 which is adapted for deployment and attachment of prosthetic mesh during a minimal invasive (Laparoscopic) hernia repair surgery is provided. The deployment and attachment device (DAD) 100 comprises 2 main portions: distal portion 101, and a proximal portion 102. The distal portion is adapted to be inserted into a body during the surgery via a trocar. The distal portion is also adapted to deploy and attach a hernia patch to the patient's tissue surface. The proximal portion 102 comprises a handle 113 which provides the surgeon with the ability to control the deployment and attachment of the patch. The two portions are connected via a tube 103.

The distal portion comprises of at least 2 flexible side arms (FA) 104 adapted to be bended laterally. The FA are connected at their distal end to the distal end of a central flexible shaft 105, and at their proximal end to the distal end of the tube 103, the connection is made using a flexible joint. The central flexible shaft 105 is adapted to reciprocally move within the tube 103 thereby spread and deploy the patch 106.

A prosthetic hernia repair patch 106 is folded in between the flexible arms (FA) 104 and connected to them via stretching means or especially a wire 107 which passes through the patch and a plurality of dedicated loops 110 located on the FAs 104. The two ends of the wire are connected to the proximal portion 102. A plurality of dedicated hernia clips 108 are connected to the FA 104 at special connection points 111. Sais clips 108 are adapted to attach the patch 106 to the tissue. All the clips 108 are connected together by at least one wire (activation wire) 112 which will serve as their activation means. One end of the activation wire 112 is connected to the proximal portion 102.

The patch 106 is initially coupled to the FAs by a stretching wire 107 and is folded in between the FAs 104 such that it can be inserted into the body within a trocar 114. Once the patch is inserted it is deployed by the central shaft 105 and the FAs 104. Next, the physician brings the patch into adjacent contact with the tissue. Then, the patch is attached to the tissue by clips 108 which are activated by the activation wire 112. Once the patch is attached to the tissue the activation wire 112 and the stretching wire 107 are cut via a dedicated cutting mechanism positioned in the distal end of tube 103. Next, the stretching wire is pulled towards the proximal portion and extracted. By doing so, the patch is no longer coupled to the FAs 104. Next, the FAs brought back into their initial stage, which enables their extraction from the body through the trocar 114.

Figure 2C:
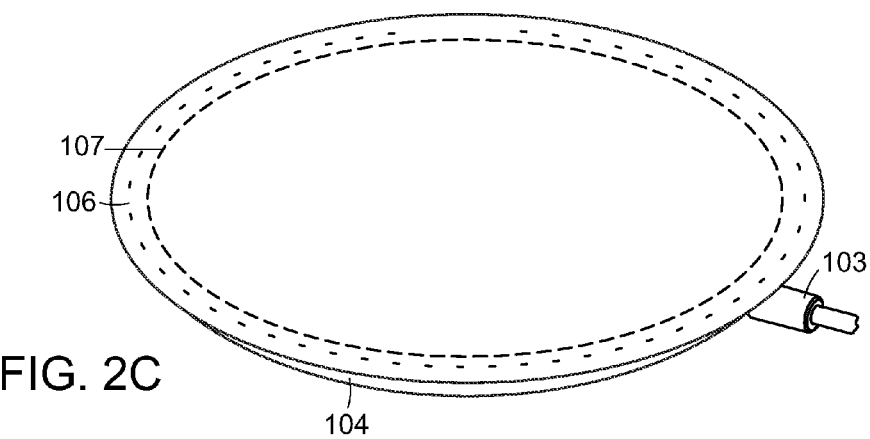
Figure 2D:
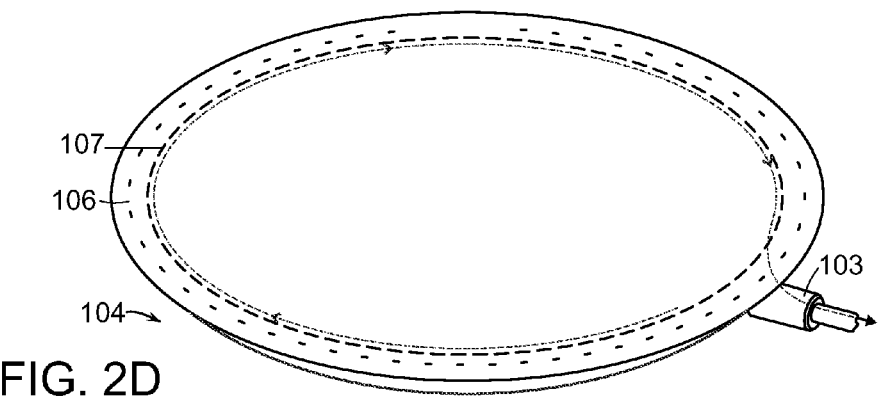

Reference is now made to FIGS. 2A-2D which illustrate the patch deployment process. The initial stage is described in FIG. 2A at which the two FAs are parallel and straight ('close form'). Furthermore, the patch 106 is folded in between the two FAs (FIG. 2A). Once the distal portion has been inserted into the abdominal cavity, the physician deploys the patch by pressing the handle 113 (see FIG. 1, 10A-10E) at the proximal portion 102. Pressing handle 113 results in a movement of the central shaft 105 toward the proximal portion 102. As a result, the distance between the distal end of the central shaft 105 and the distal end of the tube 103 become shorter. Since the FAs 104 are connected to the distal end of the central shaft and the distal end of the tube 10; and since the distance becomes shortened the FAs buckle and bend laterally, thereby forming an eye shape loop as described at FIG. 2B. At this point, the two FAs are in their final stage ('open form'). It should be pointed out that, whilst the FAs 104 are bended, a continues tension at the stretching wire 107 is maintained. The continues tension results in the deployment of the patch 106 together with the bending of the FAs 104. Once the FAs 104 reach their final stage, the patch 106 is completely unfolded and deployed (FIG. 2C). At this point the physician brings the patch to be in contact with the tissue and attaches the patch in a way which will be discus further on. Once the patch have been attached to the tissue, the physician detaches it from the FAs 104 by releasing one end of the stretching wire 107 and pulling it toward the proximal portion 102 (FIG. 2D).

It should be pointed out that the FAs 104 are flexible in the lateral direction and very stiff on the perpendicular direction such that on applied pressure (by the central shaft) they buckle only laterally. Furthermore, due to the fact that the FAs are very stiff on the perpendicular direction, the applied pressure by the central shaft will be equally distributed along the FAs. If the pressure was not equally distributed and was concentrated only at the edges (close to the central shaft), the central portion of the FAs would not be able to apply sufficient pressure on the tissue to enable an attachment.

Figure 2E:
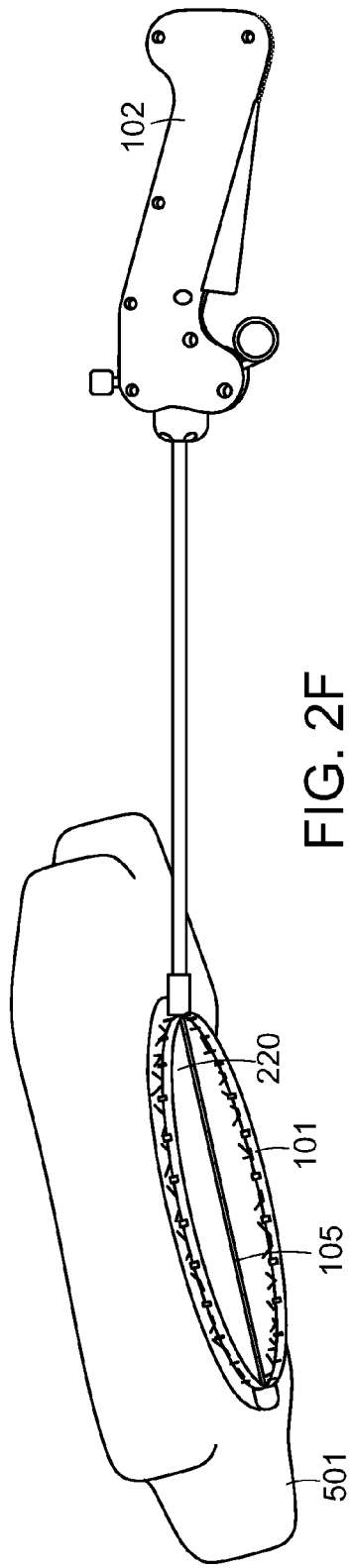
FIGS. 2E-2F represent a side view of the distal portion of device 100 once the patch is deployed.
Figure 2F:
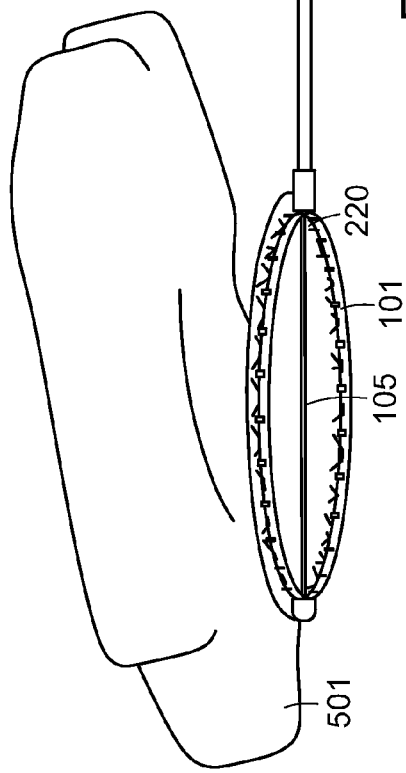

Reference is now made to FIGS. 2E-2F which illustrate a side view of the distal portion of device 100 once the patch is deployed. As can be seen from the figures the device 100 will be able to adjust itself under pressure applied by the physician so as to bring the patch 106 into full contact with the tissue 501. This is due to the fact that the central shaft 105 is flexible. Another option for this capability of device 100 (to be adjustable) is to locate a joint 220 between the distal end of tube 103 and the proximal end of the FA's 104.

Reference is now made to FIGS. 2G-2I which illustrate the distal portion 101 of device 100 adapted to deploy and attach a patch onto a curved surface, i.e. 3D configuration. The 3D device additionally comprises at least one flexible arm 221 in a 3D configuration. The FIG. 2G represent the 3D device in which the FAs 221 and 104 are in a close configuration (initial stage) and FIG. 2H represent the FAs 221 and 104 in the open configuration (final stage). FIG. 2I represents the 3D device with the patch 106. Deploying and attaching the patch will be done essentially the same as for the 2D device.

FIG. 3 describes a number of options for the folding of patch 106 prior to inserting the distal end 101 to the body. In all of the drawings a front cross section is seen showing the patch 106, the FA 104, the clip 108 and the trocar 114. FIG. 3A describes the most simple form of folding the patch 106. As can be seen from the figure, the patch 106 is folded between the two FA 104 in a zigzag form. The main advantage of this form is the fact that this fold is reversible. I.e. it is most likely that the patch will return to this form of folding from an unfolded state when FAs return to their close form. This enables a fast and easy extraction from the body in case the patch was not attached to the tissue.

FIG. 3B describes the most efficient fold. This folding enable to use largest patch since it exploits and utilizes almost the entire available space in the trocar 114. Another advantage of this folding it the fact the patch is located above the clips 108 when it is in the unfolded stage, reducing the risk of entanglement between the patch 106 and the clips 108.

FIG. 3C describes a variation of the previous patch folding. This folding is simpler to implement and it also have the advantage of reducing the entanglement risk as mentioned before.

Figure 4A:
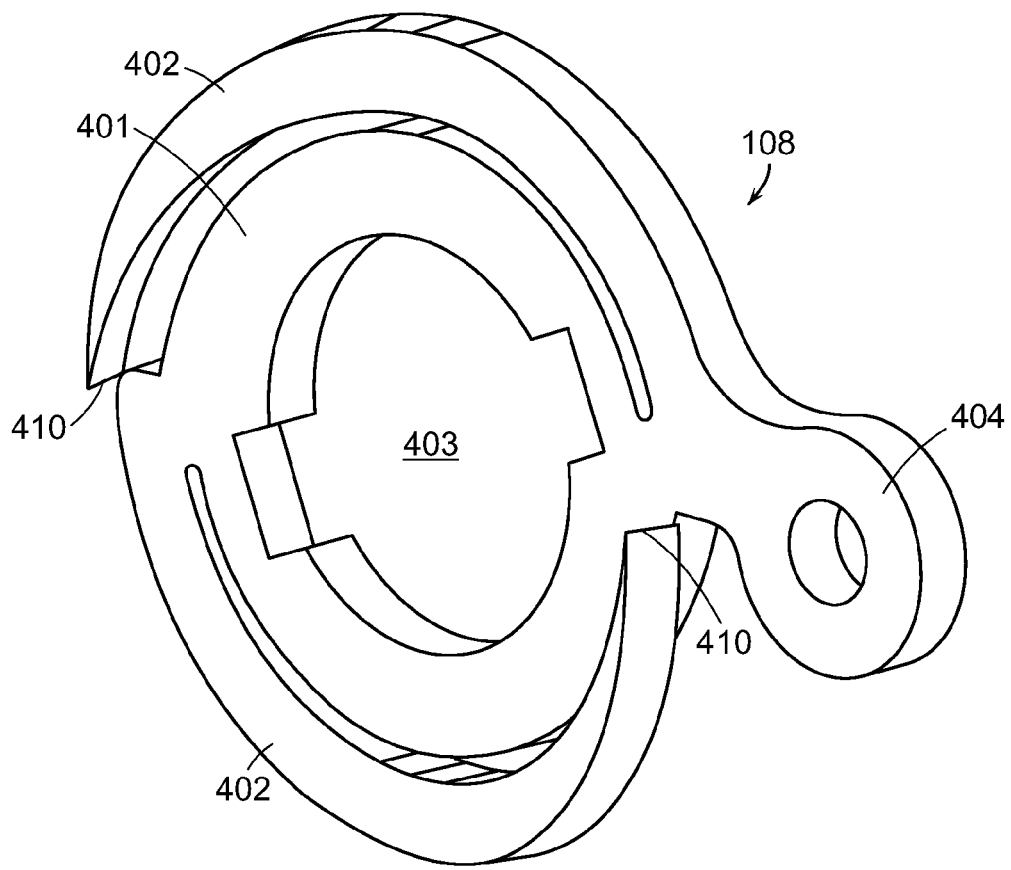
FIGS. 4A-4B illustrate one possible option for the attachment clips.
Figure 4B:
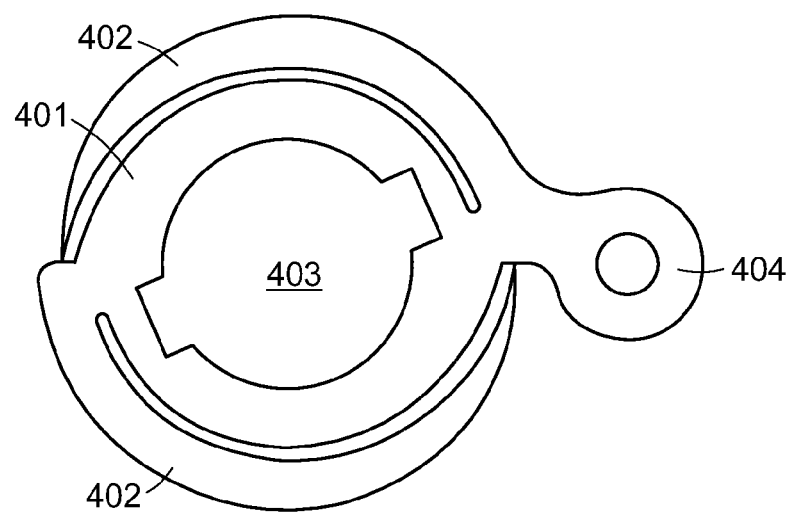

Reference is now made to FIGS. 4A-4B which illustrate the attachment clips and their use during the attachment process.

FIGS. 4A-4B describe a preferred embodiment of the clip 108. The clip comprises of a main portion 401 which is connected to at least 2 lateral curved hooks 402 adapted to penetrate the tissue. The main portion is reversibly connected to the FAs 104 by a central connection area 403. The clip 108 additionally comprises a connection point 404 to the activation wire 112. In a preferred embodiment of the present invention the connection point 404 is positioned laterally to the main portion 401. It should be pointed out that the activation wire 112 connects all the clips 108 together. Furthermore, as can be seen from FIG. 4A the two hooks 402 are titled with regards to the main portion 401. This incline is of much importance. This incline is responsible for the fact that the hooks' edges 410 are constantly presses against the tissue prior to the clip's activation; such that once the clips are activated, the edges 410, will penetrate the tissue and not only slide along the patch 106 surface.

The clip 108 can be made of any biocompatible metal (such as stainless steel, titanium), shape memory materials, super elastic metals (such as Nitinol i.e. NiTi), non-degradable polymer (such as polyurethane, PVC, PTFE (i.e. Teflon), PC (polycarbonate), degradable polymers (such as PLA, PGA, PLLA, PCL, PDS).

It should be pointed out that the clips 108 can be produced by photochemical lithography methods, laser cutting method.

The FA can be made of any biocompatible metal (such as stainless steel, titanium), shape memory materials, super elastic metals (such as Nitinol i.e. NiTi), non-degradable polymer (such as polyurethane, PVC, PTFE (i.e. Teflon), PC (polycarbonate).

The activation wire 112 and the stretching wire 107 can be made of any biocompatible metal (such as stainless steel, titanium), shape memory materials, super elastic metals (such as Nitinol i.e. NiTi), non-degradable polymer (such as polyurethane, PVC, PTFE (i.e. Teflon), PC (polycarbonate), degradable polymers (such as PLA, PGA, PLLA, PCL, PDS).

Figure 5A:
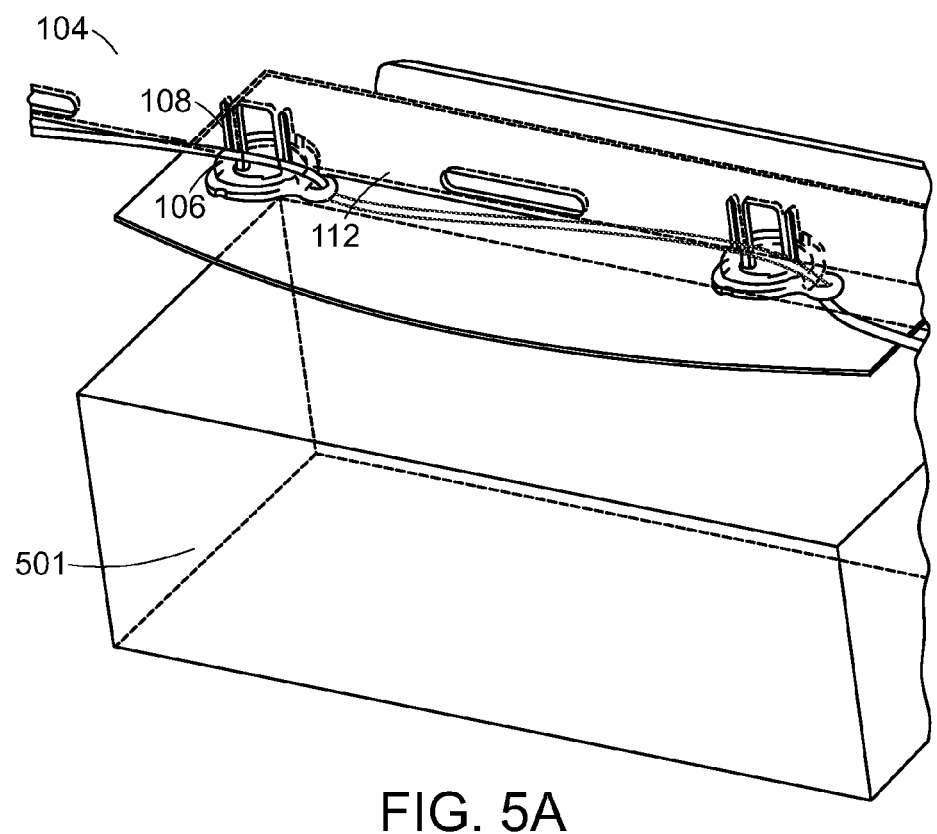
Figure 5B:
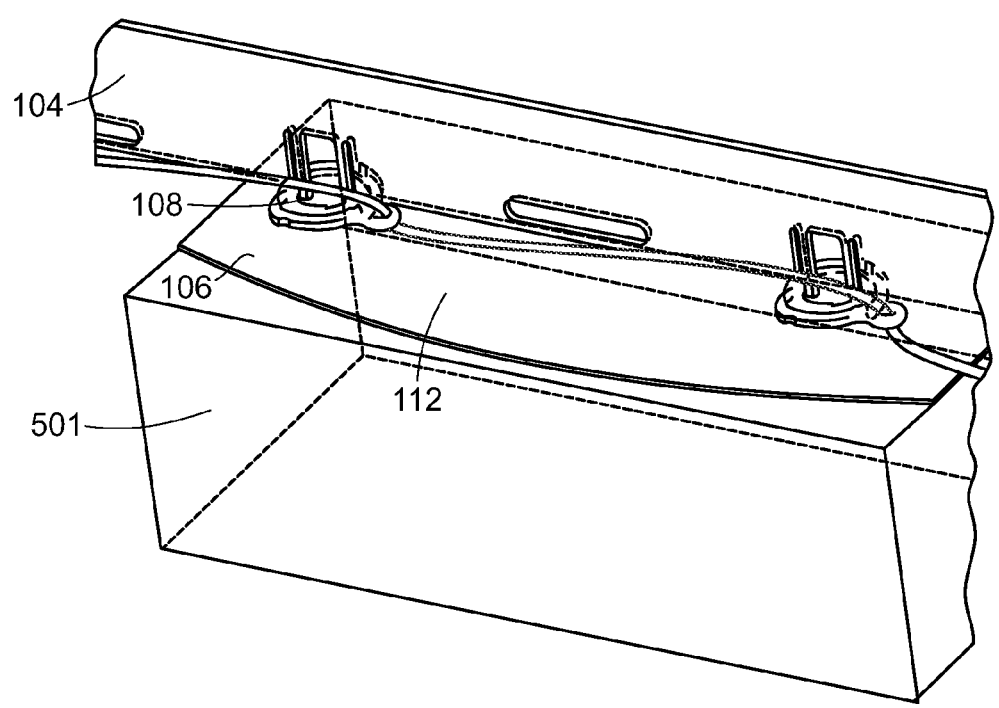
Figure 5C:
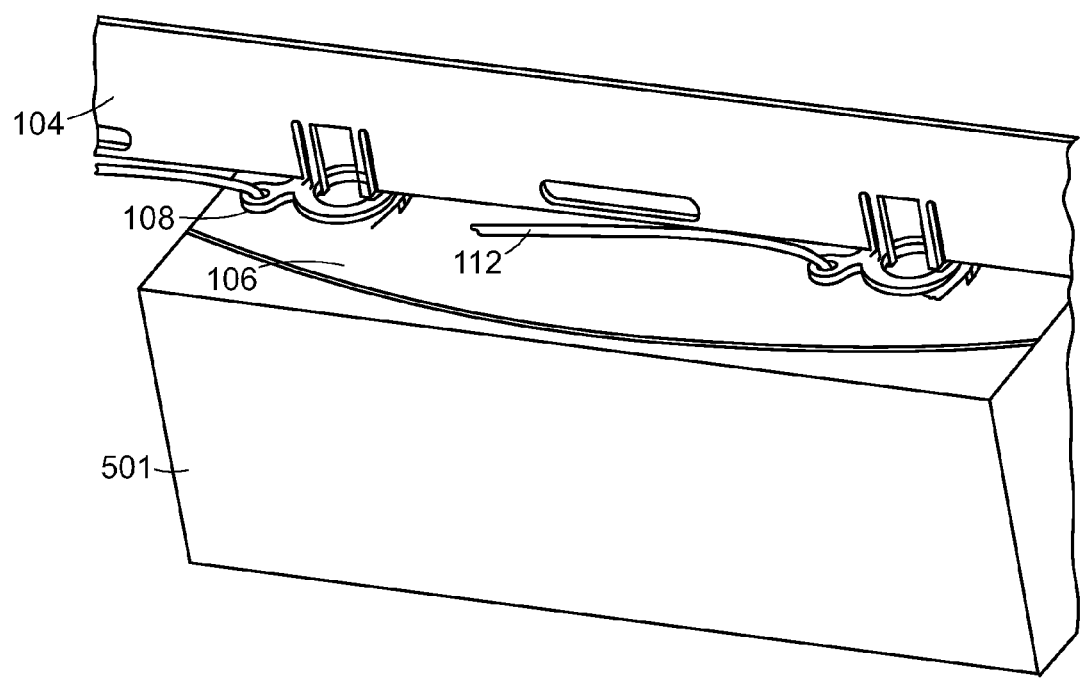

Reference is now made to FIGS. 5A-5D which describes the attachment between a patch 106 and a tissue 501. FIG. 5A illustrates the tissue 501, the patch 106, the clips 108, the FAs 104 and the activation wire 112. Once the physician brings the patch adjacent and in contact with the tissue (FIG. 5B), the activation wire 112 is then pulled, generating a rotational moment which rotates the clip with regards to the FAs 104. The rotational movement inserts the hooks 402 into the tissue 501 through the patch 106, thereby providing a strong attachment between the patch 106 and the tissue 501 (FIG. 5C). The connection between the clip 108 and the FAs 104 is made in such a way that the clips 108 are secured to the FAs 104 prior to the attachment; and, the clips 108 detach from the FAs 104 once they are attached to the tissue 501 (FIG. 5D).

Figure 6A:
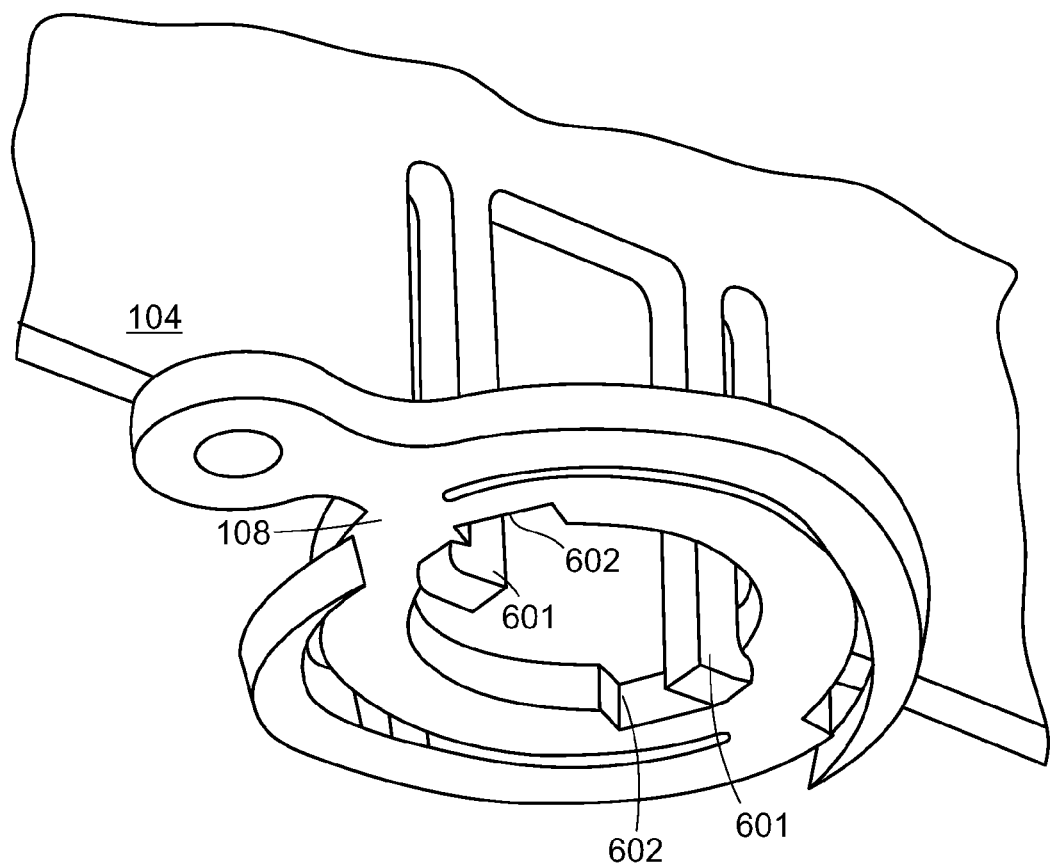
FIGS. 6A-6F illustrate means adapted to reversibly connect clips 108 to the FAs 104.
Figure 6B:
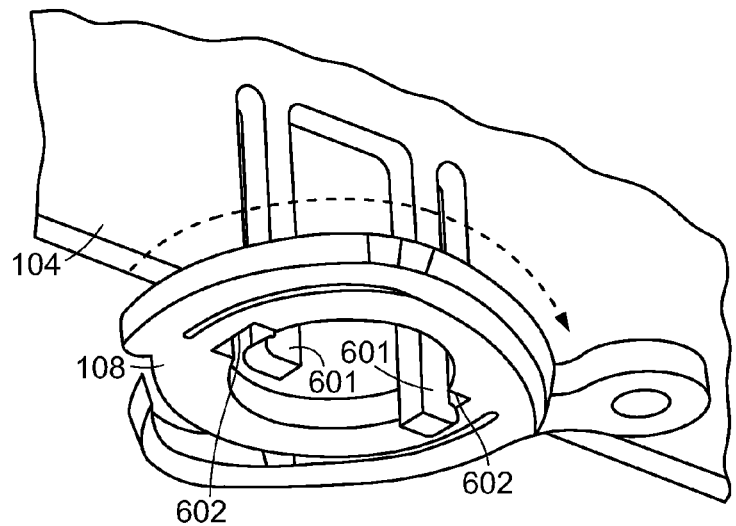
Figure 6C:
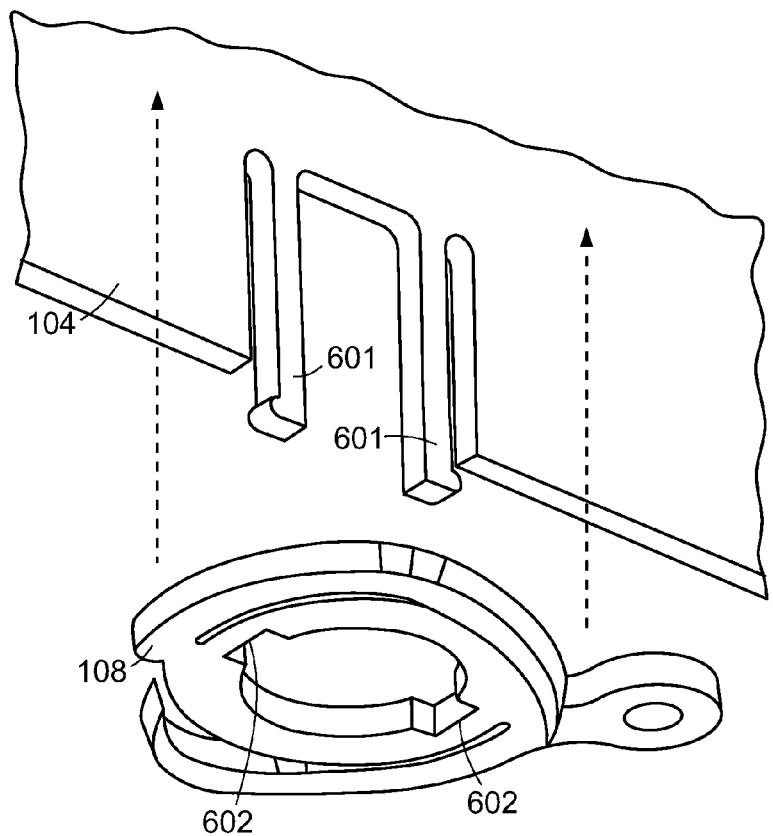

Reference is now made to FIGS. 6A-6C which illustrate means adapted to reversibly connect clips 108 to the FAs 104. According to this embodiment, clips 108 are connected to the FA's by hooks. As can be seen from the FIG. 6A the hooks 601 protrude from the FA's into portion 403 of the clip 108. The clips are secured to the FA's due to L shape of hook 601.

Two niches 602 are located on two opposite side along portion 403 perimeter. Prior to activating the clips (i.e. pulling activation wire 112), the niches 602 are not aligned together with the hooks 601. Once the clips are activated, or in other words they rotate, the hooks 601 are aligned with the niches 602 (see FIG. 6B) such that the attachment between the clips and the FA is cancelled and the clips 108 are released from the FA 104 (see FIG. 6C).

Figure 6D:
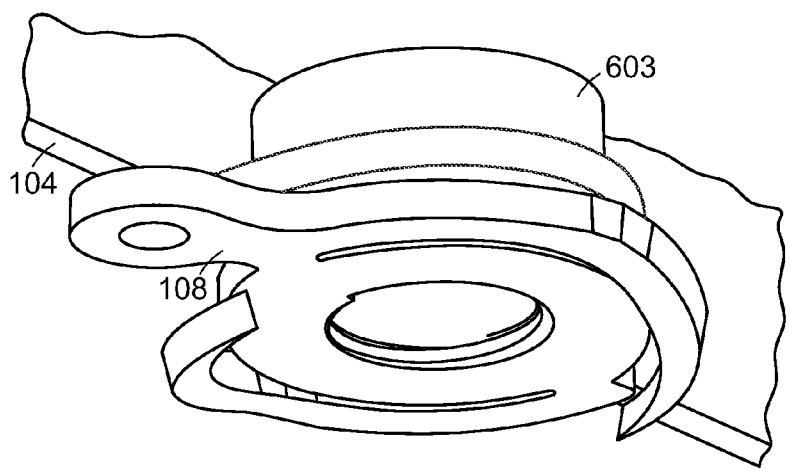
Figure 6E:
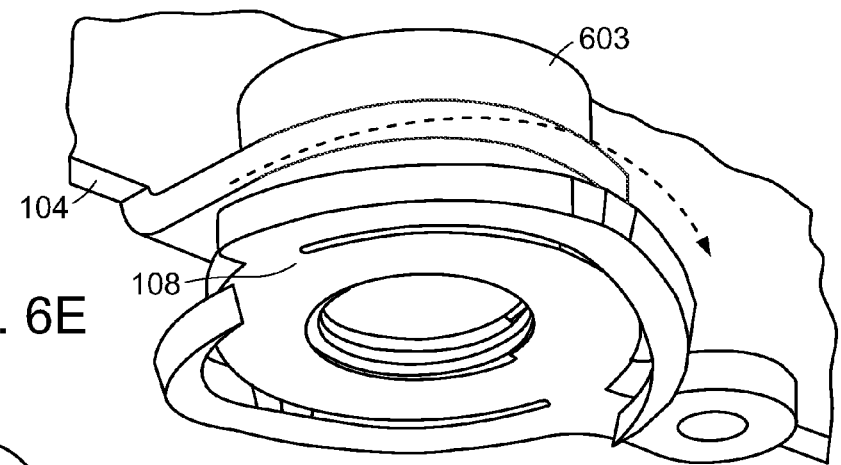
Figure 6F:
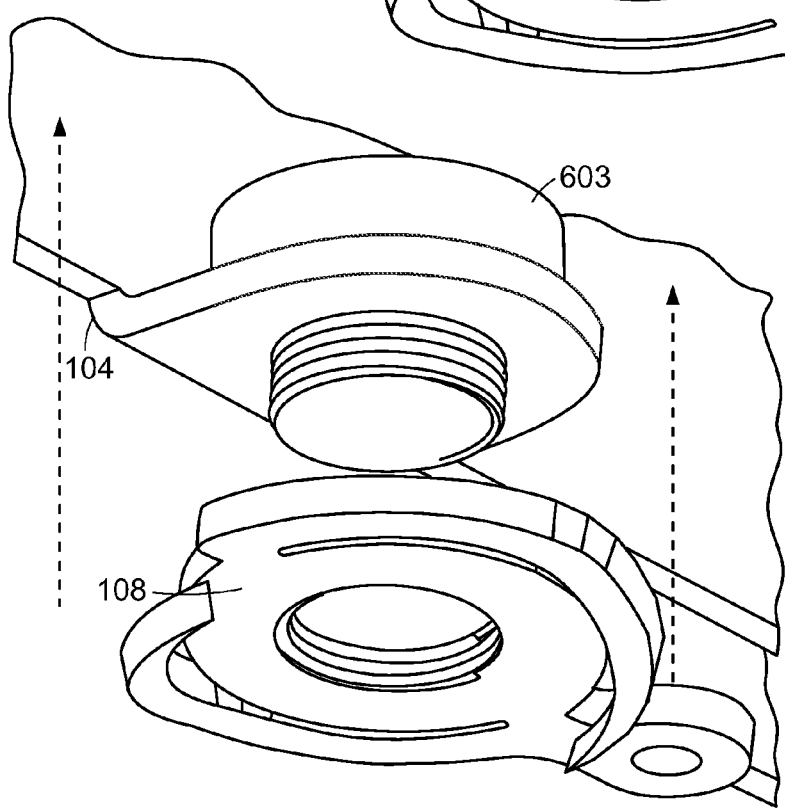

Reference is now made to FIGS. 6D-6F which illustrate means according to another embodiment adapted to reversibly connect clips 108 to the FAs 104. According to this embodiment, clips 108 are connected to the FA's by a dedicated screw. As can be seen from FIG. 6D, screw 603 protrude from the FA's into portion 403 of the clip 108. The clips are screwed into screw 603 thereby secured to the FA's.

The clips can be detached from the FAs by screwing out the clips from screw 603 (see FIG. 6E). Once the clips 108 are screwed out from the screw 603 they are released from the FAs (see FIG. 6F).

It should be pointed that it is in the scope of the present invention wherein the clips 108 can be attached to the tissue and detach from the FA simultaneously or it can be done in two different steps.

Figure 7A:
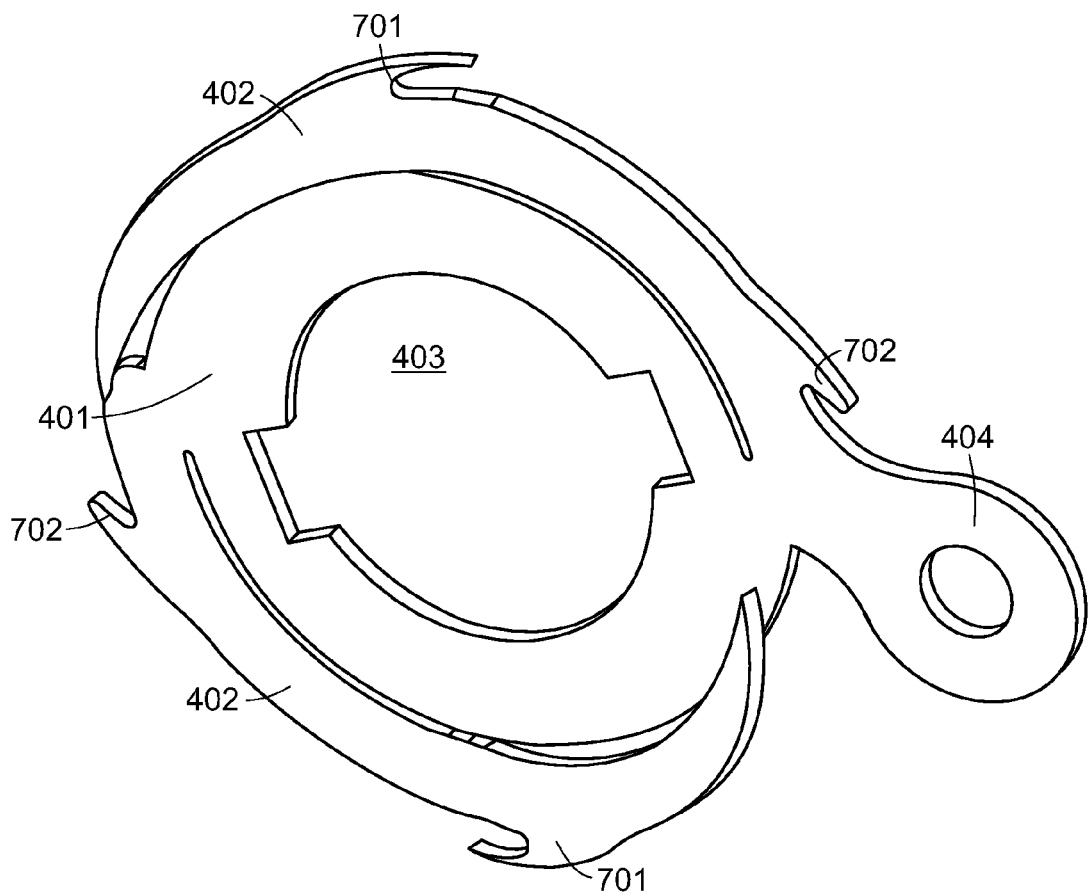
FIGS. 7A-7B illustrate the clip 108 according to another preferred embodiment of the present invention.
Figure 7B:
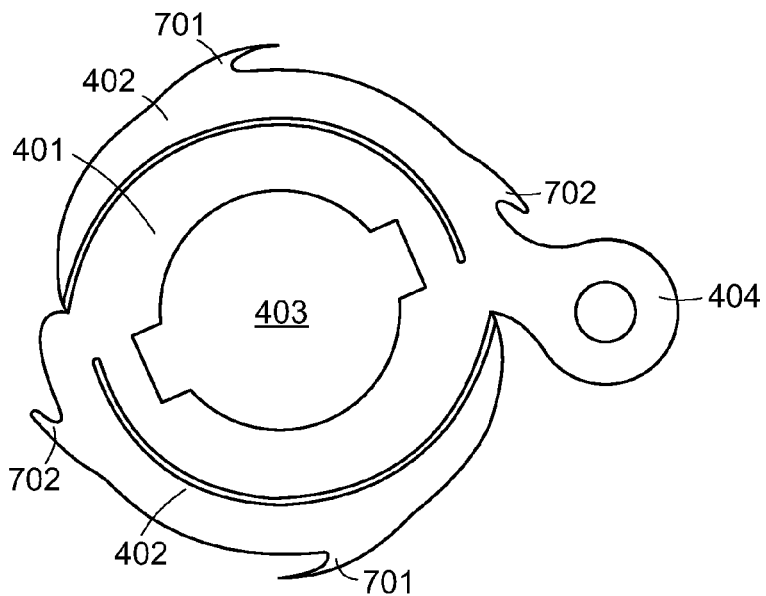

Reference is now made to FIGS. 7A-7B which illustrate the clip 108 according to another preferred embodiment of the present invention. According to this embodiment, the clip 108 includes at least one additional hook 701 located on the lateral hooks 402. This hook 701 is adapted to prevent the reverse rotation (hence the release) of the clip 108 from the tissue 501. It is acknowledged that the attachment between the patch 106 and the tissue 501 can be annulled if the clip 106 rotates in the reverse rotational motion when subjected to external loads. Therefore, the additional hook 701 prevents this reverse rotational motion with minimal interference to the forward rotation. Clip 108 may additionally comprise at least one hook 702 which is adapted to prevent any unwanted movement between the patch 106 and the clip 108.

Figure 7C:
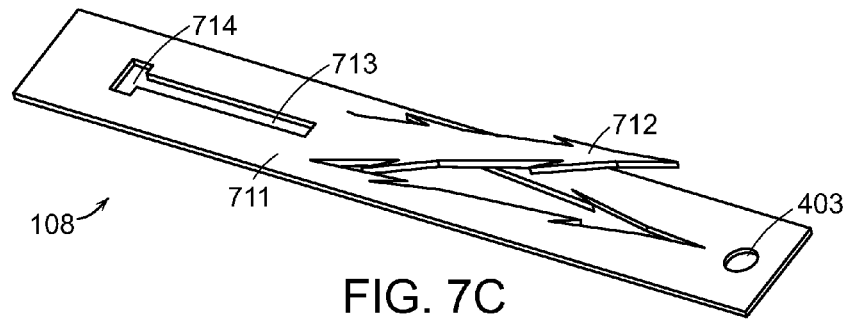
FIGS. 7C-7N illustrate another embodiments of clips 108. Said clip 108 are activated by pulling.

It is in the scope of the present invention wherein attachment clips, activated by pulling, are provided. Another example for such clips is demonstrated in FIGS. 7C-7H. FIG. 7C illustrates an arrow-like clip 108. The Clip 108 is characterized by having a plate 711 and an arrow-like shaped hook 712. Hook 712 is adapted to penetrate the patch 106 and the tissue 501. Plate 711 also comprises groove cut 713 and a dedicated aperture 714. As described before, clip 108 has a connection point 403 to the activation wire 112.

FIGS. 7D-7G illustrate the steps needed for attaching the clip to the tissue 501.

Figure 7D:
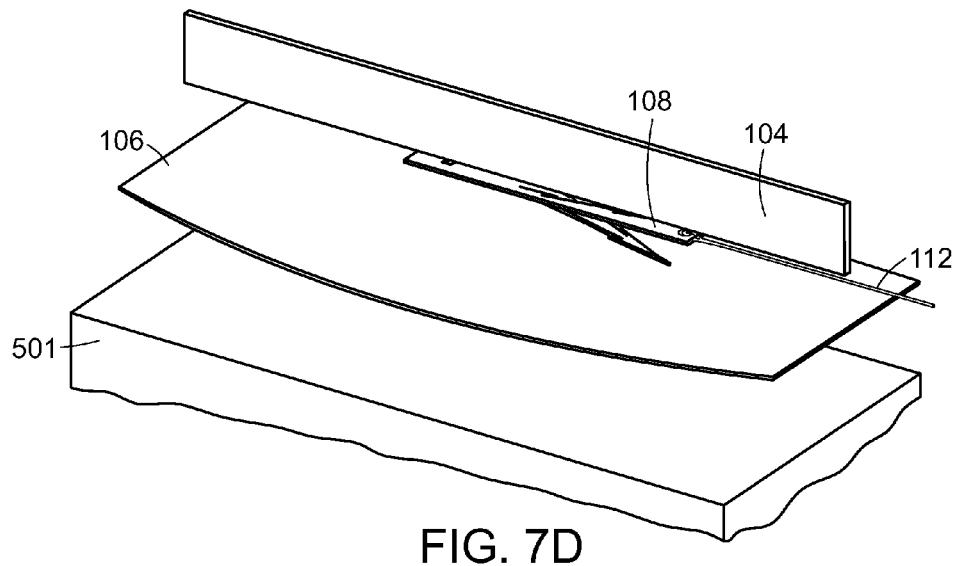
Figure 7E:
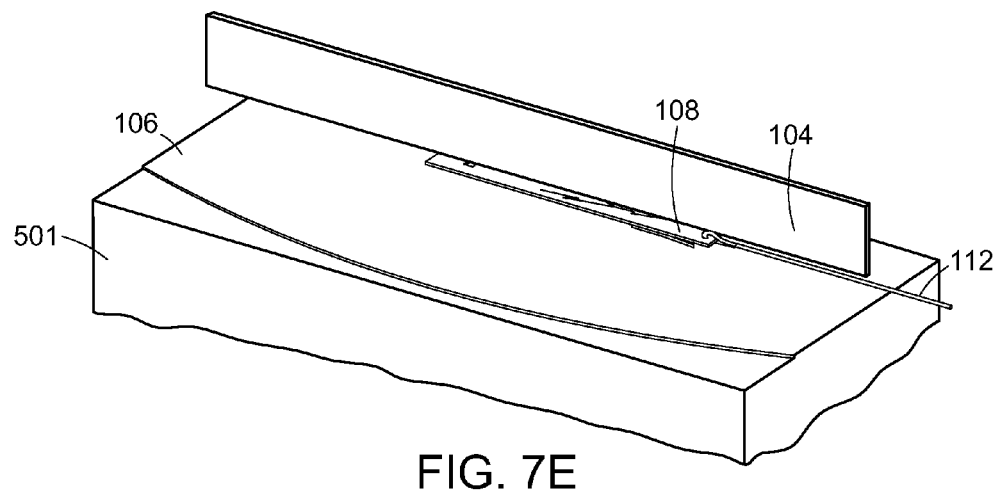
Figure 7F:
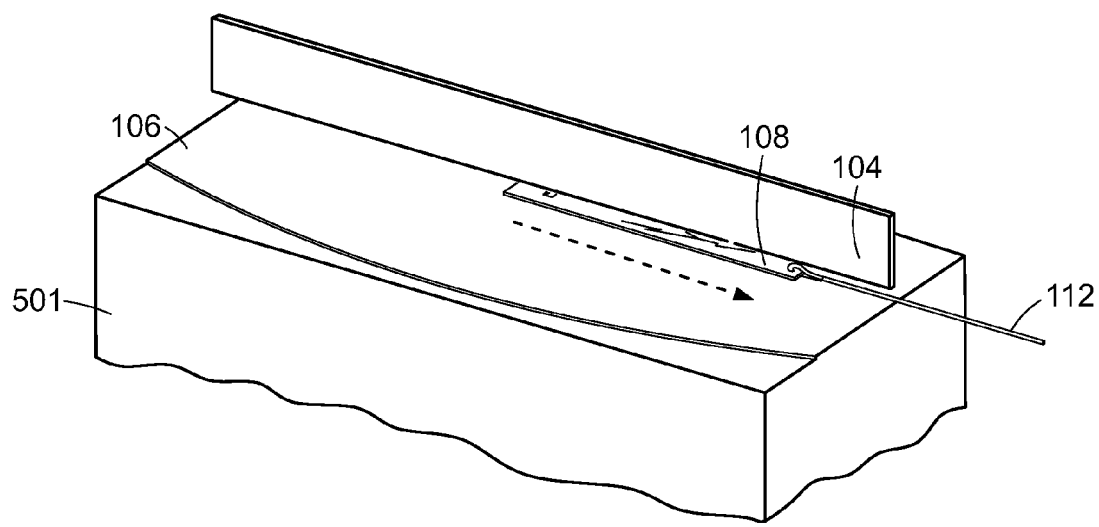
Figure 7G:
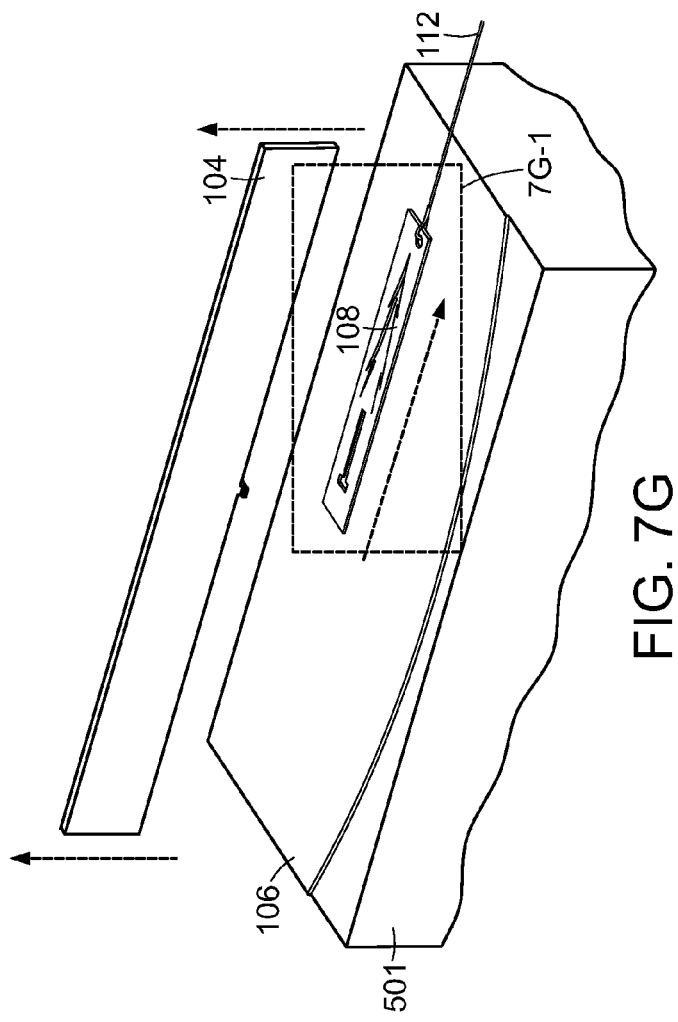
Figures 1, 7G:
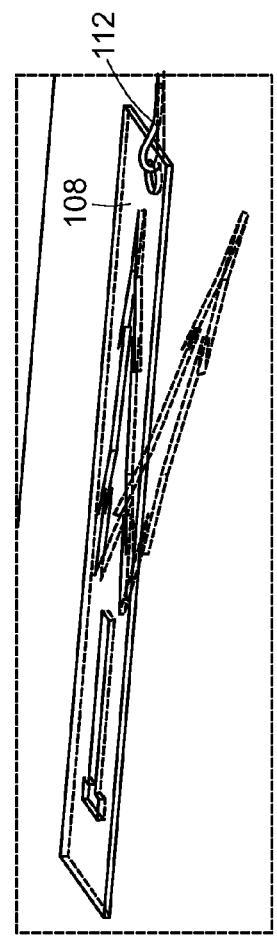

FIG. 7D illustrates the clip 108 coupled to the FA 104 and being brought into adjacent contact with the tissue 501. FIG. 7E illustrates the clip 108 being presets against the tissue 501. The next step is attaching the patch to the tissue via clips 108 (FIG. 7F). The attachment is obtained by pulling the activation wire 112. Once the clip 108 is attached to the tissue 501, it detaches from the FA 104 (FIG. 7G).

Figure 7H:
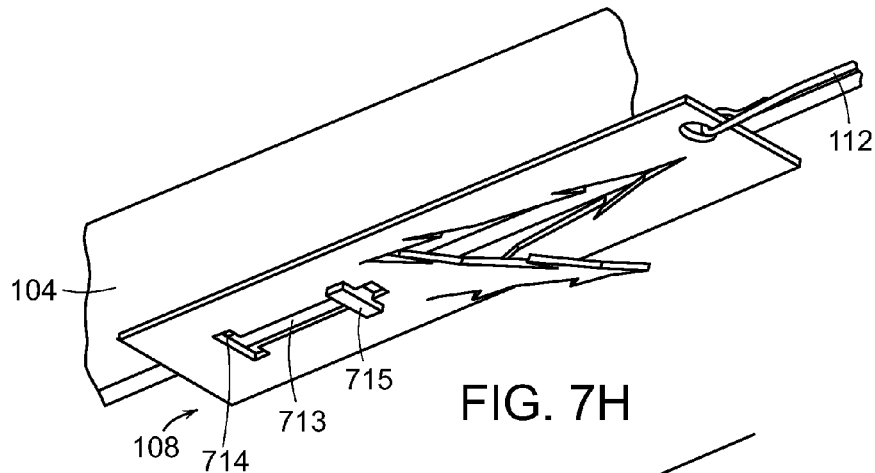
Figure 7I:
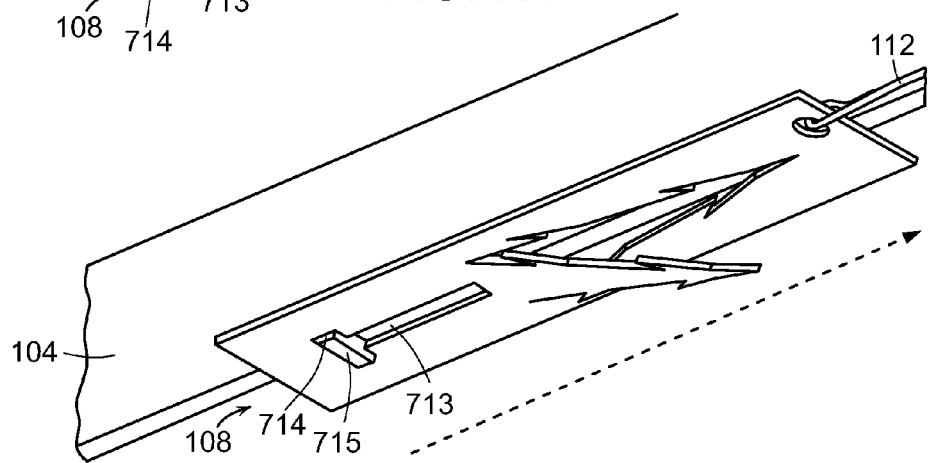
Figure 7J:
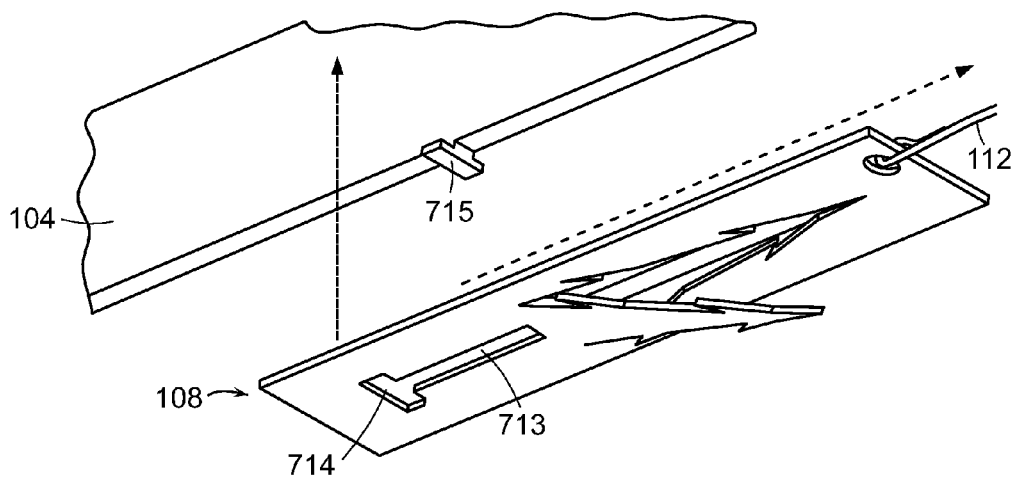
Figure 7K:
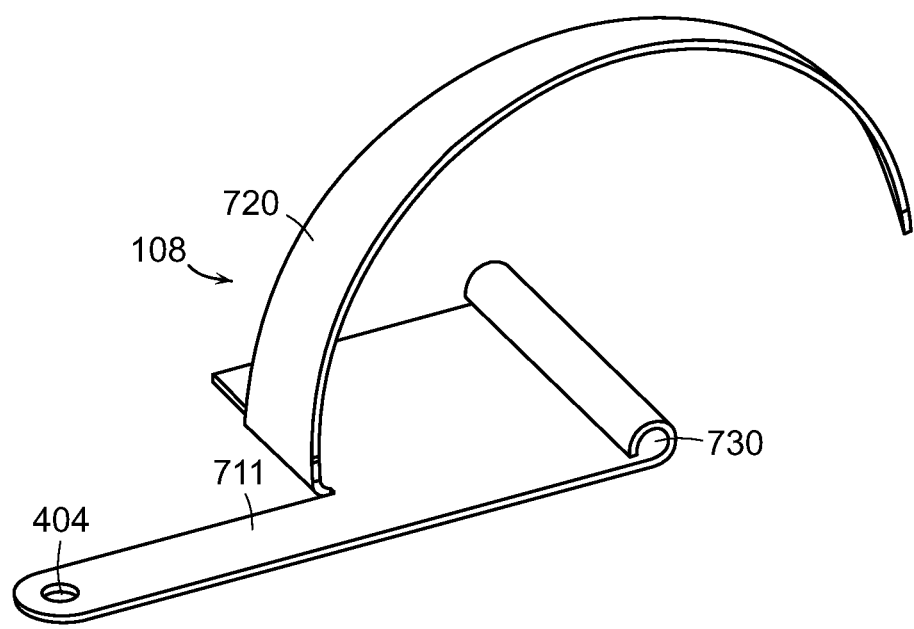

FIGS. 7H-7J illustrate a closer view of the arrow-like clip 108 and how it detaches from the FAs 104.

FIG. 7H illustrate the clip 108 attached to the FAs 104. The attachment between the clip 108 and the FA is provided by a dedicated hook 715 which is inserted into the groove cut 713 in the plate 711.

When the activation wire 112 is pulled (by the handle 1002) the clips 108 are pulled towards the proximal portion 102. By pulling the clips 108, the arrow like hook 712 penetrates the tissue 501. The result of this pulling is the movement of hook 715 within the groove cut 713 until said hook 715 reaches the dedicated aperture 714. Aperture 714 is adapted to fit the dimensions, shape and size of the hook 715. Once hook 715 reaches the aperture 714 (FIG. 7I) the clip 108 can be detach from the FA 104 (FIG. 7J).

FIGS. 7K-7N illustrate a clip 108 according to another embodiment of the present invention. This clip 108 is characterized by a plate 711 and a sharp curved edge 720. Plate 711 is attached to the FAs 104 by a screw or by a pin 721 (see FIG. 7N). Pin 721 is adapted to be reversibly connected to a dedicated connection area 730 within clip 108. As described before, clip 108 has a connection point 403 which is adapted to be connected to the activation wire 112.

Figure 7L:
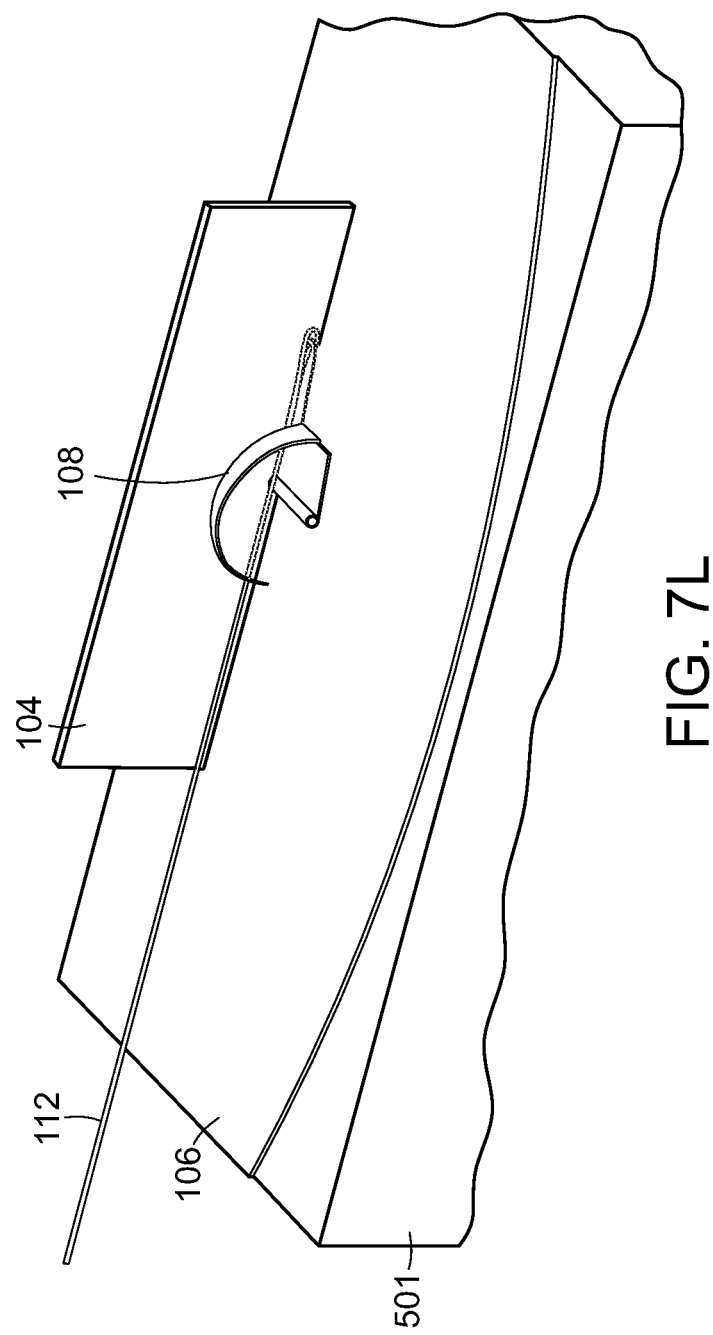

FIGS. 7L-7—illustrate the steps needed for attaching the clip to the tissue 501.

Figure 7M:
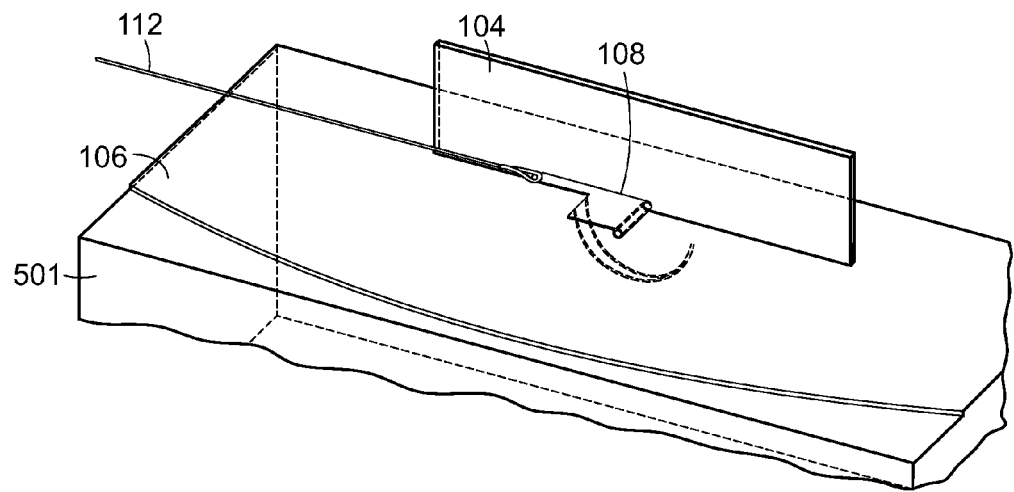
Figure 7N:
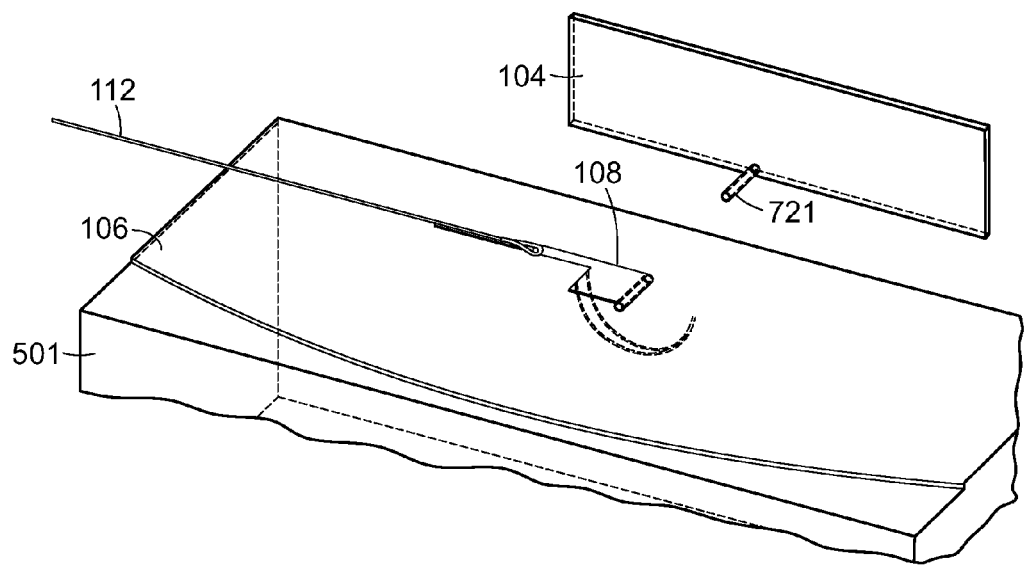

FIG. 7L illustrate the clip 108 attached to the FAs 104 and being brought into adjacent contact with the tissue 501. When the activation wire 112 is pulled (by the handle 1002), clips 108 are rotated and thus, their sharp edge 720 penetrates the tissue 501 (FIG. 7M). Once the sharp edge 720 penetrates the tissue 501, the clip 108 can be detached from the FA 104 (FIG. 7N). The detachment can be obtained by extracting the pin 721 from the clip 108.

Another option for the detachment is by the rotational motion of the clip 108 itself. In this case the clip 108 is attached to the FA 104 by a screw. The rotational motion needed for the attachment of the clip to the tissue will also be used for detaching (by unscrewing) the clip from the FA 104.

Figure 8A:
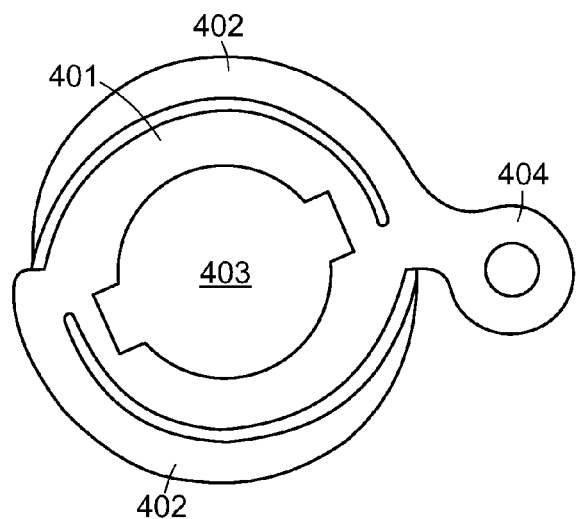
FIGS. 8A-8F illustrate several embodiments for the connection between the activation wire 112 and the clip 108.
Figure 8B:
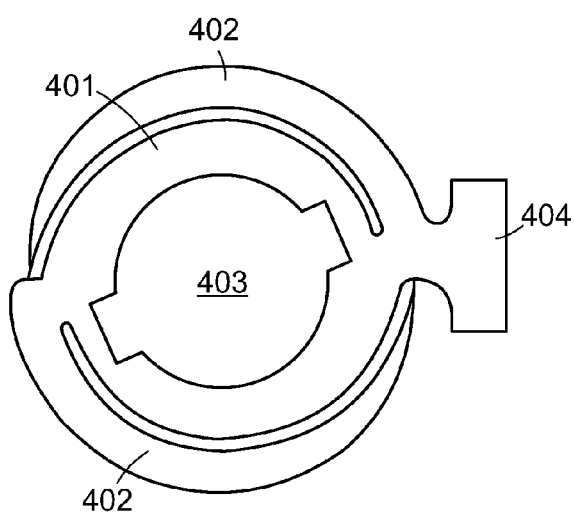
Figure 8C:
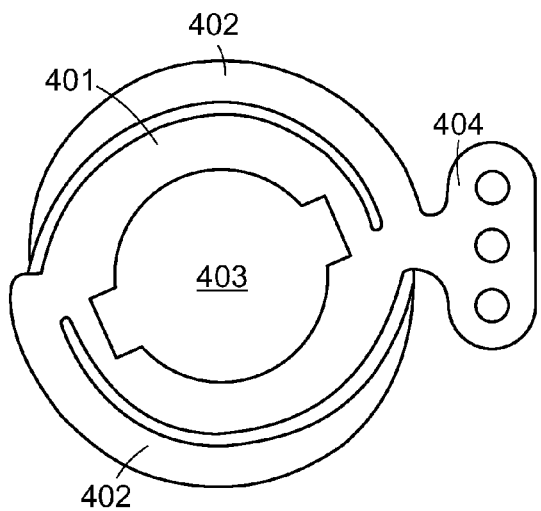
Figure 8D:
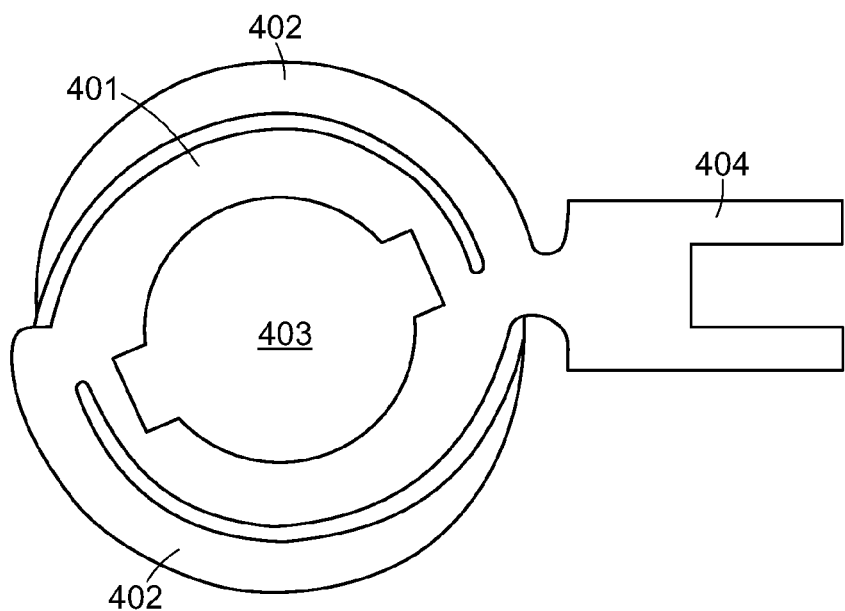
Figure 8E:
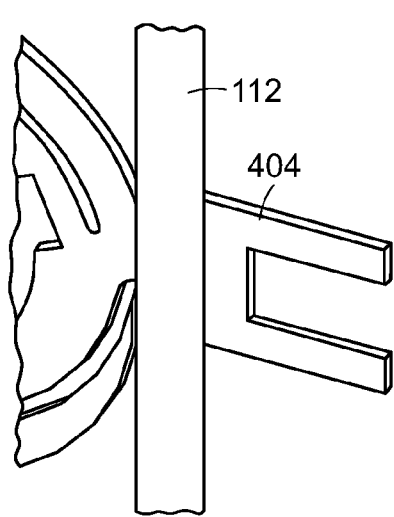
Figure 8F:
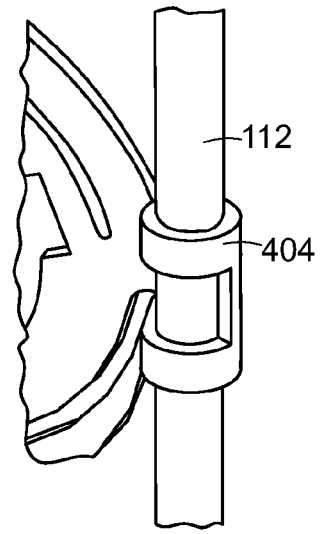

Reference is now made to FIGS. 8A-8F which illustrate several alternative embodiments for the connection between the activation wire 112 and the clip 108. One option to connect the activation wire 112 and the clip 108 is as described in FIG. 8A. The activation wire can enter the connection point 404 (which can be an aperture) and glued or tied to it. Another option is demonstrated in FIG. 8B in which the activation wire is glued parallel to the connection point which has a rectangular profile providing sufficient attachment surface. FIG. 8C represents another alternative in which a number of apertures are provided. The activation wire 112 can enter the apertures in a zig-zag form or back and forth look thereby providing a glue-less attachment. FIGS. 8D-8F represent another possible embodiment for the connection between the activation wire 112 and the connection point 404. According to this embodiment, a fork like portion 404 encapsulates the wire 112.

Once the patch 106 is attached to the tissue 501 the stretching wire 107 and the activation wire 112 are cut.

Reference is now made to FIGS. 9A-9D which represent one possible embodiment implementing a mechanism 901 for cutting the activation wire 112 and the stretching wire 107. Those figures illustrate a cross section view of the cutting mechanism 901. As can be seen from the figures, the cutting mechanism 901 is located at the distal end of tube 103. This location was chosen for two reasons: (i) the fact that the edge of the activation wire 112 should be as shorter as possible once the wire has been cut (this leftover from the wire remain in the body, therefore it is preferable that the leftover would be as short as possible); and, (ii) the fact that the stretching wire 107 is pulled out of the body. In order to extract the wire 107, it has to pass towards the patch and through the perimeter of the patch. To enable an easy extraction of wire 107 it is preferred to cut the wire as close as possible to the patch—i.e. in the distal end of tube 103.

Figure 9A:
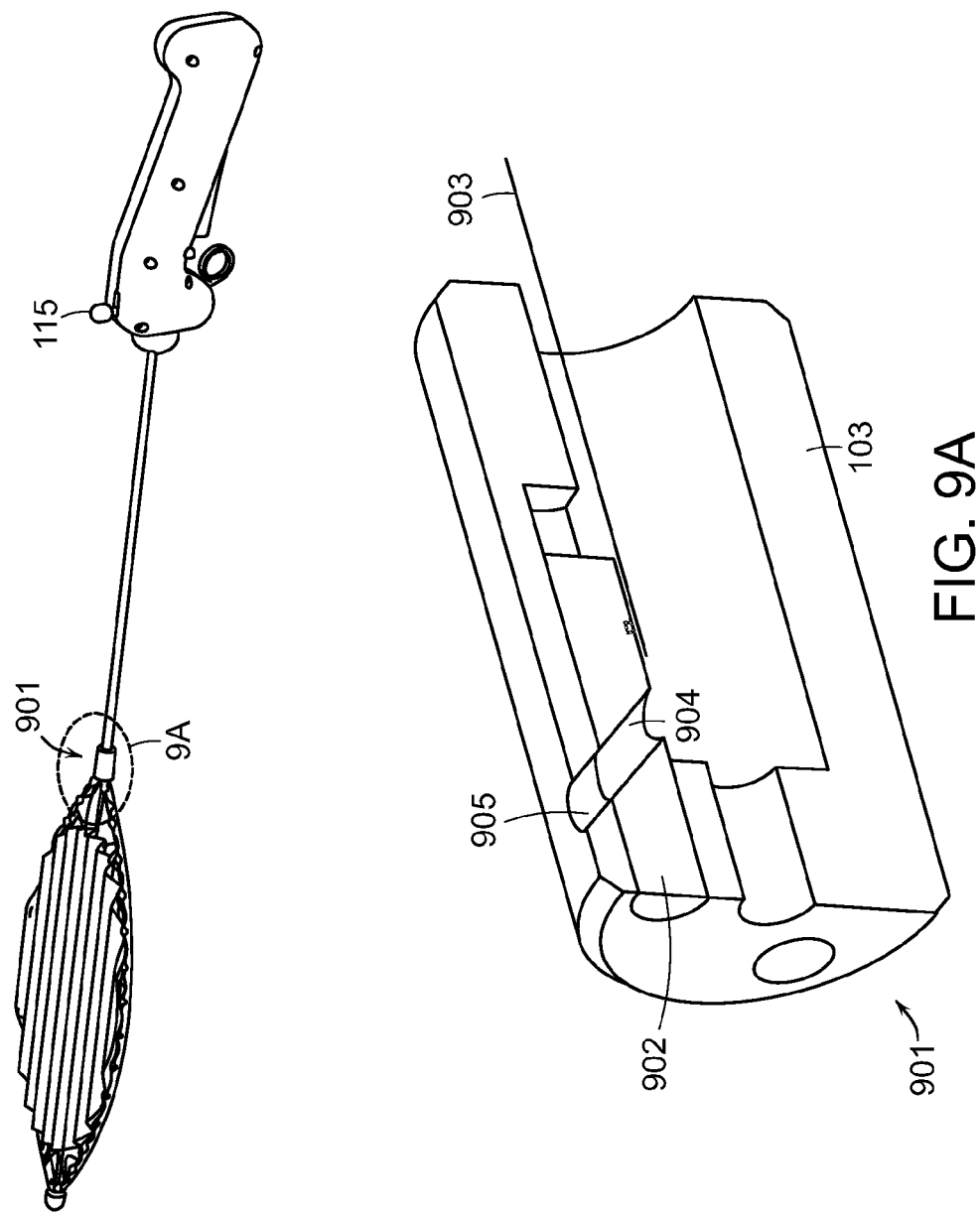
FIGS. 9A-9D represent a cross sectional view of the mechanism 901 for cutting the activation wire 112 and the stretching wire 107.
Figure 9B:
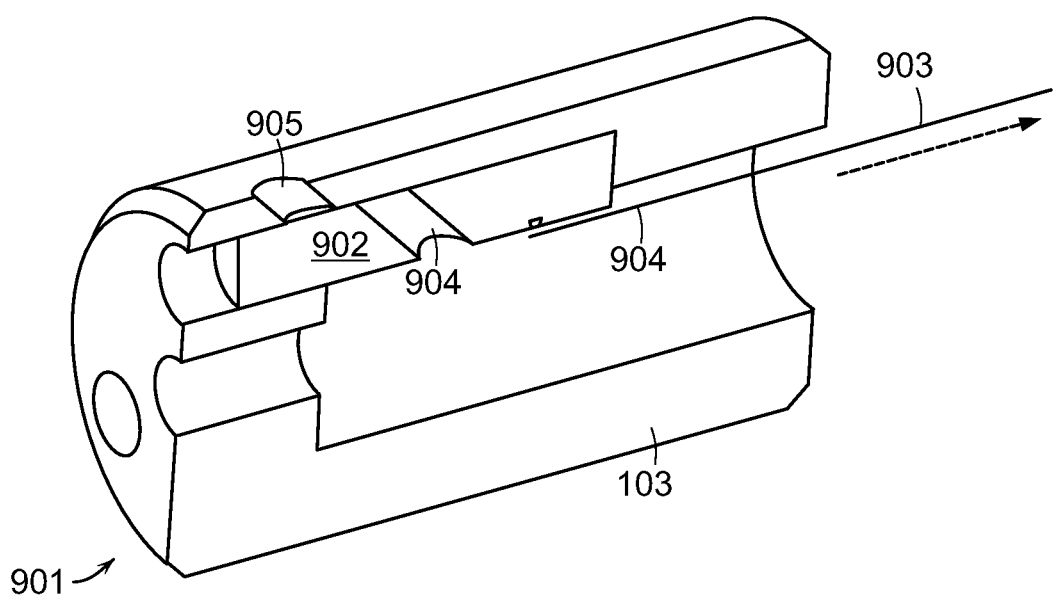
Figure 9C:
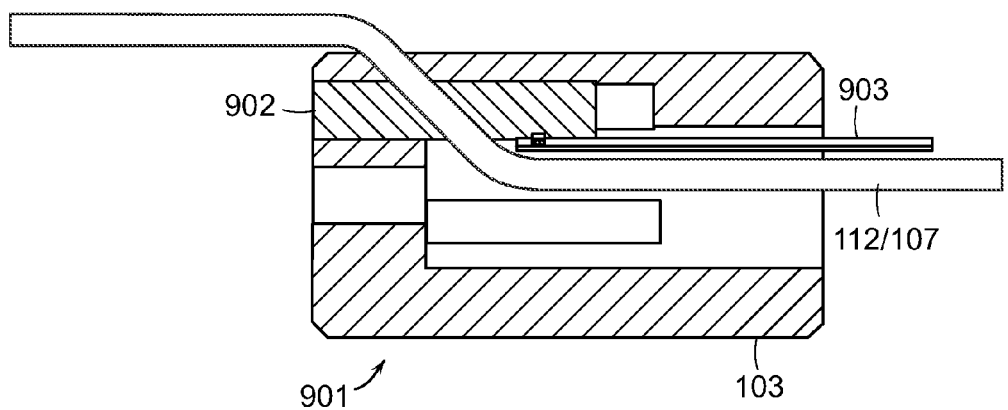
Figure 9D:
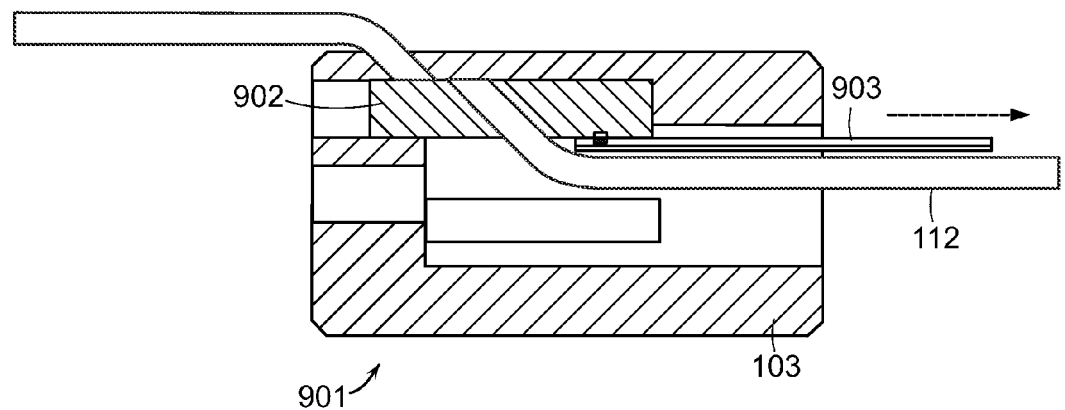

FIGS. 9A-9B illustrate a 3D cross section of the cutting mechanism 901 and FIGS. 9C-9D illustrate a 2D cross section of the cutting mechanism 901.

The cutting mechanism 901 comprises a dedicated cutting pin 902 is placed inside tube 103 near the distal end. The cutting pin 902 is connected to the distal end of a cutting activation wire 903. The proximal end of the cutting activation wire 903 is connected to the proximal portion 102 of device 100. Pulling the cutting activation wire 903 will result in a reciprocate movement of the cutting pin 902 (which is parallel to tube 103 longitudinal axis).

Both the cutting pin 902 and the tube 103 have lateral holes (904 and 905 respectfully) through which the activation wire 112 and\or the stretching wire 107 are passing through. Furthermore the activation wire 112 and the stretching wire 107 can move freely inside the holes (904 and 905). Once the patch 106 is attached to the tissue 501 the physician now needs to cut both the activation wire and the stretching wire. In order to cut those wires the physician will press the cutting handle 115 (the handle will be discussed in further details in FIG. 10) at the proximal portion 102. As a result the cutting activation wire 903 and the cutting pin 902 will be pulled toward the proximal portion 102 and a shear force will be implemented on the activation wire 112 and/or the stretching wire 107, hence cutting them to two sections as illustrated in FIG. 9B.

It is further in the scope of the present invention wherein a single mechanism is adapted to cut both the activation wire 112 and the stretching wire 107. It is further in the scope of the present invention wherein two separate mechanisms are adapted to cut the activation wire 112 and the stretching wire 107.

In a preferred embodiment of the present invention, at least a portion of the activation wire remains within the body, thereby providing additional fixation to the clips. This additional fixation is needed in case one of the clips detaches from the patch and may wander inside the body, causing complications.

It is in the scope of the present invention wherein the entire activation wire 112 detaches from the clips 108 and extracted from the body.

Reference is now made to FIGS. 10A-10E which represent the proximal portion 102 in different stages of the deployment and the attachment. As can be seen from the figure, the proximal end 102 can comprises numerous handles. A dedicated handle 113 is adapted to reversibly transform the FAs 104 from their close stage (initial stage) to their open stage (final stage). A second handle 1001 is adapted to activate clips 108 such that the patch 106 is at least partially attached to the tissue 501 by pulling the activation wire 112. Handle 1002 is adapted to release the patch 106 from the FAs by cutting the stretching wire 107. Handle 1002 is also adapted to cut the activation wire 112. Button 1003 is adapted to release handle 113 such that the FAs 104 return to their close stage.

Figure 10A:
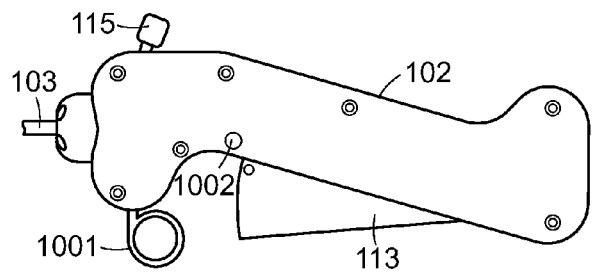
FIGS. 10A-10E represent the proximal portion 102 in different stages of the deployment and the attachment.
Figure 10B:
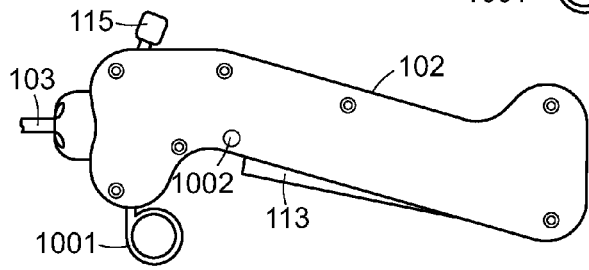
Figure 10C:
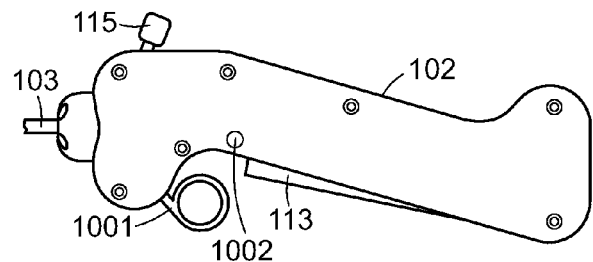

FIG. 10A illustrates the initial stage at which none of the handles are pressed. In FIG. 10B, handle 113 is presses thereby transforming the FAs 104 from the close stage to the open stage thereby deploying the patch 106. After the patch 106 is deployed, the physician can move and rotate the deployed patch 106. This is preformed in order to bring said patch adjacent to the tissue. The physician can apply pressure needed for the attachment process.

Figure 10D:
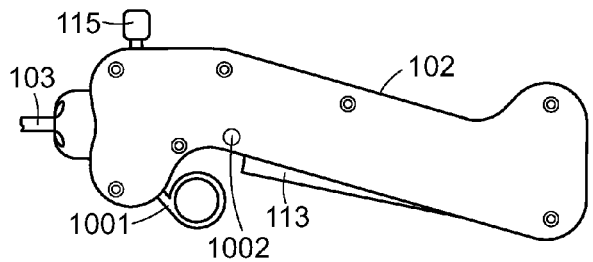
Figure 10E:
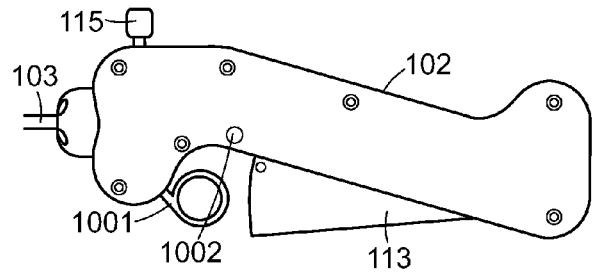
Figure 11:
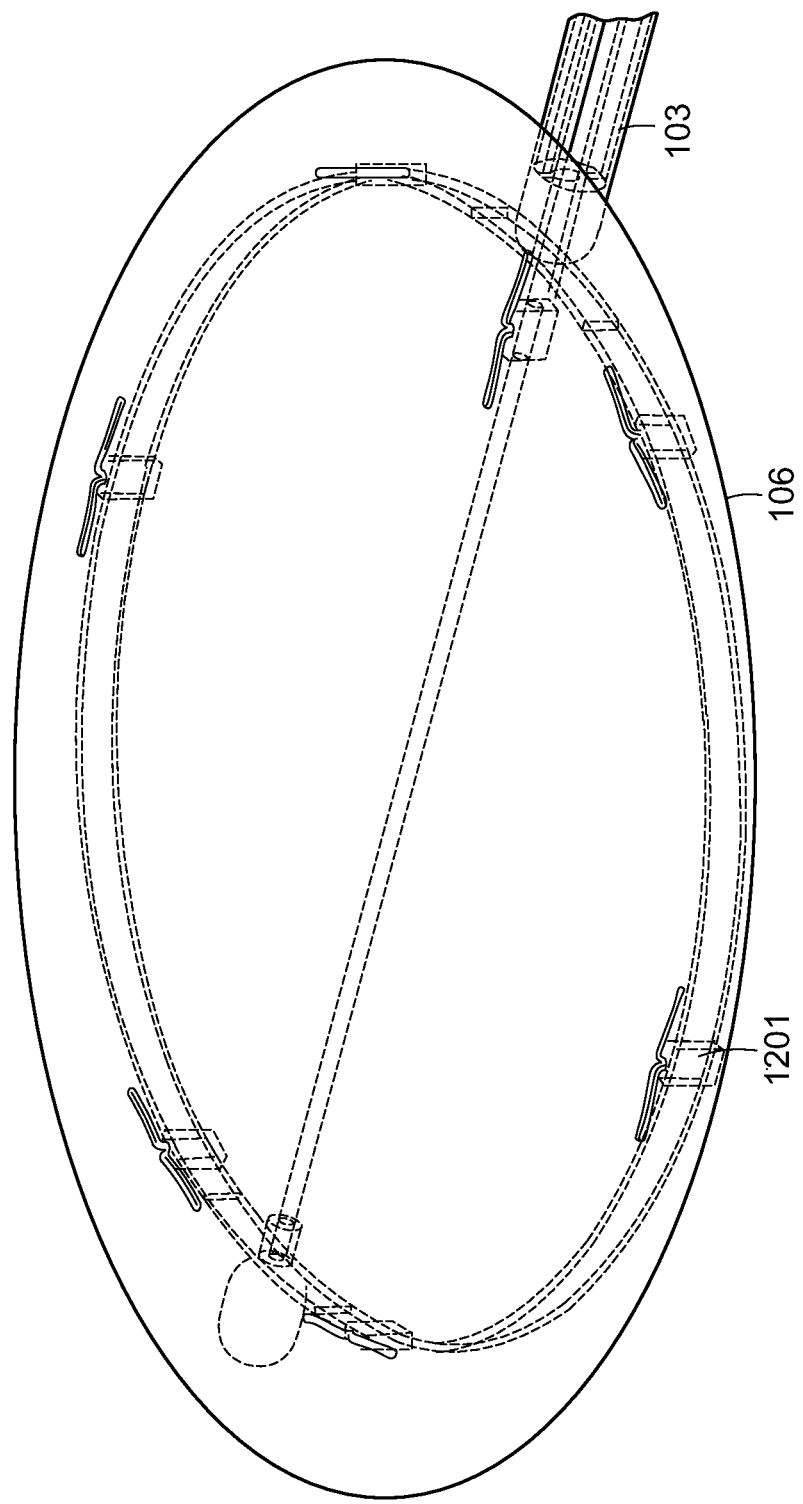

When the patch is located adjacent to the tissue, handle 1001 is presses (FIG. 10C) thereby activating the clips (by pulling the activation wire 112) and the patch is now attached to the tissue. After the patch is securably attached to the tissue, handle 115 is presses, thereby the cutting the stretching wire 107 and the activation wire 112 (FIG. 10D). Now the patch is released from the FAs 104 and the FAs can return to the close stage and be extracted from the body (by pressing on button 1002, FIG. 10E).

It is in the scope of the present invention wherein the device 100 which is adapted to deploy and attach a patch is useful in minimal invasive heart surgeries for attaching a patch to the heart, for preventing heart failure due to aneurysm.

It is in the scope of the present invention wherein the device 100 which is adapted to deploy and attach a patch is useful in endoscopic colon surgeries.

It is another object of the present invention to provide a deployment and attachment device in which clips 108 are at least partially connected to the patch (instead of the FA) prior to the attachment. In this embodiment the clips 108 are initially coupled to the patch and not to the FAs. Furthermore, in this embodiment the role of the FAs is to deploy the patch and to press it against the tissue.

Reference is now being made to FIGS. 11 and 12A-12G which describe different coupling means between the patch 106 and the FAs 104.

One of the advantages of the coupling means is the fact that no wires are used. Thus, enabling fast and simple mounting of the patch 106 on top of the FAs 104 during surgery.

The coupling is based on dedicated patch-FA clips 1201 which are connected to the FAs 104.

Figure 12A:
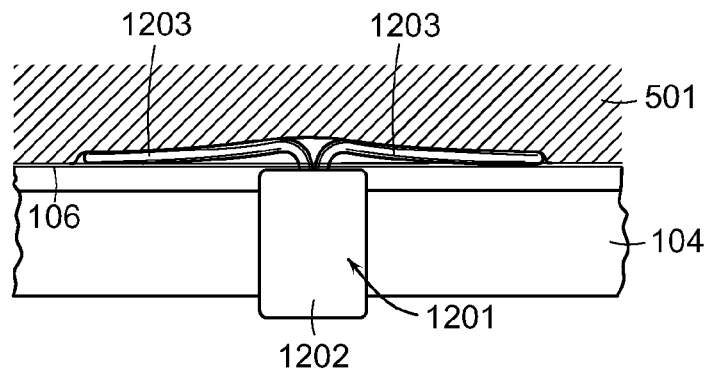

Reference is now made to FIG. 12A which presents a closer view of the clip 1201. The clip 1201 has a main portion 1202 and at least one flexible branches 1203 extruding (or protruding) out from the main portion 1202. When the branches 1203 are not subjected to external load, they buckle laterally, therefore, provide attachment between the FA 104 and the patch 106.

Figure 12B:
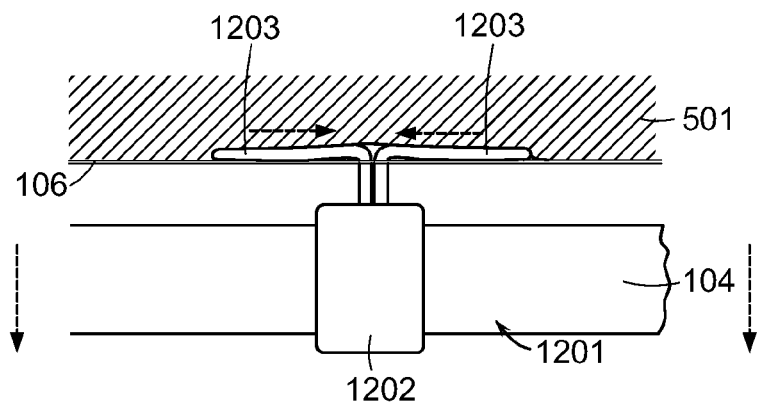
Figure 12C:
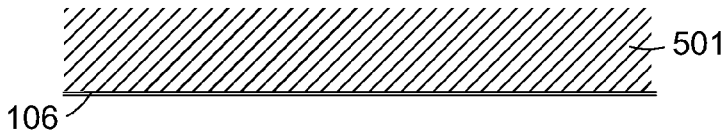
Figure 12C:
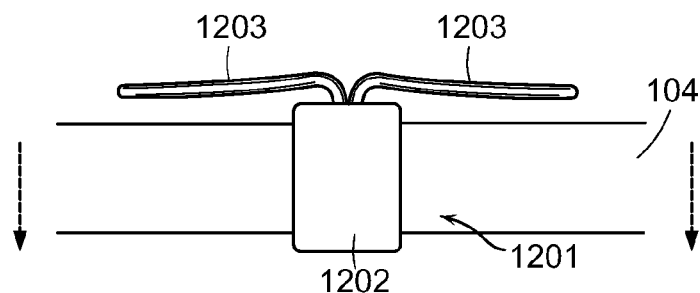

Reference is now made to FIGS. 12A-12C which describe the method of de-activating the clip 1201 (i.e., disconnecting the clip 1201 from the patch 106).

Once the patch 106 is attached to the tissue 501, the user could disconnect the patch by pulling the FA 104 away from the tissue. As a result the branches 1203 are deformed (from a position being parallel to the tissue to a potion being perpendicular to the same). Thus, the branches 1203 pass through their entrance hole at the patch 106 (FIG. 12A) and are disconnected from the patch.

Once the clips 1201 are disconnected from the patch it resumes its original shape (in which the branches 1203 are in a parallel position)—see FIG. 12C.

According to one embodiment of the present invention, in order to allow correct folding and unfolding of the patch 106, without the creation of tension on the patch 106 and on the FA 104, some of the clips 1201 could move freely along the FA 104, while others will be fixed to their place.

FIGS. 12D-12G describes the process of mounting the patch 106 on the deployment system. In order to enable simple insertion of the clip 1201 through the patch 106, the clips 1201 are delivered to the user together with a sharp cap (i.e., envelope covering) 1204 as can be seen from FIG. 12D.

The cap will accommodate the branches 1203 in a vertically alignment (in relation to the FA 104). In a preferred embodiment, the user (a surgeon or a nurse) will insert the cap 1204 whilst accommodating the clip 1201 through the patch during the surgery (see FIG. 12E). Once all the clips 1201 are inserted through the patch the caps 1204 are removed from each individual clip 1201 (see FIG. 12F). As a result the branches 1203 buckle laterally (i.e., into a parallel position in relation to the tissue). Thus, providing attachment between FA 104 and the patch 106 (see FIG. 12G).

Figure 12H:
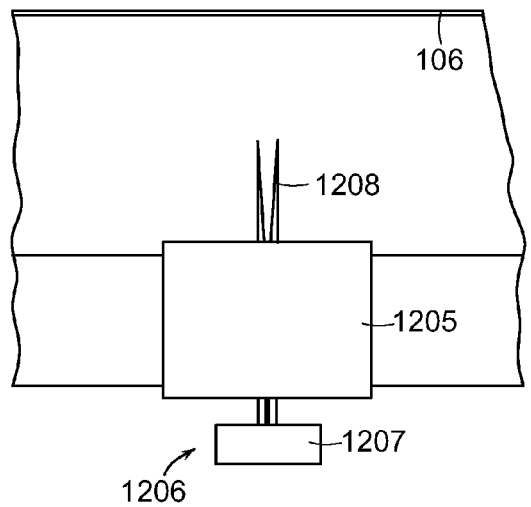
FIGS. 12H-12J illustrate an approach of mounting the patch 106 on the deployment system (i.e., another embodiment to the patch-FA clips 1201).
Figure 12I:
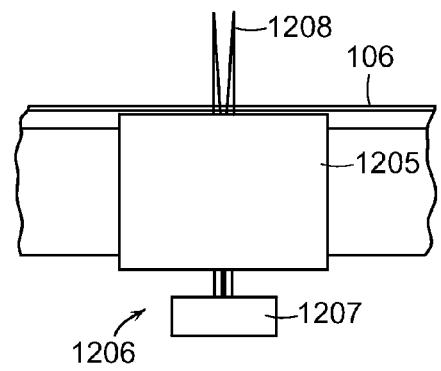
Figure 12J:
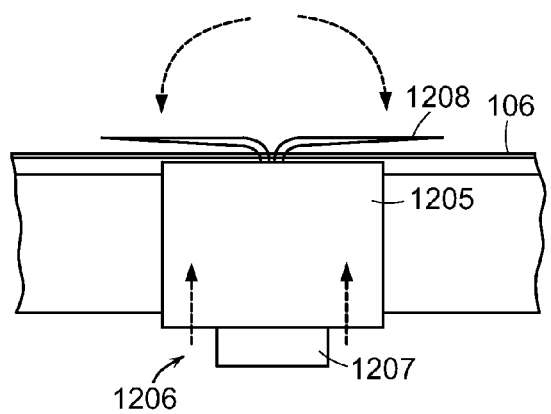
Figure 12K:
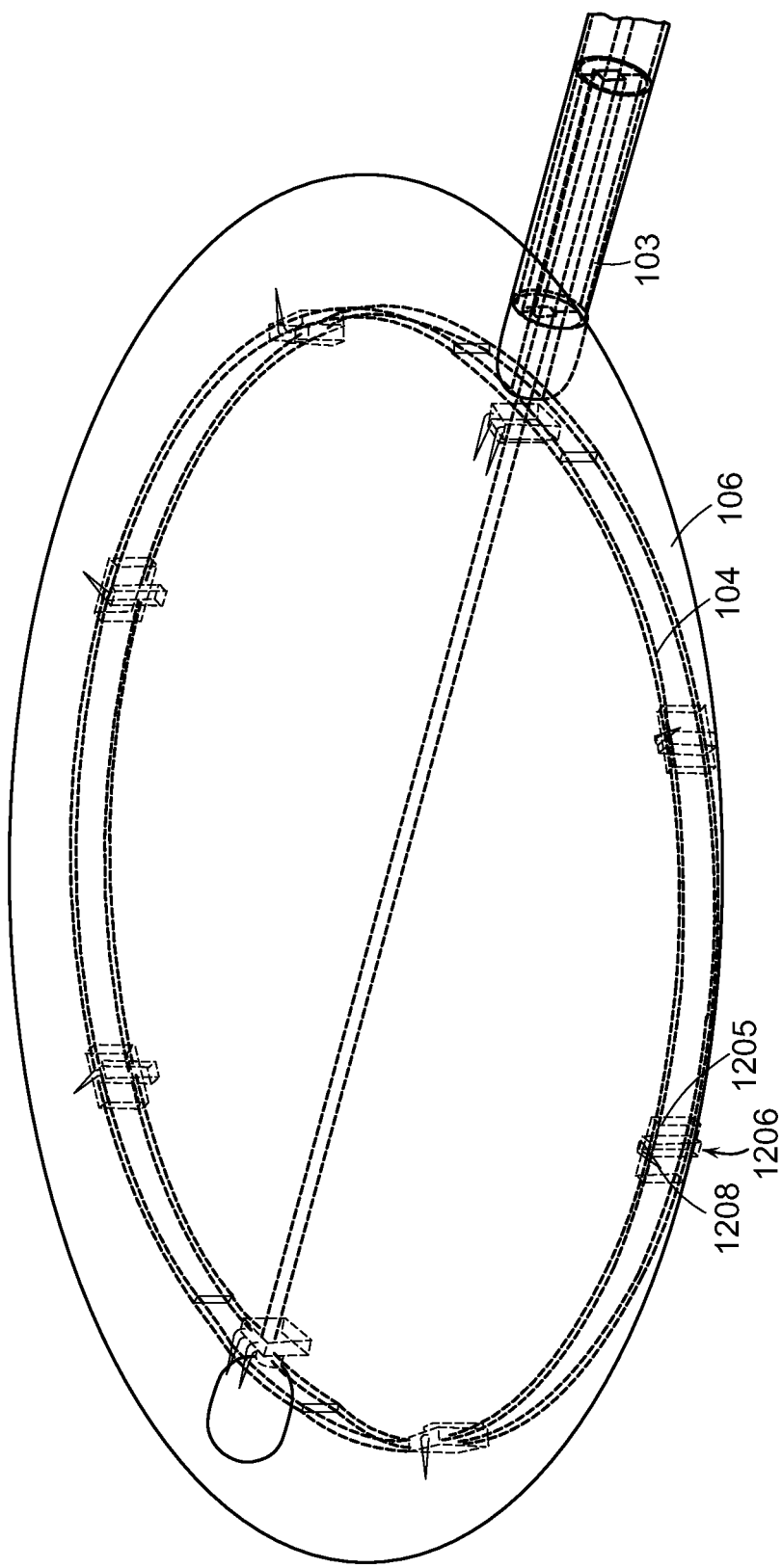
FIGS. 12K-12Q illustrate another approach of mounting the patch 106 on the deployment system (i.e., another embodiment to the patch-FA clips 1201).
Figure 12L:
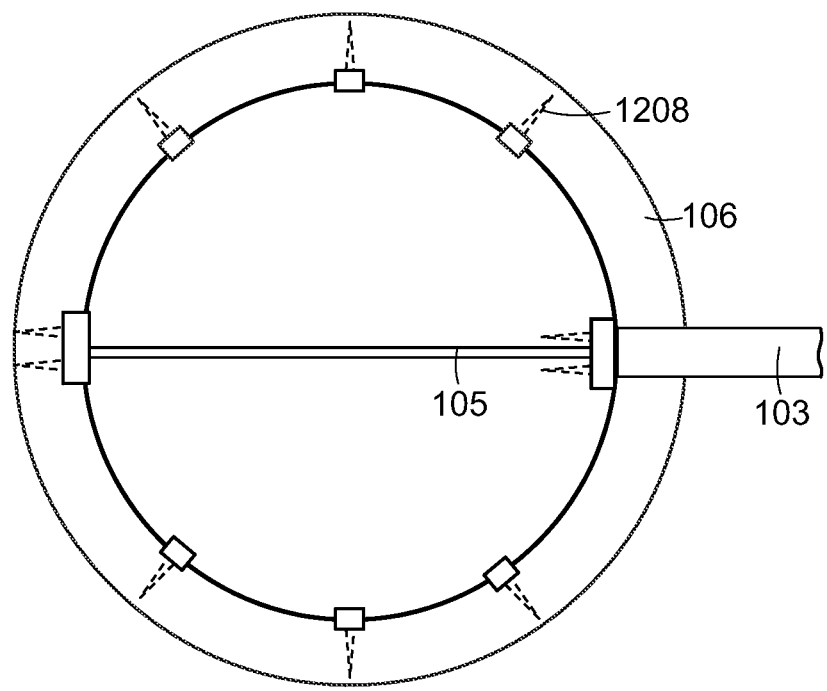
Figure 12M:
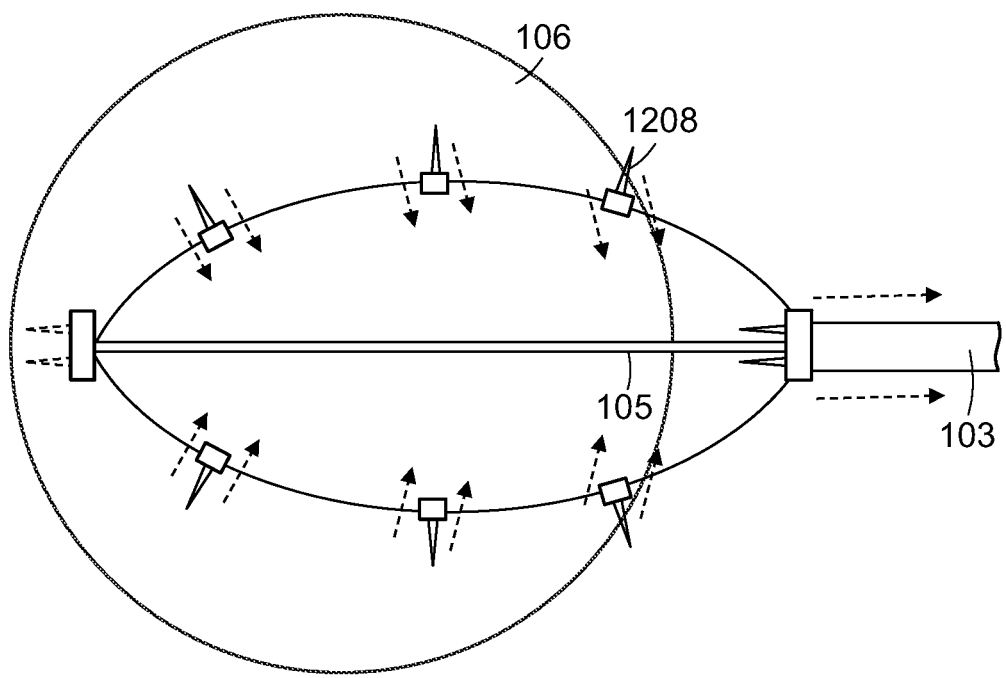

FIGS. 12H-12J illustrate an alternative approach of mounting the patch 106 on the deployment system. According to this approach, the clip 1201 comprises two separate portions: (a) a main portion 1205 which is connected the FA 104; and, (b) a second portion 1206. Portion 1206 have at least one branch 1208 connected to a pressing area 1207. Initially, the branches 1208 are partially inserted into a channel within the main portion 1205, such that they are vertically aligned, and their distal end protrudes out from the top end of the main portion 1205 (see FIG. 12I). The main role of portion 1205 is to retain the branches 1208 from buckling laterally.

Said attachment between patch 106 and FAs 104 is obtained by inserting the patch 106 through the branches 1208 (see FIG. 12I) and then portion 1206 is pressed upward, toward the patch. The branches, which is no longer confined by the main portion 1205, buckle laterally, thus provide the said attachment between patch 106 and FA 104 (see FIG. 12J).

FIGS. 12K-12Q describe another alternative approach of mounting the patch 106 on the deployment system. In this approach, the branches 1208 of each clip are bended radially, toward or away the center of the patch (see FIG. 12K).

Figure 12N:
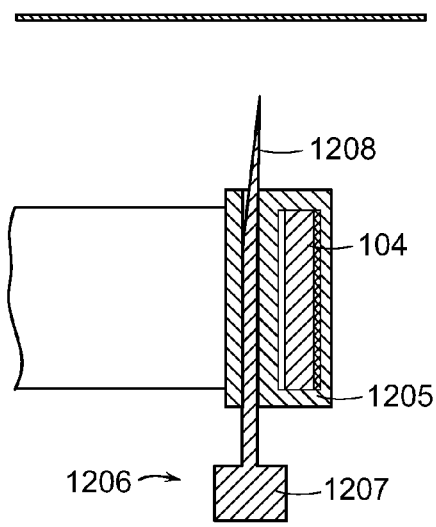
Figure 12O:
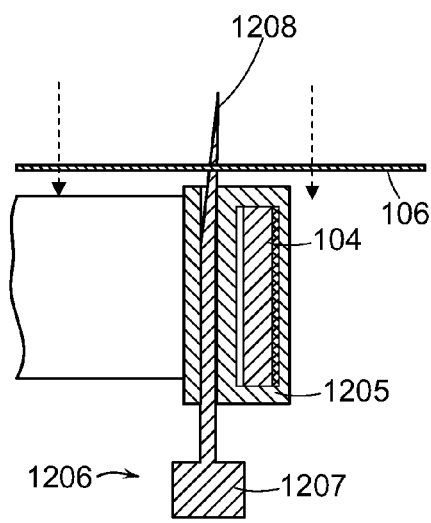
Figure 12P:
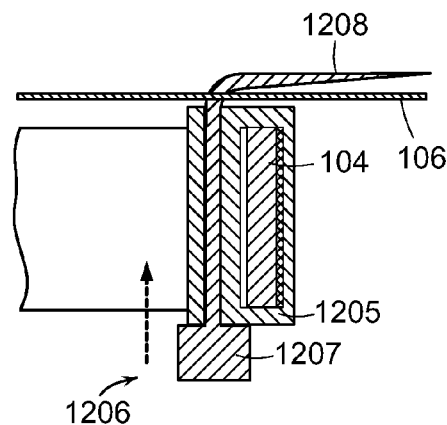
Figure 12Q:
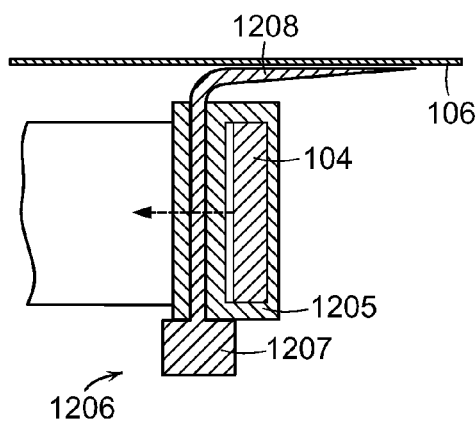
Figure 13A:
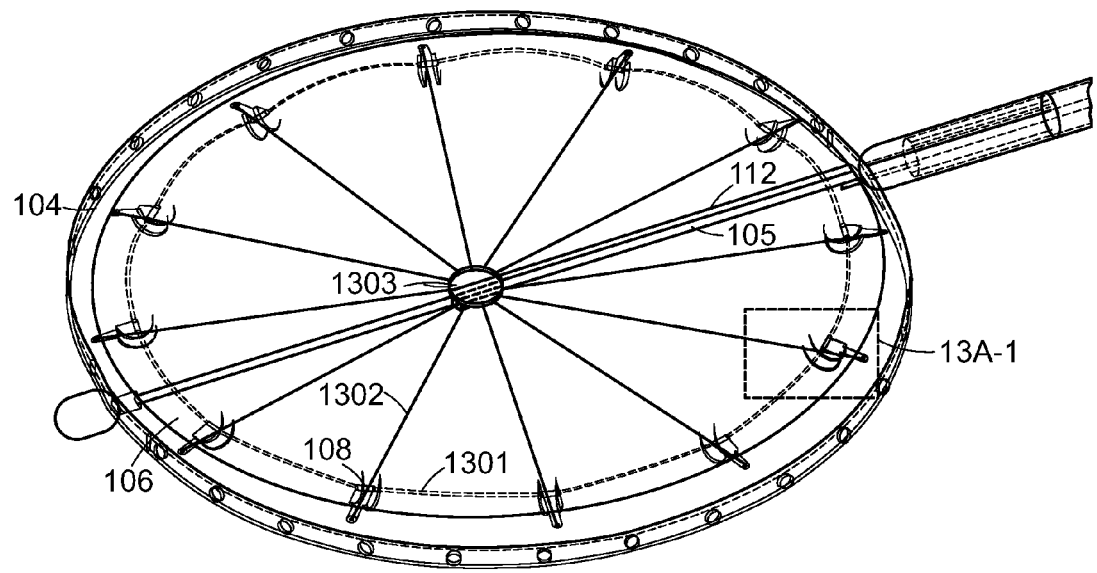
FIGS. 13A-13F illustrate an alternative embodiment for attaching patch 106 to the tissue 501 by several clips 108.
Figures 1, 13A:
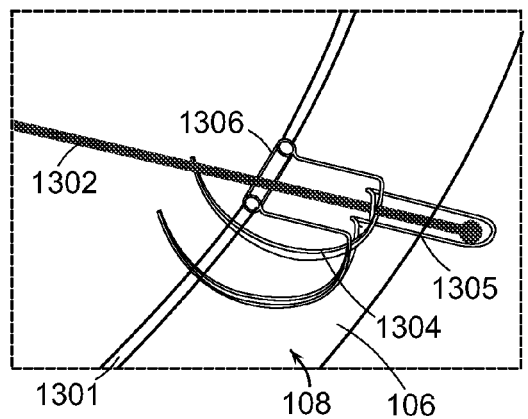

Once the patch 106 is attached to the tissue 501, the FAs 104 are closed. As a result the branches 1208 move radially, therefore, disconnecting form the patch 106, as can be seen at FIGS. 12M-12Q. In a preferred embodiment, the mounting process of patch 106 on top FAs 104 is similar to the previously described approach as can be seen in FIGS. 12N-12P Reference is now being made to FIGS. 13A-13F which describes an alternative embodiment for attaching patch 106 to the tissue 501 by several clips 108. In this embodiment, as can be seen in FIG. 13A and FIG. 13D, the clip 108 is connected to a wire 1301 which is incorporated within the patch 106. The connection between clip 108 and wire 1301 is at a wire connection area 1306 and will enable free rotation of the clip 108 around the wire 1301.

The clip 108 will have a central plate 1305 and at least two sharp arms 1304 connected to each side of the plate. In a preferred embodiment, the arms 1304 are curved. An activation wire 1302 will be coupled to the plate 1305. Once the wire 1302 is pulled, during surgery, the entire clip 108 is rotated around wire 1301.

The activation wires 1302 from each clip 108 will be connected to a central activation area 1303 (see FIG. 13B) which will pull all the activation wires 1302 toward the center of the patch 106 once the attachment between patch 106 and tissue 501 is needed. The central activation area 1303 will be activated by pulling the clip activation wire 112, or by rotating the central shaft 105.

Figure 13B:
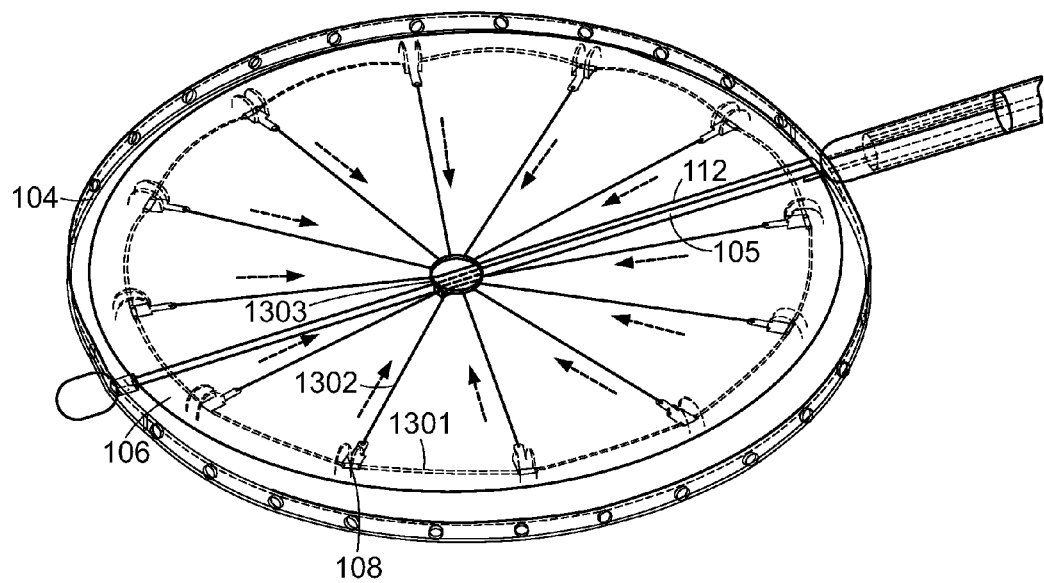
Figure 13C:
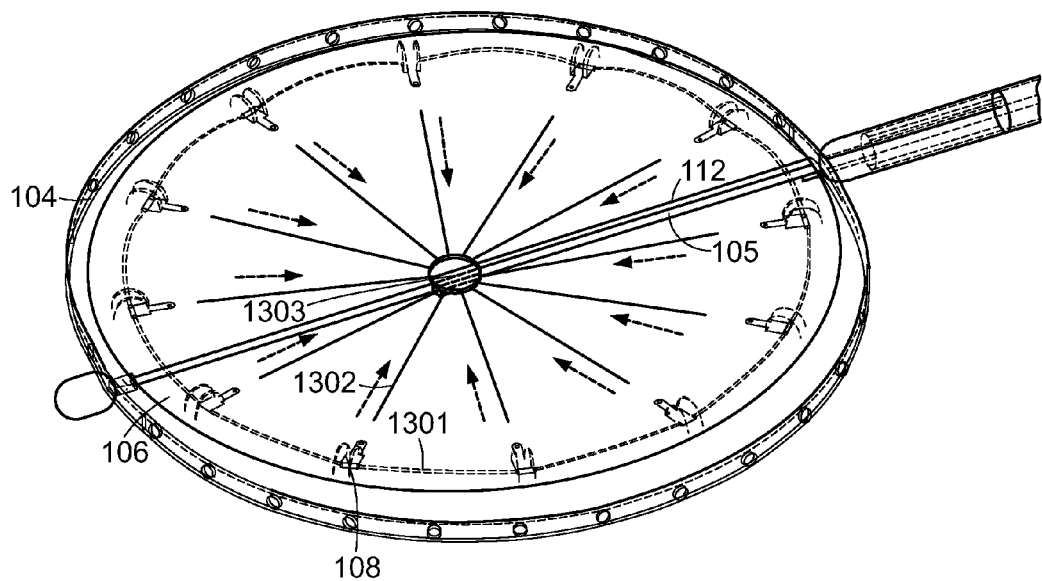
Figure 13D:
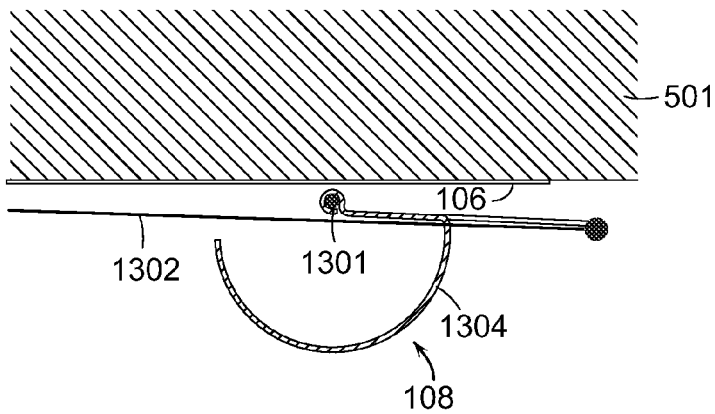
Figure 13E:
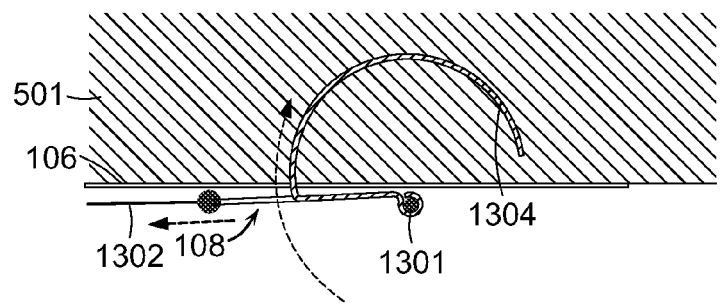

As can be seen in FIGS. 13B and 13E, once the central activation area 1303 is activated, each activation wire 1302 is pulled toward the center, therefore inducing rotational movement of each of the clips 108 around wire 1301. As a result, the arms 1304 (of each clip 108), are inserted through the patch 106 and the tissue 501. Thus, providing attachment between the tissue 501 and the patch 106.

Once the attachment (between the patch and the tissue) is achieved, the wire 1302 is disconnected from the central activation area 1303 in order to enable proper detachment between the connected patch 106 and the rest of the deployment system.

Figure 13F:
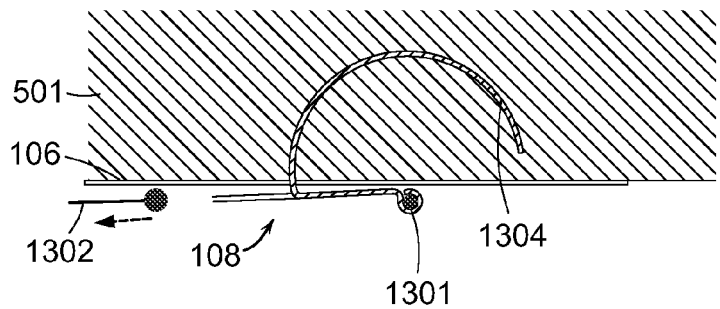

In a preferred embodiment of the current invention the connection between clip 108 and the activation wire 1302 is considerably weaker than the rest of the wire 1302 but strong enough to rotate the clip 108. Once the clip is fully inserted into the tissue, the activation wire will be pulled using sufficient force for disconnecting it for the clip 108 (FIG. 13C, 13F). In other words, pulling the activation wire 1302 in F amount of force enables the insertion of the clip 108 into the tissue; and, pull the activation wire 1302 in F1 amount of force (F1 is sufficiently greater than F) enables the disconnection of the activation wire 1302 from clip 108.

Reference is now being made for FIGS. 14A-14D which describe an alternative detachment mechanism between the patch 106 and the FAs 104. According to this embodiment, the central shaft 105 is extended from the proximal side of handle 102 (FIG. 14A), therefore the unfolding process can be achieved be pulling the central shaft proximally.

The distal end of shaft 105 is inserted to a sleeve 1401 located at the distal end on the FAs 104. The sleeve 1401 have two lateral holes 1402 initially concentric to a hole 1403 at the distal end of the central shaft. When hole 1402 and hole 1403 are aligned, the stretching wire 107 can pass through them (see FIG. 14C).

Figure 14A:
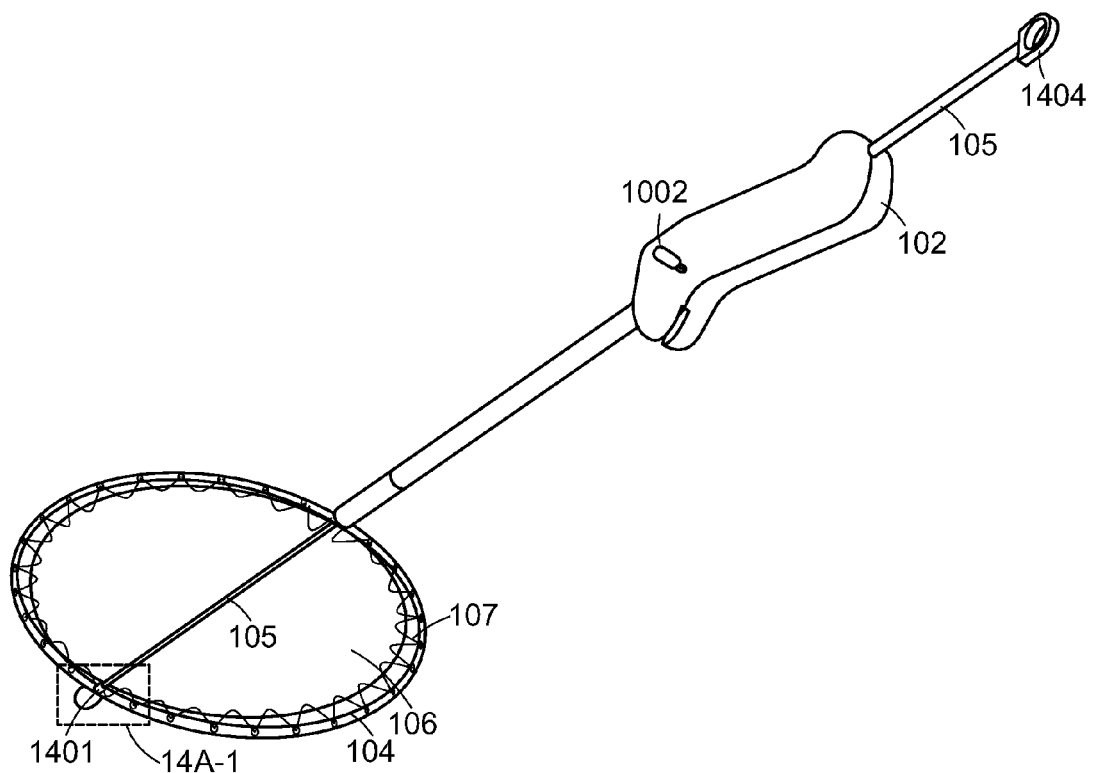
FIGS. 14A-14D illustrate an alternative detachment mechanism between the patch 106 and the FAs 104.
Figures 1, 14A:
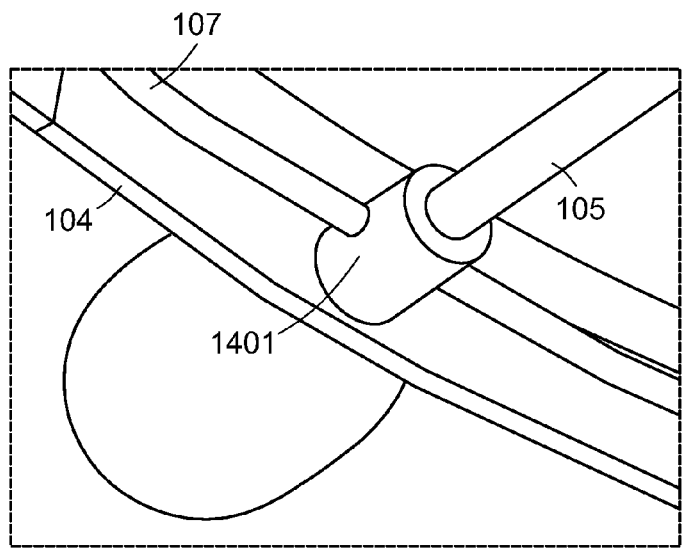
Figure 14B:
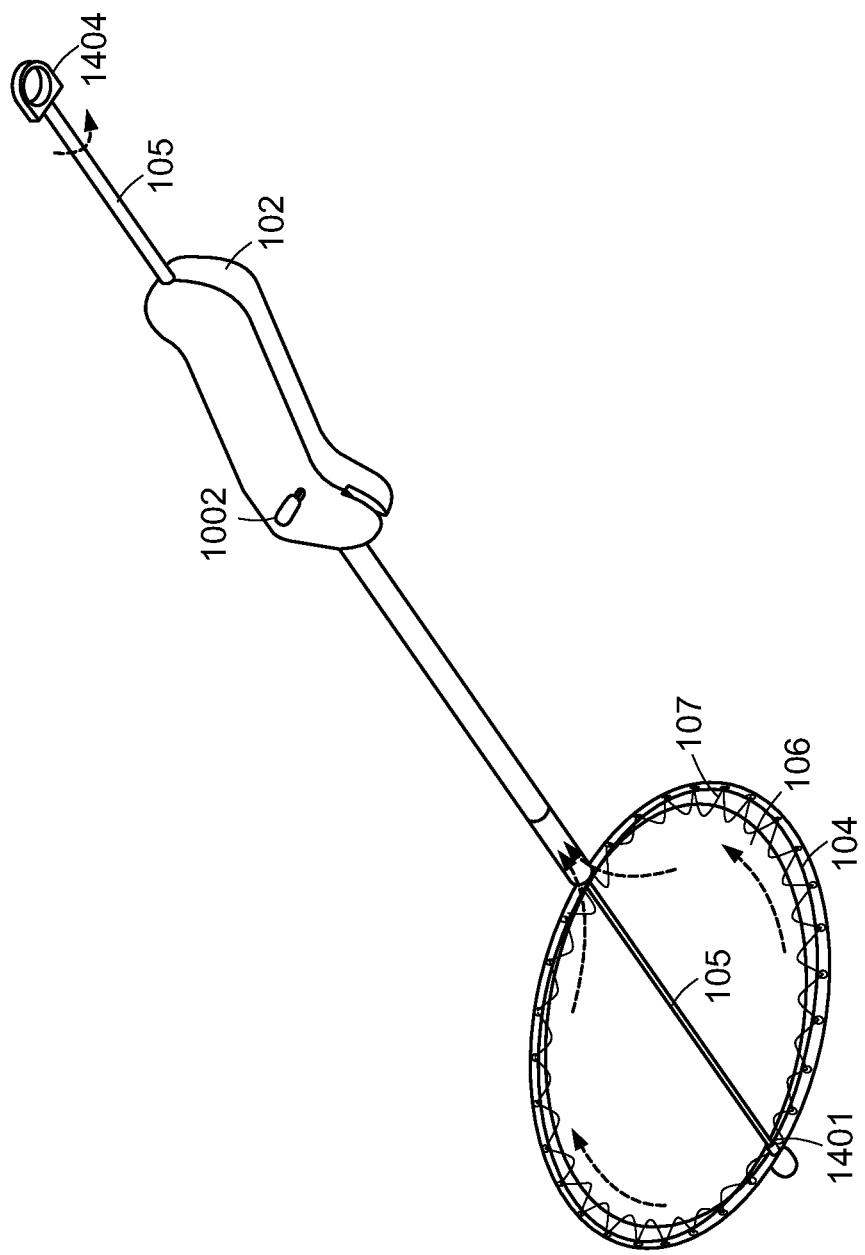
Figure 14C:
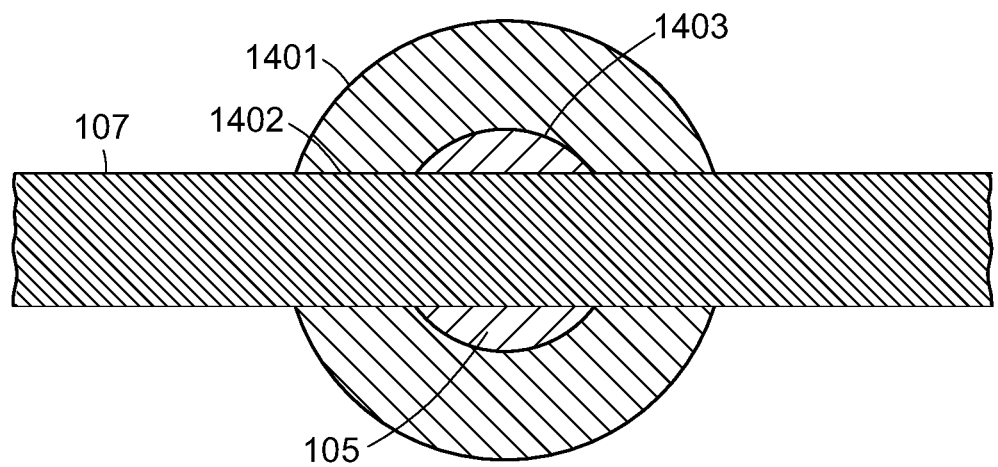
Figure 14D:
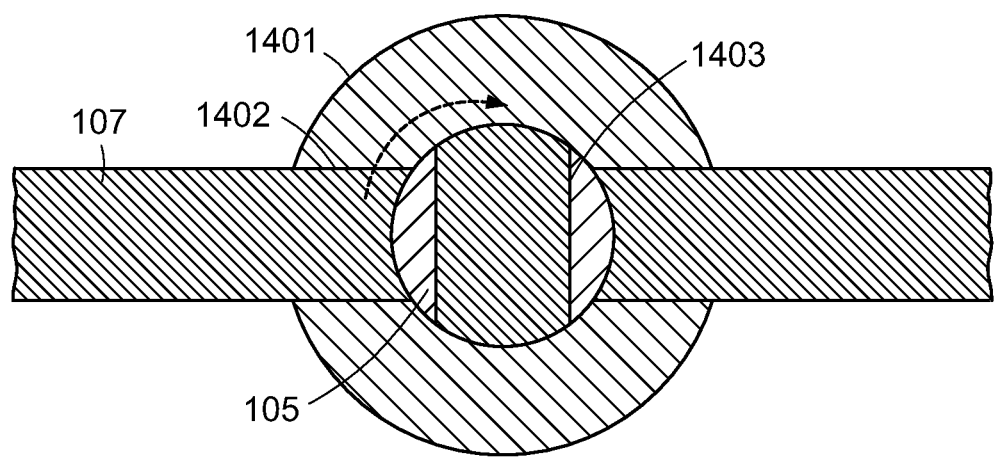

The stretching wire is kept constantly in tension, therefore keeps a sufficient tension applied on the patch 106 during the unfolding process, and prevents wrinkles. Once the patch 106 is attached to the tissue 501, the user will rotate handle 1404 which is located at the proximal end of the central shaft 105 (FIG. 14B). This rotational movement cuts the stretching wire 107 at the distal end of the central shaft 105 (FIG. 14D). This cutting cuts the stretching wire 107 into two halfs (sections). Since there the stretching wire 107 are tensed, the two ends of the already cut wire 107 will be instantly pulled toward the proximal end of the system, therefore canceling the attachment between patch 106 and the FAs 104.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

Reference is now made to FIGS. 15A-15D which illustrate an embodiment in which the patch can be laterally rotate with respect to the tissue such that the right orientation of the patch is facing the tissue or the hernia.

Figure 15A:
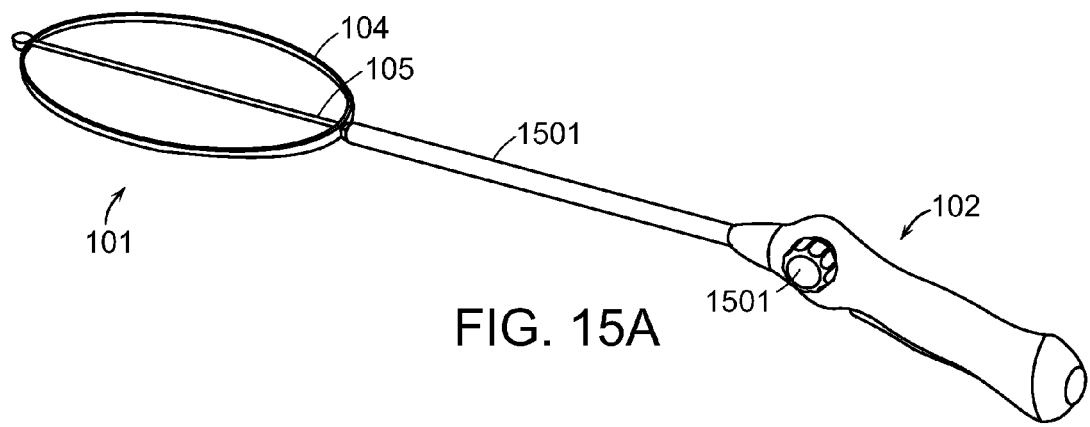
FIGS. 15A-15D, illustrate the controllable/flexible joint 103.
Figure 15B:
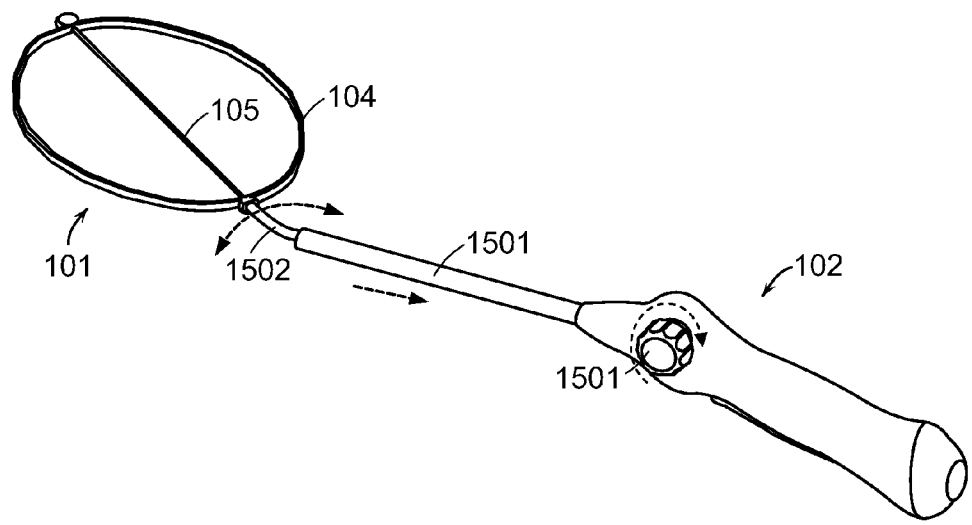

Reference is now being made for FIGS. 15A-15B, which describes an embodiment in which at least a part of tube 103 is a controllable and flexible joint 1502. This joint is especially adapted to allow fine adjustment of the lateral angle between distal portion 101 and the proximal portion 102 during the procedure.

In other words, the controllable and flexible joint is provided in order to adjust the right orientation of the patch with regards to the tissue or the hernia.

Such adjustment is needed in order to aline the patch 106 with a desirable lateral position with regards to tissue 501. According to this embodiment, the controllable and flexible joint 1502 is made of flexible material (e.g. polymer) and can be curved according to predetermined angle in its distal end. The controllable and flexible joint 1502 is housed by a rigid alignment tube 1501. Said rigid alignment tube 1501 can be reciprocally moved along it longitudinal axis.

It should be emphasized that the controllable and flexible joint 1502 has an intrinsic spring-like properties; i.e., the controllable and flexible joint 1502, when is unloaded, returns to its original curved/bent shape.

At the initial state (FIG. 15A) the controllable and flexible joint 1502 is completely encapsulated within the rigid alignment tube 1501 such that controllable and flexible joint 1502 it forced to be straight and linear, once the distal portion 101 is inserted into the patient body and lateral angle adjustment is required, the rigid alignment tube 1501 is pulled toward the proximal portion 102; as a result, the controllable and flexible joint 1502, which is no longer supported by the rigid alignment tube 1501, is bent/curved into its original form, thus providing the desire angle between the proximal portion 102 and the distal portion 101 (FIG. 15B).

By controlling the location of the rigid alignment tube 1501 with respect to the controllable/flexible joint 103, a fine adjustment of the angle is obtained. As mentioned above, the control over the rigid alignment tube's 1501 location is provided by the amount of pulling or pushing of said rigid alignment tube 1501 towards and away from the proximal portion 102.

Since the surgeon controls said rigid alignment tube's 1501 location, he therefore controls the angle between the distal portion 101 and proximal portion 102.

The movement (and thus the angle between the distal portion 101 and proximal portion 102) is adjusted by the angle control means 1502 which is located at the proximal portion 102.

Figure 15C:
Figure 15D:
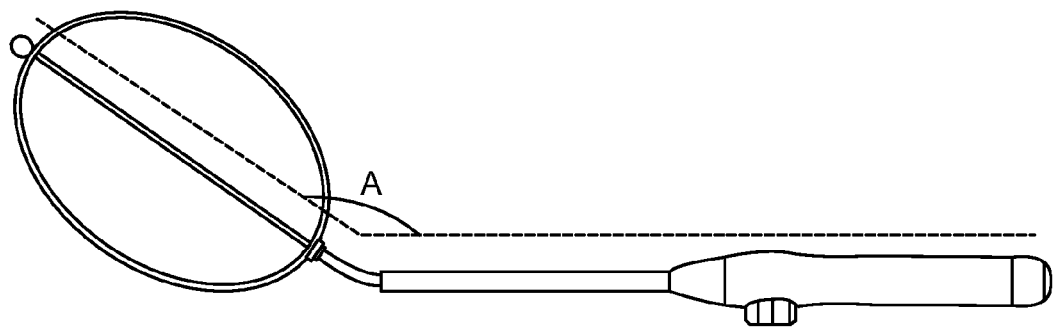

Reference is now made to FIGS. 15C-15D which illustrate a top view of the system. In FIG. 15C the rigid alignment tube 1501 is fully housing/encapsulating the controllable and flexible joint 1502 and thus the angle between the distal portion 101 and proximal portion 102 is 0 degrees.

FIG. 15D also illustrates a top view of the system. However, in FIG. 15D the rigid alignment tube 1501 is not fully housing/encapsulating the controllable and flexible joint 1502, thus the controllable and flexible joint 1502 is curved/bent according to the location of the rigid alignment tube's 1501 with respect to the controllable and flexible joint 1502. Therefore, an angle A is obtained between the distal portion 101 and proximal portion 102.

Figure 16A:
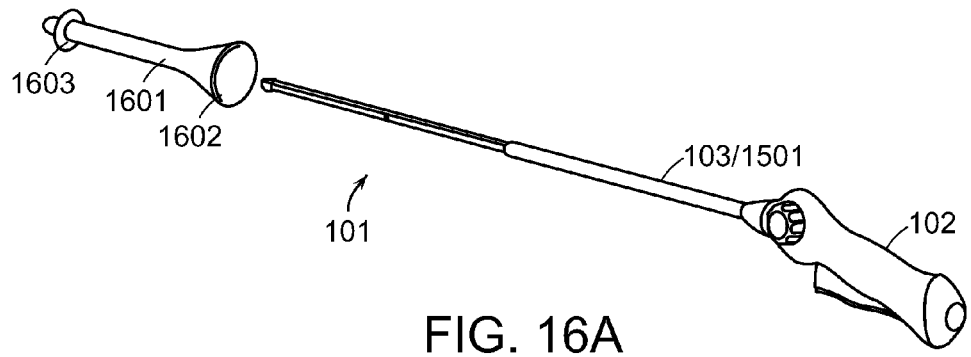
FIGS. 16A-16C illustrate the patch insertion sleeve.
Figure 16B:
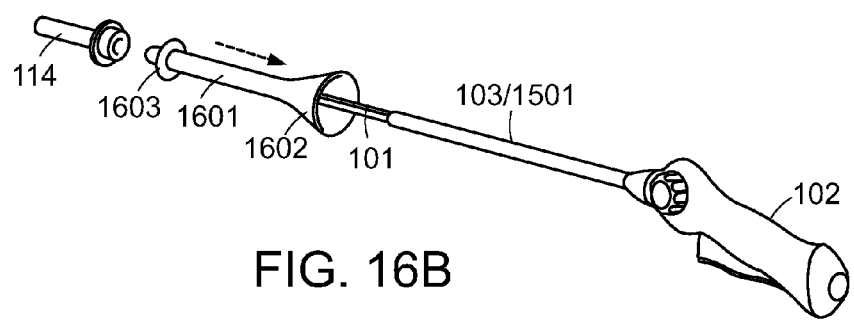
Figure 16C:
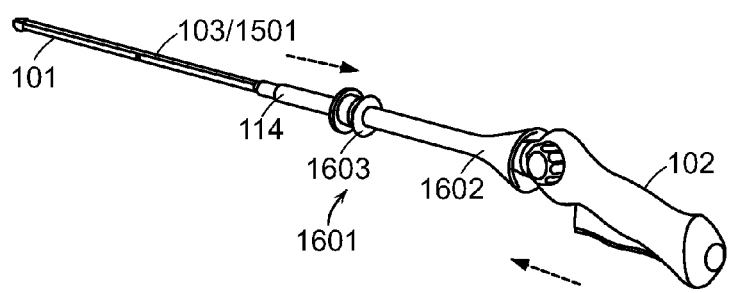

Reference is now being made to FIGS. 16A-16C which describe an embodiment of the patch insertion sleeve. Such a sleeve/cover is needed in order to facilitate, to ease and to catalyze the insertion of the distal end 101 and the patch 106 in to the patient's body.

According to this embodiment the insertion sleeve 1601 is an elongated rigid tube with a cone shaped expansion 1602 at its proximal end and a stopper 1603 near its distal end. Once the patch 106 is mounted and folded on the distal portion 101 (during the surgery or during the assembly process prior to the surgery), it is inserted, together with the distal portion 101, into the insertion sleeve 1601 trough the cone shape expansion 1602, such that the distal end of the insertion sleeve 1601 reaches the distal end of the distal portion 101 (FIG. 16B).

The overall complex is then inserted to the patient's body through a trocar 114. The outside diameter of the insertion sleeve 1601 at the portion between its distal end and the stopper 1603 is smaller or equal to the inside diameter of the trocar 114, such that this portion can be inserted into the trocar 114. Once the stopper 1603 reaches the trocar 114 proximal end, the distal portion 101 and the patch 106 slide out of the insertion sleeve and into the trocar 114 and the patent body, while the insertion sleeve is slide backward along the rigid alignment tube 1501 or the tube 103. At the final stage (FIG. 16C), the distal portion 101 and the patch 106 is completely inserted into the patient's body.

Reference is now being made to FIGS. 18A-18D which illustrate an additional embodiment of the deployment mechanism. This embodiment provides larger patches deployment using the same initial length of the distal portion 101; in addition, it will allow a simpler reversible attachment between patch 106 and the distal FA 104.

According to this embodiment each FA 104 additionally comprises a long rod 1801 which is aligned parallel to the central shaft. The rods 1801 are connected to the FA 104 via at least one joint or flexible portion.

According to this embodiment, the patch 106 is reversibly connected to the rods 1801 rather than the FAs 104. The patch 106 is deployed by a reciprocal movement of the central shaft 105 toward the proximal portion. As a result, the rods 1801 are laterally moved away from each other, providing patch deployment.

Figure 18A:
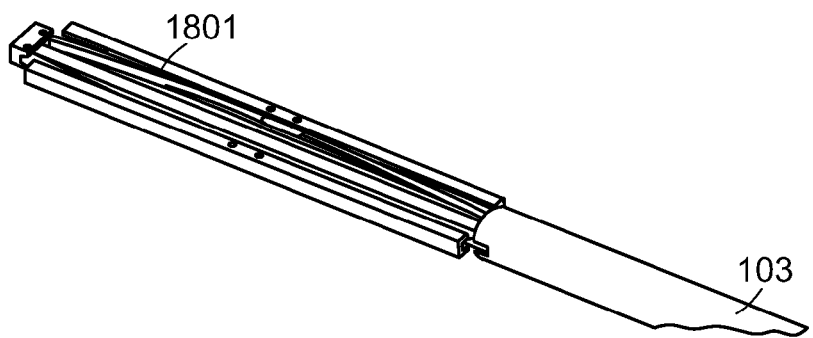
FIGS. 18A-18D illustrates another preferred embodiment of the deployment system.
Figure 18B:
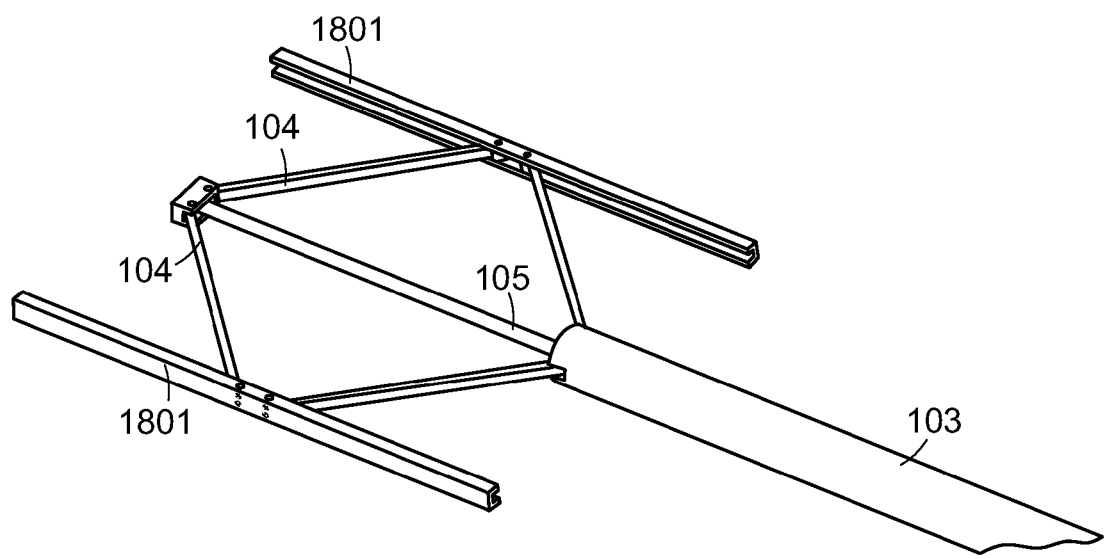
Figure 18C:
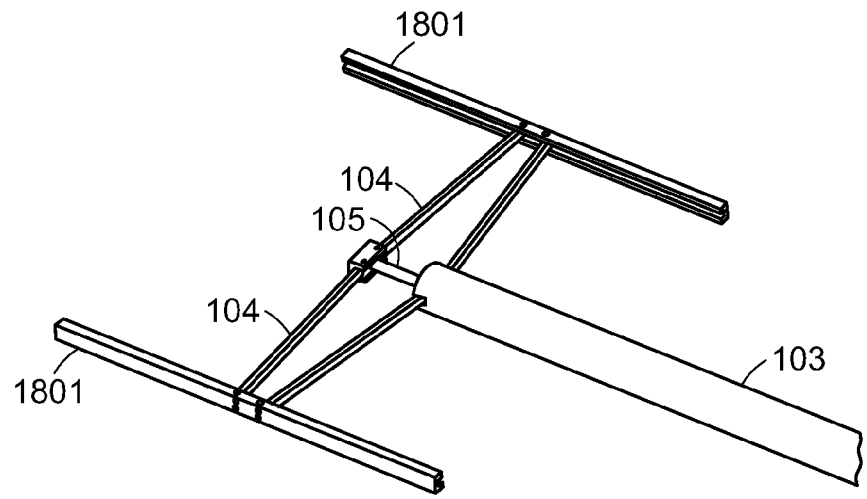
Figure 18D:
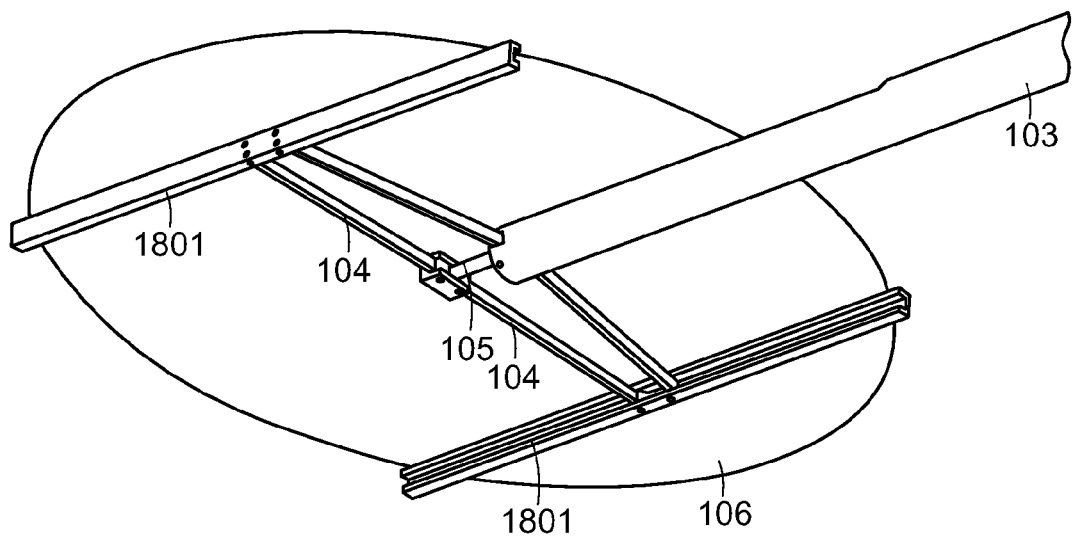

FIG. 18D illustrate the above embodiment incorporated with the patch 106.

Figure 19:
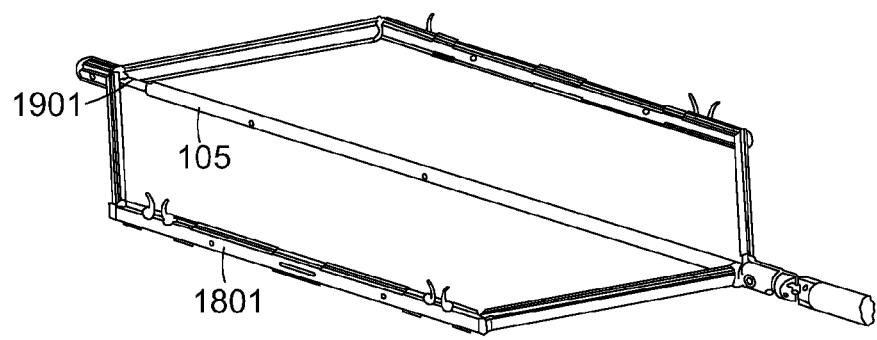
FIG. 19 illustrates a deployment system having a telescopic central shaft.

Reference is now being made to FIG. 19, which shows an embodiment of a deployment device having a telescopic shaft. In this embodiment, the central shaft is hollow and a rod 1901 is slideably disposed within the central shaft. In the closed configuration, the rod is extended from within the central shaft, resulting in the frame collapsing around the central shaft. In the deployed configuration, the rod is retracted into the central shaft, causing spreading of the frame and expansion of the patch. FIG. 19 shows the deployment device in a deployed state, with the rod retracted within the central shaft, thereby expanding the frame. At least a portion if said rod is flexible in order to enable lateral and vertical articulation. This embodiment allows for a more rigid structure and allows articulation without fully deploying the frame.

Reference is now being made to FIG. 20, which shows an embodiment of a deployment device in which there is a connection between the central shaft and the side arms of the frame in a closed configuration. This connection helps prevent a potential failure of the side arms during mesh rolling and allows better and tighter rolling of the mesh. The connection is canceled once the frame is opened in order to allow deployment.

Figure 20A:
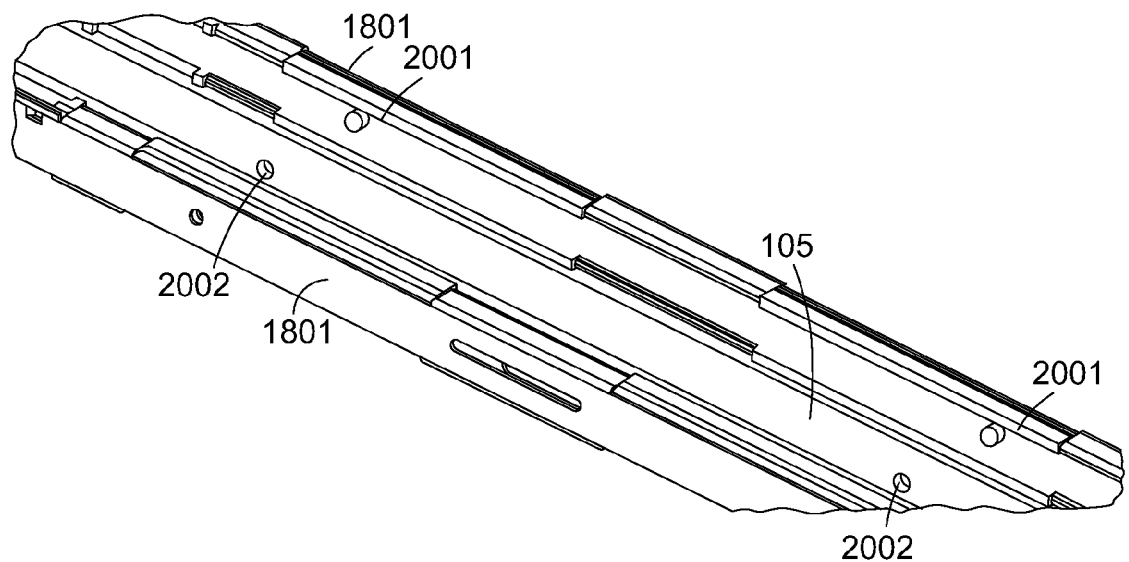
FIGS. 20A-20C illustrates a deployment device having a connection between the central shaft and side arms in a closed configuration.

In the embodiment described in FIG. 20A, said connection is obtained by four individual pins 2001, two at each side arm 104; said pins 2001 are inserted into holes 2002 at the central shaft 105 once the device 100 is positioned in its closed configuration. Since the pins are tightly fits inside the holes, the two side arms 104 are held adjacent to the central shaft, therefore a minimal cross section of the device 100 in its closed configuration is achieved; in addition, said pins 2001 prevents potential failure of the side arms during mesh rolling since it prevents the side arms from being moved around central shaft as the result of the rotational loads present during mesh rolling.

Figure 20B:
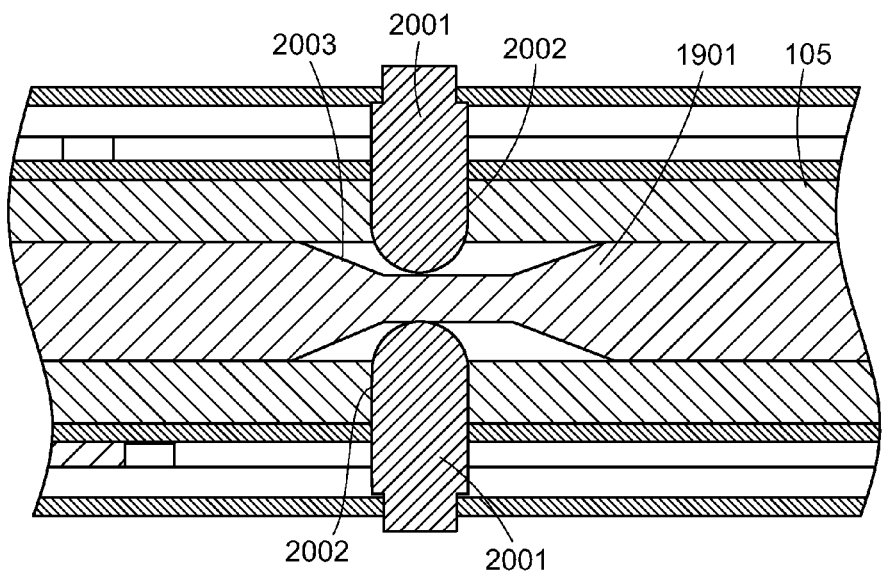
Figure 20C:
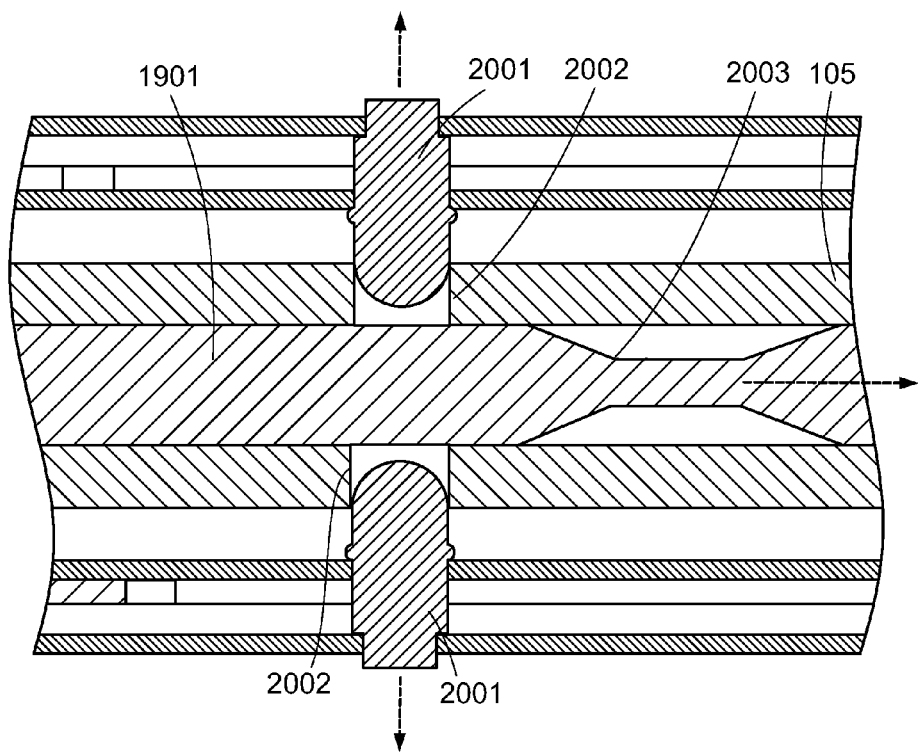

FIGS. 20B-20C illustrates a cross section of a mechanism for releasing said attachment between the side arm and the central shaft once deployment in necessary, such mechanism is important since when the side arms are completely adjacent to the central shaft there almost no lateral force when the central shaft is pulled backward, and in order to allow the opening of the device side arms had to be slightly apart from the central shaft.

Pins 2001 are protruding through holes 2002 into the inner cavity of the central shaft tube. When the system is in its closed configuration the pins 2001 edges is located onside notch 2003 at the central rod 1901 (FIG. 20B). As the system is opened, said rod 1901 is pulled backward therefore pushing pins 2001 outward and releasing said attachment between the central shaft and the side arms. As a result the side arms are located slightly apart from the central shaft and the opening of the device is obtained as the central rod 1901 continues to move backward.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A system for closing an aperture in a biological tissue, the system comprising:
   a handle;
   a telescopic shaft connected to the handle; and
   a deployment scaffold connected to the shaft, wherein the deployment scaffold is configured to releasably retain a surgical implant and the deployment scaffold is configured to deploy and attach the surgical implant to the biological tissue, wherein the deployment scaffold comprises:
   a plurality of deployment arms connected to the telescopic shaft; and
   a plurality of attachment members that are releasably connected to the deployment arms, wherein the attachment members attach the surgical implant to the biological tissue, the attachment members releasable from the arms upon proximal movement of a wire towards the handle, the attachment members releasable in a direction that is perpendicular to a longitudinal extent of the deployment arms.

2. The system according to claim 1, wherein the deployment arms are flexible.

3. The system according to claim 1, wherein the deployment arms are rigid.

4. The system according to claim 1, wherein the number of attachment members is independent of the number of deployment arms.

5. The system according to claim 1, wherein the attachment members are selected from the group consisting of clips, hooks, and barbs.

6. The system according to claim 1, wherein attachment is obtained by rotational or linear movement of the attachment members.

7. The system according to claim 1, wherein the deployment scaffold further comprises:
   a frame;
   wherein the plurality of deployment arms are hingedly connected to the frame, wherein the frame is configured to move from a retained position to at least one deployed position.

8. The system according to claim 7, wherein the deployment arms releasably connect to a central shaft slidably disposed within the telescopic shaft when the deployment scaffold is in a closed configuration.

9. The system according to claim 8, wherein the deployment arms are released from the central shaft by movement of the central shaft from a closed configuration to an open configuration.

10. The system according to claim 1, wherein the deployment scaffold is configured to allow for deployment of the implant and retraction of the implant while the implant is within a patient's body.

11. The system according to claim 1, wherein the deployment scaffold is configured to allow for a plurality of deployment positions.

12. The system according to claim 1, wherein the deployment scaffold comprises an articulating member that allows for adjustment of a position and an orientation of the surgical implant relative to the aperture in the tissue.

13. The system according to claim 12, wherein the articulating member allows for vertical flexibility of the deployment scaffold in order to press the implant against the tissue.

14. The system according to claim 1, wherein the implant is connected to the system in an operating room.

15. The system according to claim 1, wherein the surgical implant is a patch.

16. The system according to claim 15, wherein the patch is comprised of surgical mesh.

17. The system according to claim 1, wherein the telescopic shaft is flexible.

18. The system according to claim 1, wherein the telescopic shaft is rigid.

19. The system according to claim 1, wherein the aperture in the biological tissue is an aperture in an abdominal wall.

20. The system according to claim 1, wherein deployment is accomplished by linear movement of the shaft with respect to the handle.

21. The system according to claim 1, wherein the telescopic shaft comprises:
   a hollow member having a rod that is configured to extend from and retract into the hollow member.

* * * * *

UNITED STATES PATENT AND TRADEMARK OFFICE
CERTIFICATE OF CORRECTION

| | | |
|---|---|---|
| PATENT NO. | : 8,808,314 B2 | Page 1 of 1 |
| APPLICATION NO. | : 12/890816 | |
| DATED | : August 19, 2014 | |
| INVENTOR(S) | : Levin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 553 days.

Signed and Sealed this
Fifth Day of April, 2016

Michelle K. Lee
*Director of the United States Patent and Trademark Office*